US012213701B2

(12) United States Patent
Blurton et al.

(10) Patent No.: US 12,213,701 B2
(45) Date of Patent: *Feb. 4, 2025

(54) EXTERNALLY APPLIED INTRAPARTUM SUPPORT DEVICE

(71) Applicant: Stetrix, Inc., Bartlett, TN (US)

(72) Inventors: David D. Blurton, Whiteville, TN (US); Mark Buchanan, Atoka, TN (US)

(73) Assignee: Stetrix, Inc., Bartlett, TN (US)

( * ) Notice: Subject to any disclaimer, the term of this patent is extended or adjusted under 35 U.S.C. 154(b) by 58 days.

This patent is subject to a terminal disclaimer.

(21) Appl. No.: 18/058,203

(22) Filed: Nov. 22, 2022

(65) Prior Publication Data

US 2023/0157726 A1 May 25, 2023

Related U.S. Application Data

(63) Continuation of application No. 17/542,012, filed on Dec. 3, 2021, now Pat. No. 11,510,699, which is a
(Continued)

(51) Int. Cl.
*A61B 17/42* (2006.01)
*A61B 90/00* (2016.01)

(52) U.S. Cl.
CPC ........ *A61B 17/42* (2013.01); *A61B 2090/065* (2016.02)

(58) Field of Classification Search
CPC .......... A61B 17/42; A61F 5/0093; A61F 6/08; Y10S 128/25
See application file for complete search history.

(56) References Cited

U.S. PATENT DOCUMENTS

| 1,342,588 A | 6/1920 | Higgins |
| 2,672,862 A | 3/1954 | Krauss |

(Continued)

FOREIGN PATENT DOCUMENTS

WO    WO 2007/131109    11/2007

OTHER PUBLICATIONS

International Search Report and Written Opinion for PCT/US15/043582, mailed on Oct. 16, 2015, 5 pages.
(Continued)

*Primary Examiner* — Katherine M Shi
(74) *Attorney, Agent, or Firm* — Haynes and Boone, LLP

(57) ABSTRACT

The present disclosure describes a labor assistance system comprising a perianal support member and grip. The perianal support member includes a contact surface, an inner surface opposing the contact surface, and a rigid compression element. The contact surface has a generally continuous compression surface apex extending from the contact surface in a first direction, oriented to extend from an anterior edge to a posterior edge along a midline axis in a sagittal plane of the patient without substantially interfering with the birthing canal of the patient. The grip is coupled to the inner surface between the anterior edge and the posterior edge of the support member. The present disclosure also describes an intrapartum pelvic floor support device that is applied to tissue in the perianal and/or anococcygeal regions of the patient during an intrapartum period to support the anococcygeal region tissues and at least a portion of the pelvic floor.

11 Claims, 51 Drawing Sheets

Related U.S. Application Data continuation of application No. 16/148,732, filed on Oct. 1, 2018, now Pat. No. 11,389,197, which is a continuation of application No. 14/817,959, filed on Aug. 4, 2015, now Pat. No. 10,085,770.

(60) Provisional application No. 62/086,634, filed on Dec. 2, 2014, provisional application No. 62/033,038, filed on Aug. 4, 2014.

(56) References Cited

U.S. PATENT DOCUMENTS

| | | |
|---|---|---|
| 4,557,260 A | 12/1985 | Reyes, Jr. |
| 4,946,404 A | 8/1990 | Takenouchi et al. |
| 5,360,422 A | 11/1994 | Brownlee |
| 5,577,779 A | 11/1996 | Dangel |
| 5,871,499 A | 2/1999 | Hahn et al. |
| 7,673,633 B2 | 3/2010 | Blurton et al. |
| 8,123,760 B2 | 2/2012 | Blurton |
| 8,597,306 B1 | 12/2013 | Blurton et al. |
| 8,684,954 B1 | 4/2014 | Blurton et al. |
| 2001/0003157 A1* | 6/2001 | Toth .............. A61F 5/0093 604/385.03 |
| 2002/0167206 A1 | 11/2002 | Jalkanen |
| 2007/0031466 A1 | 2/2007 | Blurton |
| 2007/0260163 A1 | 11/2007 | Blurton |
| 2008/0202505 A1 | 8/2008 | Blurton et al. |
| 2011/0022056 A1 | 1/2011 | Haadem |
| 2014/0190488 A1 | 7/2014 | Robran |
| 2014/0257027 A1 | 9/2014 | Palmisano et al. |

OTHER PUBLICATIONS

European Office Action dated Jul. 25, 2016 for European Patent Application No. 06788889.1; 4 pp.

* cited by examiner

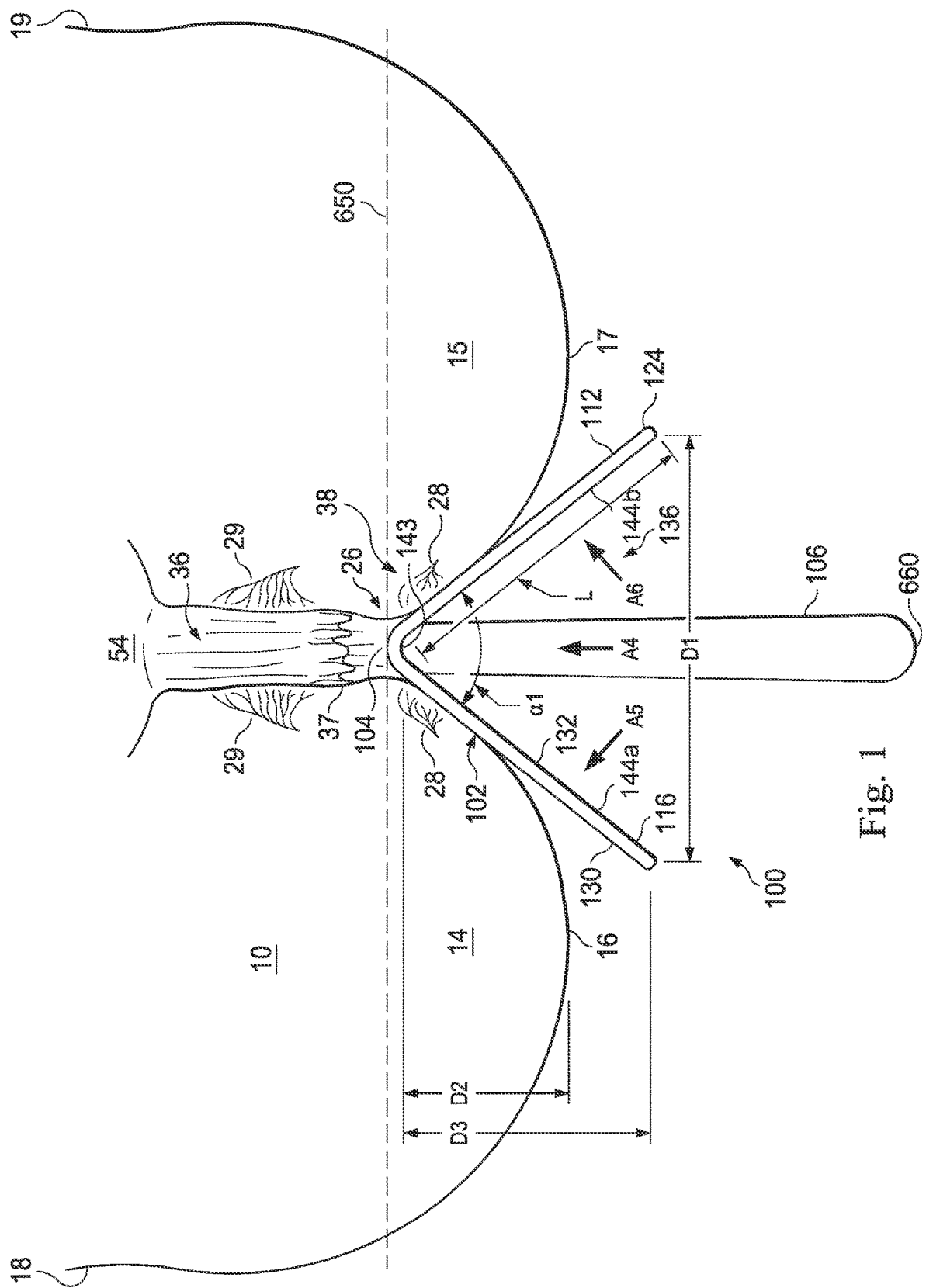

Fig. 16B

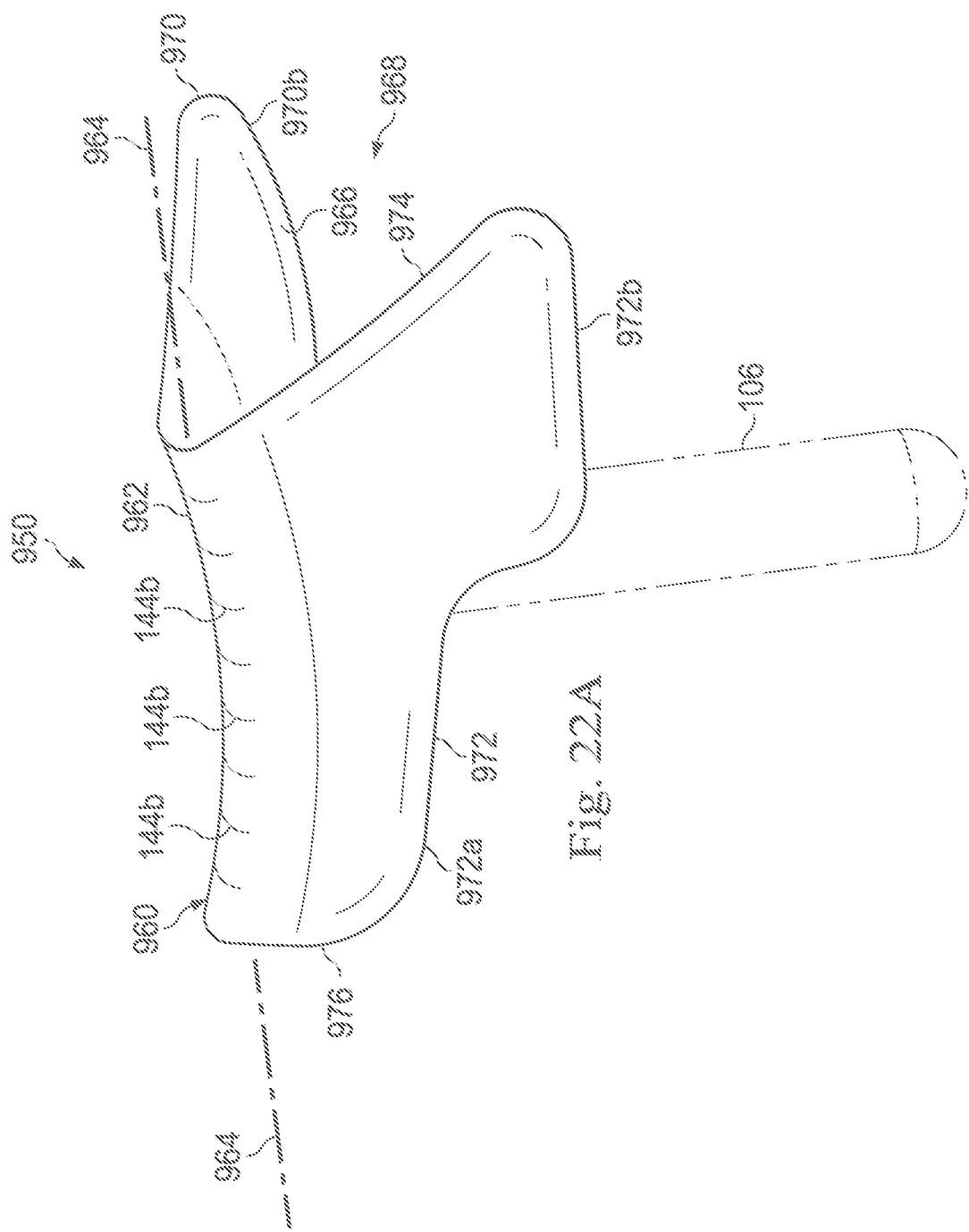

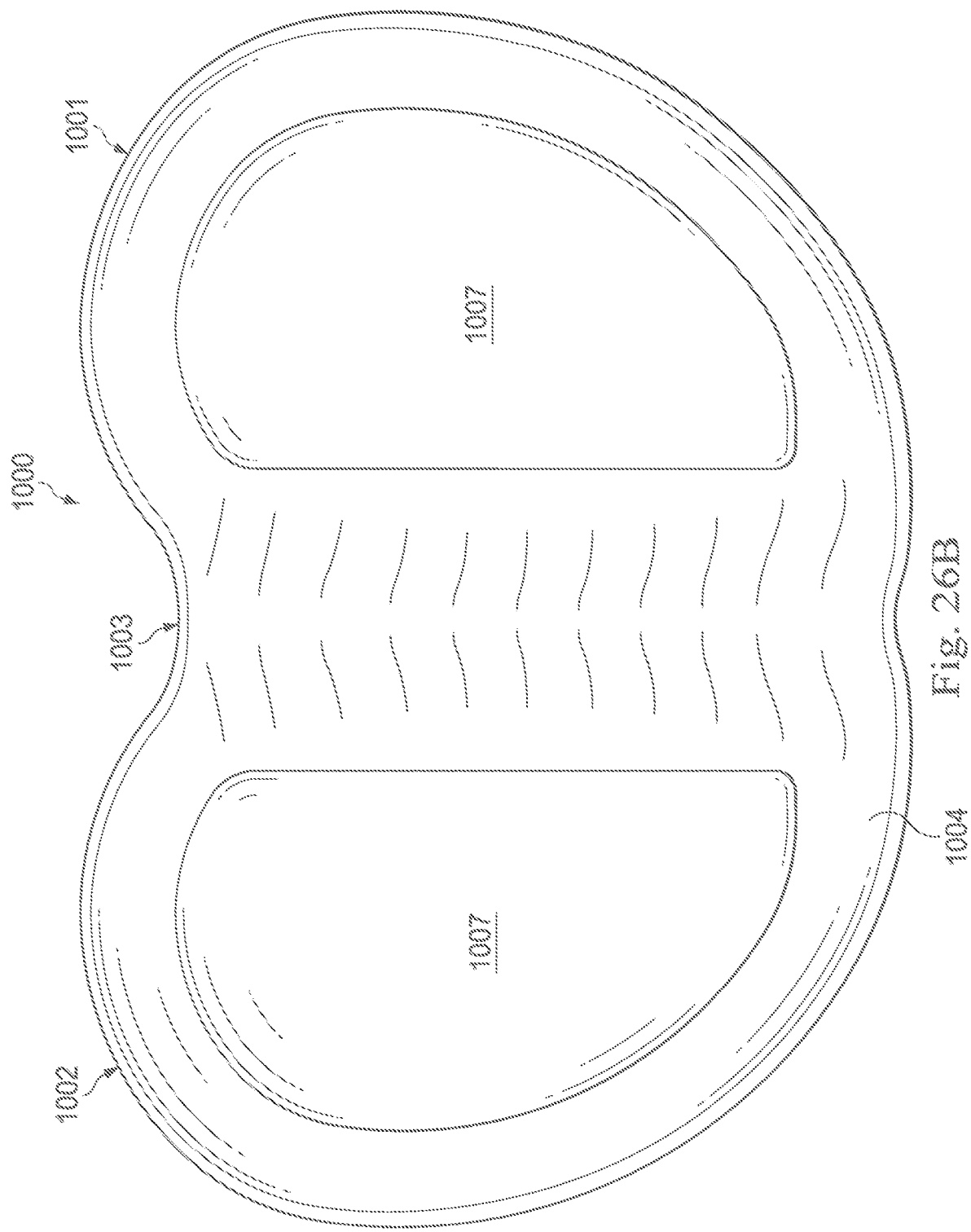

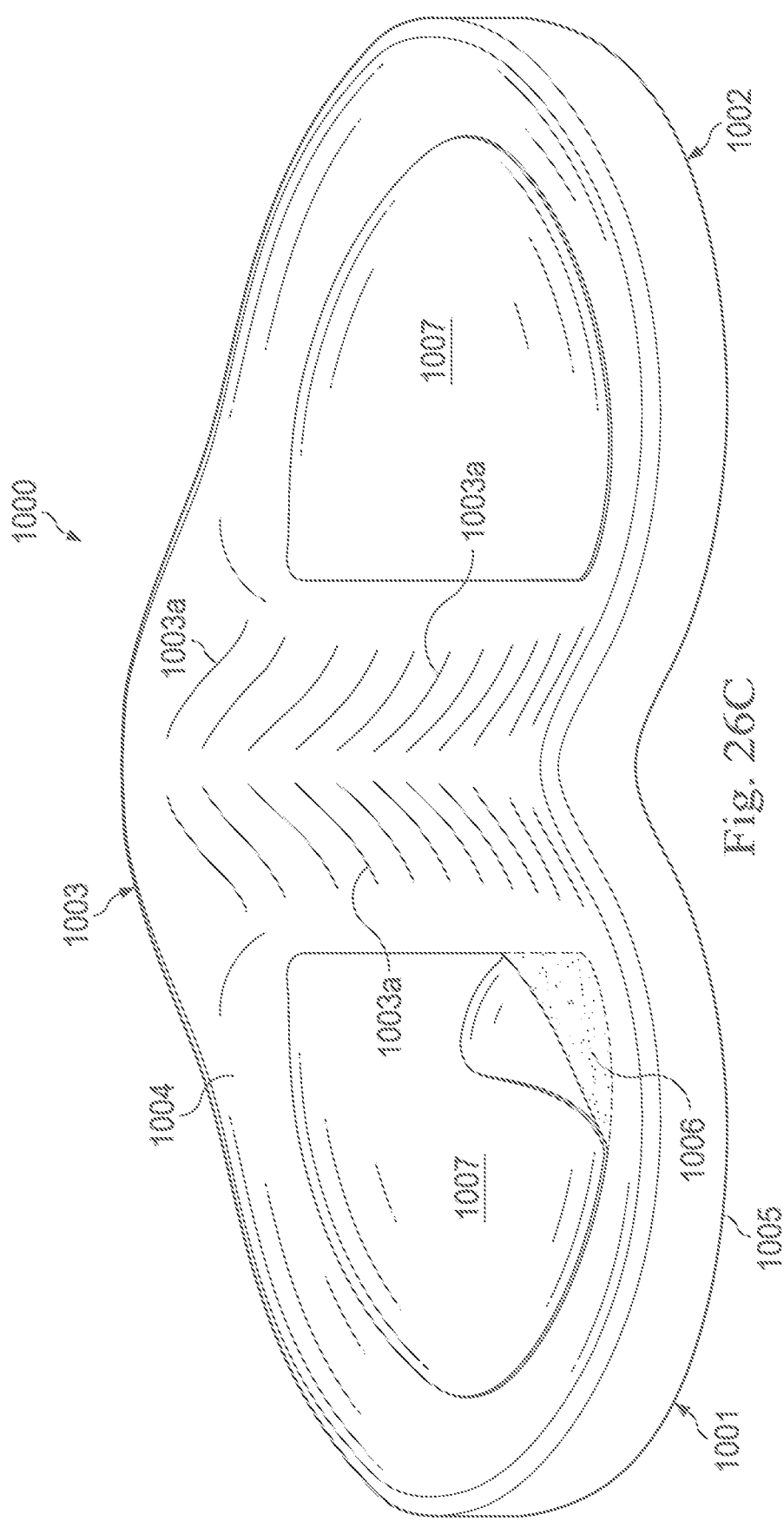

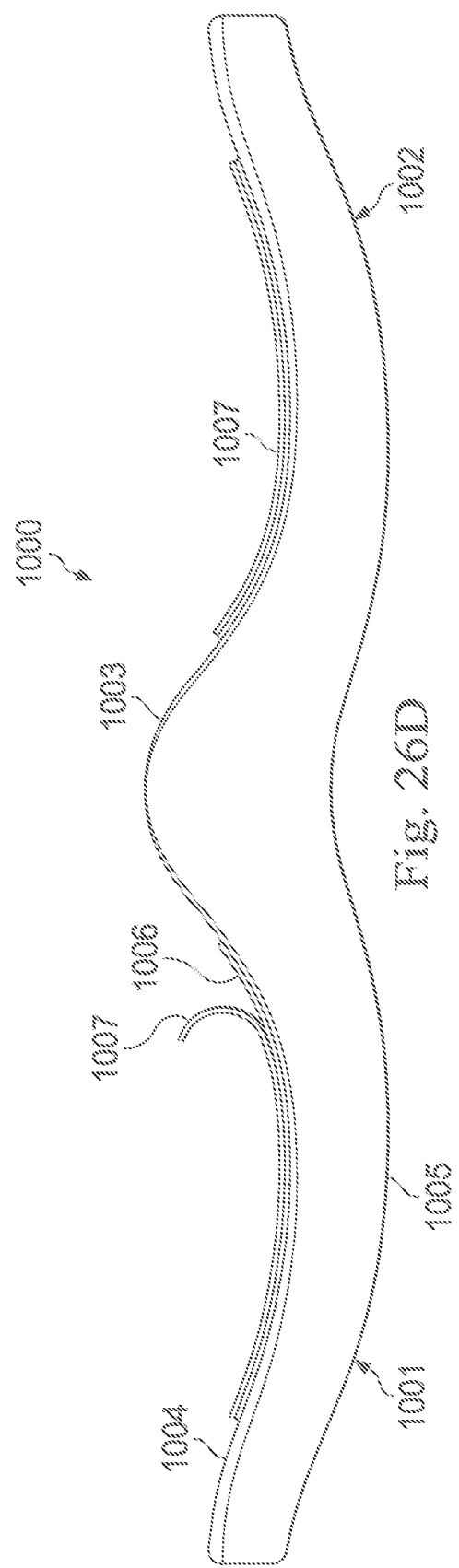

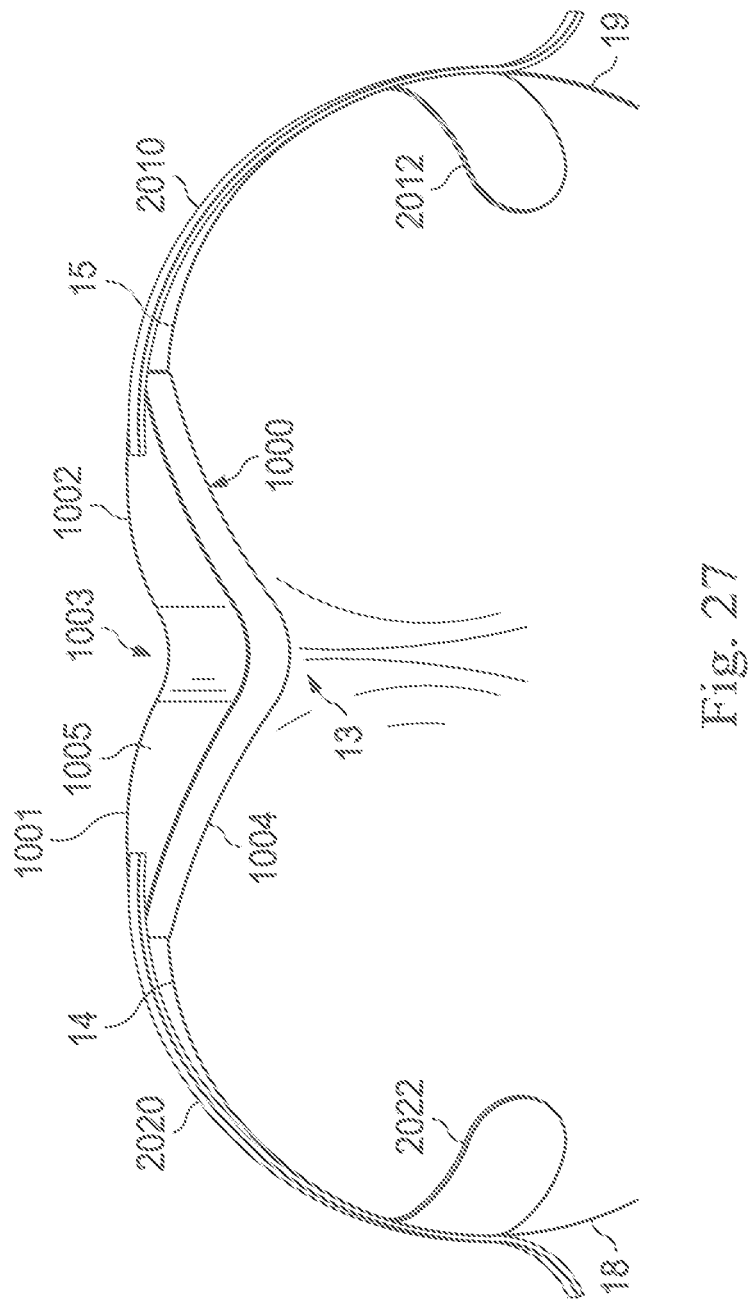

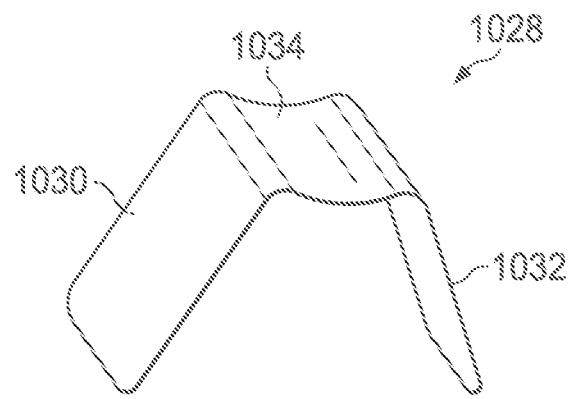
Fig. 34B
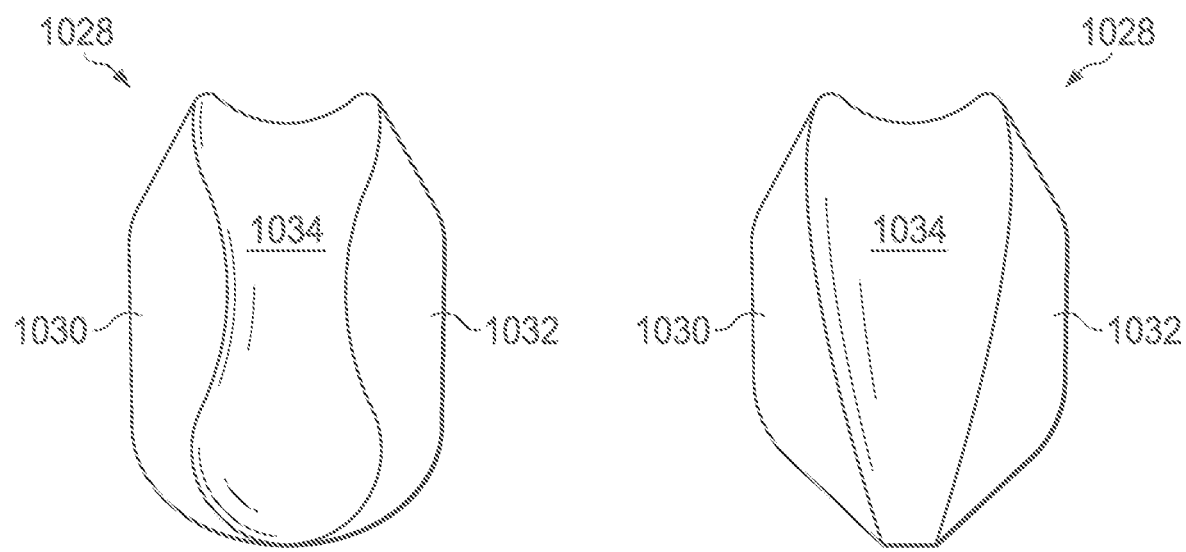
Fig. 34C
Fig. 34D

EXTERNALLY APPLIED INTRAPARTUM SUPPORT DEVICE

PRIORITY DATA

This application is a continuation of U.S. application Ser. No. 17/542,012, filed Dec. 3, 2021, now U.S. Pat. No. 11,510,699, which is a continuation application of U.S. application Ser. No. 16/148,732 filed Oct. 1, 2018, now U.S. Pat. No. 11,389,187, which is a continuation of U.S. application Ser. No. 14/817,959 filed Aug. 4, 2015, now U.S. Pat. No. 10,085,770, which claims priority to and the benefit of the filing date of U.S. Provisional Application No. 62/033,038 filed Aug. 4, 2014, titled "Devices for Assisting the Progression of Labor During Childbirth," and U.S. Provisional Application No. 62/086,634 filed Dec. 2, 2014, titled "Externally Applied Intrapartum Pelvic Floor Support Device," each of which is incorporated herein by reference in their entireties.

BACKGROUND

A typical labor process during childbirth is divided into three stages. The first and second stages are directly involved in the delivery of the child, and the third stage involves the delivery of the placenta. The first stage of labor begins with the onset of rhythmic uterine contractions and ends with complete cervical dilatation. The second stage of labor begins upon complete cervical dilatation and ends after the birth of the child. The third stage of labor extends from the birth of the child to the complete delivery of the placenta. The labor progress, especially through the second stage of labor, is driven by two types of labor forces. The primary force is produced by the involuntary contractions of the mother's uterus (i.e., uterine muscle contractions). The secondary force is produced by the increase of intra-abdominal pressure created by voluntary contractions of the mother's abdominal muscles, including pelvic musculatures and diaphragm. These forces act synergistically to increase the intrauterine pressure and aid the expulsion of the child from the uterus.

The use of epidurals and pain relieving drugs during the labor and delivery process can desensitize the birthing mother from experiencing the natural body signals needed to push the baby through the birth canal and thereby ultimately delay the progression of childbirth. One indication of this phenomenon is that in recent years, there has been a dramatic increase in the incidence of children born by Cesarean childbirth. This form of child birth significantly increases the cost to the healthcare system when compared to a natural vaginal delivery. In addition, the birthing mother needs significantly more time to recover from a Cesarean operation compared to a natural vaginal child delivery. Systemic analgesic drugs, epidural anesthesia, and the long duration of exhaustive labor all can lead to the weakening of the secondary force, and sequentially to delayed labor duration or even dystocia (arrest of labor). Thus, in some instances, the duration of the second stage of labor is prolonged by ineffective or inadequate pushing by the mother, which can lead to injuries of the pelvic floor, fetal distress, higher rate of infant mortality, neonatal seizures, postpartum hemorrhage, and/or to delivery by Cesarean section.

While prior apparatus and methods like those disclosed in U.S. Patent Application Publications 2007/0031466 and U.S. Pat. No. 7,673,633 provide stable support for the soft perianal tissues near the anal orifice, these can be further improved to provide additional benefits for labor management to increase intrauterine pressure (e.g., by strengthening contractions and pushing), thereby decreasing the duration of the second stage of labor and/or decreasing the incidence of Cesarean childbirth. More specifically, there exists a need for devices that permit a healthcare provider to actively and intermittently monitor and guide the labor process to promote more effective fetal descent, thereby decreasing the duration of the second stage of labor and increasing the likelihood of successful vaginal births.

The devices and methods described herein overcome one or more deficiencies of the prior art.

SUMMARY

The present disclosure provides a device for assisting in the progression of labor during childbirth. In one aspect, the device includes a working end with a pressure surface or contact surface configured for spanning the anal orifice and a grip joined to the working end. In one form, the device comprises a V-shaped contact surface coupled to an elongate handle or grip. In a further form, the working end includes an inner surface opposing the contact surface, and the grip is coupled to the opposing inner surface. The grip can be attached to the working end at an adjustable angle by a pivoting assembly, at a fixed angle, or via a detachable connection.

In one embodiment, the working end includes compression members extending outwardly from the contact surface. The compression members extend equal lengths from the contact surface or may alternatively each extend a different length from the contact surface. In one aspect, the compression members each include a longer portion and a shorter portion.

In another embodiment, the working end comprises a V-shaped or U-shaped contact surface. However, it will be appreciated that the working end can include a flat contact surface. In one form, the working end includes a transparent body and contact surface with the transparent body and/or contact surface including markings. In one aspect, the markings may assist a user in positioning the device on the patient. In another aspect, the markings may assist the user in measuring the tissue distention against the contact surface through changing pressure situations during labor. In a further form of the device, the working end includes a transparent window extending through the contact surface.

In a further embodiment of the device, the working end includes a pad coupled to the contact surface. As set forth in the following description, the pad is compliant and may be conformable to the patient's body. In one aspect, the pad is adjustable to have a desired turgidity or degree of conformability. In another aspect, the pad is inflatable with a variety of fluids to have a desired turgidity or degree of conformability. The pad may be configured to retain its shape after the application of pressure.

In yet a further embodiment of a labor assist device, the working end of the device includes a focal protrusion extending outwardly from the contact surface. In one aspect, the focal protrusion is positioned off-center on the contact surface. In another aspect, the focal protrusion may be configured for partial or complete insertion into the anal orifice of the patient.

In a further feature, the grip comprises a T-bar handle coupled to the inner surface of the working end. The T-bar handle can include apertures configured to receive a user's fingers. In an alternative form, the grip comprises a knob-like or tab-like handle. The tab-like handle can include an aperture or depression. In still a further form, the grip comprises a tube-like passageway coupled to the inner surface of the working end. In one aspect, the working end includes a channel that extends from an anterior edge to a posterior edge of the device and aligns with the midline axis of the working end. In yet a further form, the grip comprises a curved support structure or compliant pad coupled to the inner surface of the working end.

In another aspect, the device includes a haptic feedback generator. The haptic feedback generator may be responsive to pressure applied to the contact surface. In one form, the haptic feedback generator causes movement of the working end, while in another, the haptic feedback generator causes movement of the grip.

In still a further aspect, the device includes a push evaluation system coupled to the grip and including an apparatus configured to measure the extent of displacement of the contact surface from the second position during a push.

In a further feature, the present disclosure is directed to a labor assistance system for contact with external perianal tissue of a patient with the system comprising a perianal support member and a grip. In one aspect, the perianal support member includes a contact surface, an inner surface opposing the contact surface, and a rigid compression element. The contact surface may include a continuous compression surface apex extending from the contact surface in a first direction corresponding to a height of the apex. In one form, the contact surface is dimensioned to span across an anal orifice without entering the anal canal for engagement with at least a portion of the external perianal tissue on opposing sides of the anal orifice of the patient. In a further form, the contact surface is oriented to extend from an anterior edge to a posterior edge along a midline axis in a sagittal plane of the patient, and the contact surface anatomically configured to not substantially interfere with the birthing canal of the patient during childbirth. The rigid compression element has a proximal end portion and a distal end portion, with the compression element being operatively joined to the contact surface adjacent the distal end portion and extending therefrom in a second direction to the proximal end portion. In one form, the second direction is generally transverse to the midline axis. The compression element may be configured to transmit compressive force applied adjacent the proximal portion to the contact surface. In one aspect, the grip is coupled to the inner surface between the anterior edge and the posterior edge. The grip can extend from the inner surface in a third direction away from the contact surface. As described in more detail in the following, the grip is shaped and configured for grasping by a user to position and hold the perianal support member against the perianal tissue of the patient.

In one embodiment, the present disclosure provides for a labor assistance system for contact with external perianal tissue of a patient, comprising a perianal support member including: a contact surface, an inner surface opposing the contact surface, a compression element, and a grip. In one aspect, the contact surface has a continuous compression surface apex extending from the contact surface in a first direction corresponding to a height of the apex, the contact surface dimensioned to span across an anal orifice without entering the anal canal for engagement with at least a portion of the external perianal tissue on opposing sides of the anal orifice of the patient, the contact surface oriented to extend from an anterior edge to a posterior edge along a midline axis in a sagittal plane of the patient, the contact surface anatomically configured to not substantially interfere with the birthing canal of the patient during childbirth. In one aspect, the compression element has a proximal end portion and a distal end portion, the compression element operatively joined to the contact surface adjacent the distal end portion and extending therefrom in a second direction to the proximal end portion, the second direction generally transverse to the midline axis, the compression element configured to transmit compressive force applied adjacent the proximal portion to the contact surface. In one aspect, the grip is coupled to the inner surface between the anterior edge and the posterior edge and extending from the inner surface in a third direction away from the contact surface, and the grip is shaped and configured for grasping by a user to position and hold the perianal support member against the perianal tissue of the patient.

In one aspect, further including at least a second compression element joined to the contact surface. In one aspect, the second compression element extends in a fourth direction substantially transverse to the midline axis and at an angle with respect to the second direction. In one aspect, the angle is between 130 and 30 degrees. In one aspect, the angle is between 100 and 70 degrees. In one aspect, the first compression element, the inner surface, and the second compression element meet to define an access cavity. In one aspect, the grip extends through the access cavity between the first and second compression elements. In one aspect, the grip extends from the inner surface at an oblique angle with respect to the midline axis. In one aspect, the grip extends from the inner surface at a transverse angle with respect to the midline axis.

In one aspect, the grip is coupled to the inner surface via a pivot element. In one aspect, the grip extends from the inner surface at a dynamic angle with respect to the midline axis. In one aspect, the pivot element includes a locking feature configured to releasably lock the grip at a fixed angle with respect to the midline axis. In one aspect, the pivot element is spaced a distance apart from the contact surface. In one aspect, the grip extends from the inner surface at a fixed angle with respect to the midline axis.

In one aspect, the perianal support member includes a first height extending from the proximal end portion of the compression element to the apex, the grip includes a second height extending from a proximal end to a distal end of the grip, and the first height is less than the second height. In one aspect, the perianal support member includes a first height extending from the proximal end portion of the compression element to the apex, the grip includes a second height extending from a proximal end to a distal end of the grip, and the first height is greater than the second height.

In one aspect, the perianal support member includes a curved, convex contact surface and a curved compression element having the same radius of curvature as the contact surface. In one aspect, the perianal support member includes a substantially flat, planar contact surface.

In one aspect, the perianal support member includes a pressure element disposed on the contact surface, the pressure element extending from the contact surface in the first direction. In one aspect, the pressure element comprises a protrusion shaped and configured to apply a focal area of increased pressure upon the external perianal tissue of the patient. In one aspect, the pressure element is positioned on the contact surface closer to the anterior edge than the posterior edge.

In one aspect, the contact surface includes a visual indicator configured be aligned with a body reference marker to assist the user in positioning the perianal support member against the patient.

In one aspect, the anterior edge of the perianal support member includes a concave portion alignable with the vaginal orifice of the patient.

In one aspect, the perianal support member includes a compliant pad disposed on the contact surface. In one aspect, the compliant pad includes a treating compound.

In one aspect, the grip comprises an elongated shaft terminating in a crossbar configured to form a grasping handle for the user. In one aspect, the grip comprises an elongate shaft terminating at a knob configured to form a grasping handle for the user. In one aspect, the grip comprises an elongate shaft terminating in a tab configured to form a grasping handle for the user. In one aspect, the tab forms an annular ring. In one aspect, the grip comprises a hollow tube coupled to the inner surface and extending parallel to the midline axis. In one aspect, the grip comprises a channel formed within the perianal support member, the channel extending from the anterior edge to the posterior edge of the perianal support member. In one aspect, the grip comprises a curved support structure including an upper surface having substantially the same shape and contour as the inner surface of the perianal support member, the upper surface being in contact with the inner surface.

In one aspect, the system further comprises a push evaluation system configured to measure the strength of the patient's pushes, the push evaluation system including a spring-loaded device coupled to the grip. In one aspect, the spring-loaded device comprises a spring coupled to the grip, a securing member extending from the spring and coupled to an anchor pad, the anchor pad including an adhesive portion configured to adhere to the patient.

In one aspect, the grip includes markings spaced relative to the securing member such that the position of the markings relative to the securing member indicates the degree of displacement of the perianal support device during a patient's push. In one aspect, the perianal support member is formed of a substantially clear material. In one aspect, the perianal support member includes a plurality of measurement markers. In one aspect, the compression element includes a short portion defining a posterior edge and a long portion defining an anterior edge of the perianal support member.

In one aspect, at least a portion of the perianal support member is shaped and configured to conform to superficial contours of a pelvic floor and apply pressure against an anococcygeal region of the patient. In one aspect, at least a portion of the perianal support member is sufficiently rigid to apply pressure against an anococcygeal region of the patient.

The present disclosure is, at least in part, directed to a method of providing a laboring patient with a focal point against which to push. In one aspect, the method comprises providing a labor assistance system having a perianal support member including a contact surface configured for engaging the pelvic floor area of the patient and a grip coupled to the perianal support member and configured for a user to grasp. The method includes maneuvering the grip to position the contact surface in a first position in contact with skin adjacent the posterior pelvic floor area of the patient. The method also includes applying pressure through the grip to the perianal support member to direct pressure through the contact surface against skin and into the pelvic floor area of the patient, wherein applying pressure includes pushing the grip toward the patient during a uterine contraction and moving the contact surface to a second position.

In one aspect, the method includes: providing a labor assistance system having a pelvic floor support member including a contact surface configured for engaging the perianal area of the patient and; maneuvering the pelvic floor support member to position the contact surface in a first position in contact with the perianal area of the patient; and applying pressure to the pelvic floor support member to direct pressure through the contact surface against the perianal area of the patient during a uterine contraction.

In one aspect, the method further comprises maintaining the position of the pelvic floor support member against the perianal tissue throughout the duration of a uterine contraction. In one aspect, the method further comprises increasing the pressure applied through the contact surface against the perianal tissue as the uterine contraction gains strength. In one aspect, the method further comprises decreasing the pressure applied through the contact surface against the perianal tissue as the uterine contraction loses strength. In one aspect, the method further comprises observing the strength of a push from the patient by measuring the extent of displacement of the contact surface from the first position to a second position during a push.

In one aspect, the method further comprises a labor assistance system including a push evaluation system coupled to the pelvic floor support member and including a spring-loaded device configured to measure the extent of displacement of the contact surface from the first position to the second position during a push. In one aspect, wherein applying pressure to the pelvic floor support member to direct pressure through the contact surface against the perianal area of the patient includes pushing a grip coupled to the pelvic floor support member toward the patient during a uterine contraction.

In still a further aspect, the present disclosure is directed to a method of guiding a baby through a birth canal to a vaginal orifice during childbirth. The method includes positioning a labor assistance system in contact with at least a portion of the skin overlying the posterior pelvic floor of the patient prior to delivery of the baby, and the labor assistance system includes a grip extending from a perianal support member having a contact surface configured to engage the perianal tissue. In one aspect, the method includes positioning the contact surface against at least a portion of perianal skin such that the contact surface operates as a sacral extension member and provides external scaffolding to support the anococcygeal region tissue and the posterior pelvic floor as well as to guide the baby through the birth canal extending through the anterior pelvic floor. In another aspect, the method includes directing pressure through the grip toward the contact surface against the perianal tissue in a direction configured to guide the baby toward the vaginal orifice.

In one aspect, the method includes: positioning a labor assistance system in contact with at least a portion of the anococcygeal region of the patient prior to delivery of the baby, the labor assistance system including a perianal support member having a contact surface configured to engage the anococcygeal region; positioning the contact surface against at least a portion of anococcygeal region such that the contact surface operates as a sacral extension member and provides external scaffolding to support at least a portion of the posterior pelvic floor to thereby guide the baby toward the birth canal; and directing pressure through the contact surface against the anococcygeal region in a direction configured to guide the baby toward the vaginal orifice.

In one aspect, the method further comprises changing the position of the contact surface relative to the perianal tissue as the baby descends through the birth canal. In one aspect, the method further comprises changing the direction of pressure applied through the grip toward the contact surface against the perianal tissue to guide the baby toward the vaginal orifice as the baby descends through the birth canal. In one aspect, directing pressure through the contact surface against the anococcygeal tissue comprises directing pressure through a grip extending from the perianal support member toward the contact surface.

In a further embodiment, the present disclosure is directed to a method of monitoring pressure in the pelvic tissues to assess the progression of labor in a patient. The method includes positioning a labor assistance system in contact with at least a portion of the pelvic tissues of the patient prior to delivery of a baby, and the labor assistance system includes a grip extending from a perianal support member having a contact surface configured to engage the pelvic tissue. In one aspect, the method includes positioning the contact surface against at least a portion of pelvic tissue such that pelvic tissue engages the contact surface across a first area. In a further aspect, the method includes observing the spread of the pelvic tissue across a second area of the contact surface as the pressure changes against the contact surface.

In one aspect, the method comprises: positioning a labor assistance system in contact with at least a portion of the perianal tissues of the patient prior to delivery of a baby, the labor assistance system including a grip extending from a perianal support member having a contact surface configured to engage the perianal tissue; positioning the contact surface against at least a portion of perianal tissue such that perianal tissue engages the contact surface across a first area; and observing the spread of the perianal tissue across a second area of the contact surface as the pressure changes against the contact surface. In one aspect, the method further comprises comparing the first area to the second area to measure the change in tissue distension as the pressure changes against the contact surface. In one aspect, the method further comprises measuring the first area and the second area by observing the engagement of perianal tissue with the contact surface relative to markings on the perianal support member.

The present disclosure also provides a non-invasive device for supporting the pelvic floor during an intrapartum period. In one aspect, the device includes a central support element having a contact surface configured to be held against and extend from an anterior portion posterior to a vaginal opening of a patient to a posterior portion of the patient that is posterior to an anal orifice of the patient. A first support element extends from the central support element in a first lateral direction, the first support element comprising a first concave inner surface to receive a first buttock of the patient and a first convex outer surface. A second support element extends from the central support element in a second lateral direction opposite to the first lateral direction, the second support element comprising a second concave inner surface to receive a second buttock of the patient and a second convex outer surface. The non-invasive intrapartum pelvic floor support device is held against superficial tissue superior to the pelvic floor of the patient to support the pelvic floor during an intrapartum period of the patient. In one aspect, the device comprises a central support element having a contact surface configured to be held against and extend from an anterior portion posterior to a vaginal opening of a patient to a posterior portion of the patient that is posterior to an anal orifice of the patient; a first support element extending from the central support element in a first lateral direction, the first support element comprising a first concave inner surface to receive a first buttock of the patient; and a second support element extending from the central support element in a second lateral direction opposite to the first lateral direction, the second support element comprising a second concave inner surface to receive a second buttock of the patient, wherein the non-invasive intrapartum pelvic floor support device is held against tissue superficial to the pelvic floor of the patient to support the pelvic floor during an intrapartum period of the patient.

In one aspect, the non-invasive intrapartum pelvic floor support device is held against the tissue superficial to the pelvic floor with an adhesive between an inner surface of the non-invasive intrapartum pelvic floor support device and skin of the patient. In one aspect, the inner surface comprises the first and second concave inner surfaces.

In another embodiment, the non-invasive intrapartum pelvic floor support device includes a central support element having a contact surface configured to be held against and extend from an anterior portion posterior to a vaginal opening of a patient to a posterior portion of the patient that is posterior to an anal orifice of the patient, the central support element comprising a concave inner surface facing the patient and a convex outer surface. A first support element extends from the central support element in a first lateral direction. A second support element extends from the central support element in a second lateral direction opposite to the first lateral direction. The non-invasive intrapartum pelvic floor support device is held against superficial tissue superior to the pelvic floor of the patient to support the pelvic floor during an intrapartum period of the patient.

In one aspect, the device comprises a central support element having a contact surface configured to be held against and extend from an anterior portion posterior to a vaginal opening of a patient to a posterior portion of the patient that is posterior to an anal orifice of the patient, the central support element comprising a concave inner surface facing the patient and a convex outer surface; a first support element extending from the central support element in a first lateral direction; and a second support element extending from the central support element in a second lateral direction opposite to the first lateral direction, wherein the non-invasive intrapartum pelvic floor support device is held against tissue superficial to the pelvic floor of the patient to support the pelvic floor during an intrapartum period of the patient.

In one aspect, an anterior portion of the first support element and an anterior portion of the second support element extend in an anterior direction beyond an anterior portion of the central support element to define a recess at the central support element to allow access to the vaginal opening.

In one aspect, a lateral width of the central support element varies along the contact surface between an anterior portion and a posterior portion of the non-invasive intrapartum pelvic floor support device.

In another embodiment, a support system includes the non-invasive intrapartum pelvic floor support device comprising a central support element having a contact surface configured to be held against and extend from an anterior portion posterior to a vaginal opening of a patient to a posterior portion of the patient that is posterior to an anal orifice of the patient along a midline axis in a sagittal plane of the patient. The non-invasive intrapartum pelvic floor support device also includes a first support element extending from the central support element in a first lateral direction and a second support element extending from the central support element in a second lateral direction opposite to the first lateral direction. The support system also includes a perianal support member including a contact surface dimensioned to span across an anal orifice without entering an anal canal for engagement with at least a portion of external perianal tissue on opposing sides of the anal orifice of the patient, the contact surface oriented to extend from an anterior edge to a posterior edge along a midline axis in a sagittal plane of the patient. An inner surface of the perianal support member opposes the contact surface. A compression element of the perianal support member has a proximal end portion and a distal end portion, the compression element operatively joined to the contact surface adjacent the distal end portion and extending therefrom in a second direction to the proximal end portion, the second direction generally transverse to the midline axis, the compression element configured to transmit compressive force applied adjacent the proximal portion to the contact surface. The non-invasive intrapartum pelvic floor support is configured to receive the perianal support member along the midline axis during an intrapartum period of the patient.

In one aspect, the support system comprises a non-invasive intrapartum pelvic floor support comprising: a central support element having a contact surface configured to be held against and extend from an anterior portion posterior to a vaginal opening of a patient to a posterior portion of the patient that is posterior to an anal orifice of the patient along a midline axis in a sagittal plane of the patient; a first support element extending from the central support element in a first lateral direction; and a second support element extending from the central support element in a second lateral direction opposite to the first lateral direction; and a perianal support member. In one aspect, the perianal support member includes a contact surface dimensioned to span across an anal orifice without entering an anal canal for engagement with at least a portion of external perianal tissue on opposing sides of the anal orifice of the patient, the contact surface oriented to extend from an anterior edge to a posterior edge along a midline axis in a sagittal plane of the patient; an inner surface opposing the contact surface; and a compression element having a proximal end portion and a distal end portion, the compression element operatively joined to the contact surface adjacent the distal end portion and extending therefrom in a second direction to the proximal end portion, the second direction generally transverse to the midline axis, the compression element configured to transmit compressive force applied adjacent the proximal portion to the contact surface. In one aspect, the non-invasive intrapartum pelvic floor support is configured to receive the perianal support member along the midline axis during an intrapartum period of the patient.

In one aspect, the non-invasive intrapartum pelvic floor support further comprises a gap along the central support element and a first part of a locking mechanism, and the perianal support member further comprises a second part of the locking mechanism, the second part being configured to couple with the first part to operatively join the non-invasive intrapartum pelvic floor support and the perianal support member together.

In one aspect, the perianal support member further comprises an adjustable strap connected between the compression element of the perianal support member an anchor mechanism, the strap configured to increase or decrease pressure to the external perianal tissue in response to tightening or loosening of the strap.

In another embodiment, the non-invasive intrapartum pelvic floor support device includes a flexible anterior support structure having a first rigidity for supporting a pelvic floor of a patient, the flexible anterior support structure extending along a midline axis of the patient from an anterior portion that is posterior to a vaginal opening of the patient to a posterior portion of the patient that is posterior to an anal orifice of the patient, and in a first lateral direction toward a first buttocks of the patient and a second lateral direction toward a second buttocks of the patient. The non-invasive intrapartum pelvic floor support device also includes a first lateral support structure extending from the flexible anterior support structure around a lateral side of the first buttocks, and a second lateral support structure extending from the flexible anterior support structure around a lateral side of the second buttocks, the first and second lateral support structures having a second rigidity that is less than the first rigidity. The first and second lateral support structures are configured to transfer a load from the flexible anterior support structure.

In one aspect the device comprises: a flexible anterior support structure having a first rigidity for supporting a pelvic floor of a patient, the flexible anterior support structure extending along a midline axis of the patient from an anterior portion that is posterior to a vaginal opening of the patient to a posterior portion of the patient that is posterior to an anal orifice of the patient, and in a first lateral direction toward a first buttocks of the patient and a second lateral direction toward a second buttocks of the patient; a first lateral support structure extending from the flexible anterior support structure around a lateral side of the first buttocks; and a second lateral support structure extending from the flexible anterior support structure around a lateral side of the second buttocks, the first and second lateral support structures having a second rigidity that is less than the first rigidity, wherein the first and second lateral support structures are configured to transfer a load from the flexible anterior support structure.

In one aspect, the flexible anterior support structure comprises a first mesh, the first and second lateral support structures comprise a second mesh, and the first mesh has a higher rigidity than the second mesh. In one aspect, the non-invasive intrapartum pelvic floor support device comprises a material sheet, the flexible anterior support structure comprises a first plurality of ridges along a first portion of the material sheet, and the first and second lateral support structures comprise a second plurality of ridges along a second portion of the material sheet. In one aspect, at least a portion of an interior portion of the non-invasive intrapartum pelvic floor support device facing the patient comprises an adhesive to adhere the between an inner surface of the non-invasive intrapartum pelvic floor support device and skin of the patient to skin of the patient.

In another embodiment, the non-invasive intrapartum pelvic floor support device includes a first contact member configured to attach to a lateral portion of a first buttock of a patient near a first crown of the first buttock. A second contact member is configured to attach to a lateral portion of a second buttock of the patient near a second crown of the second buttock. A joining member is configured to join between the first and second contact members and pull the first and second buttocks laterally inward toward each other to support a pelvic floor of the patient.

In one aspect, the device comprises: a first contact member configured to attach to a lateral portion of a first buttock of a patient near a first crown of the first buttock; a second contact member configured to attach to a lateral portion of a second buttock of the patient near a second crown of the second buttock; and a joining member configured to join between the first and second contact members and pull the first and second buttocks laterally inward toward each other to support tissue superficial to a pelvic floor of the patient.

In one aspect, the joining member comprises a flexible strap attached between the first and second contact members, the first contact member comprises a first adhesive anchor pad configured to releasably adhere to the lateral portion of the first buttock, and the second contact member comprises a second adhesive anchor pad configured to releasably adhere to the lateral portion of the second buttock. In one aspect, the flexible strap comprises an arcuate shape that is concave at an anterior portion and convex at a posterior portion to allow access to a vaginal opening of the patient. In one aspect, the joining member comprises an inflatable support device configured to inflate with a fluid, the inflatable support device comprising the first and second contact members to contact the lateral portions of the first and second buttocks upon at least partial inflation with the fluid.

Further aspects, forms, embodiments, objects, features, benefits, and advantages of the present disclosure shall become apparent from the detailed drawings and descriptions provided herein.

BRIEF DESCRIPTION OF THE DRAWINGS

FIG. 1 illustrates a side view of an exemplary labor assistance system applied to a patient with stylized depiction of the patient anatomy according to one embodiment of the present disclosure.

FIG. 2C illustrates exemplary securing members according to one embodiment of the present disclosure.

FIG. 16B illustrates a similar cross-sectional view of a patient in the sagittal plane and the exemplary labor assistance system shown in FIG. 9A.

FIG. 22A illustrates a perspective view of an exemplary labor assistance system including an exemplary perianal support member according to one embodiment of the present disclosure.

FIG. 26B illustrates a top view of the exemplary intrapartum anococcygeal support device patient shown in FIG. 22A according to one embodiment of the present disclosure.

FIG. 26C illustrates a perspective view of the exemplary intrapartum anococcygeal support device patient shown in FIG. 22A according to one embodiment of the present disclosure.

FIG. 26D illustrates a side view of the exemplary intrapartum anococcygeal support device patient shown in FIG. 22A according to one embodiment of the present disclosure.

FIG. 27 illustrates a rear view of the intrapartum anococcygeal support device shown in FIGS. 26A-27D positioned on a patient according to an embodiment of the present disclosure.

FIG. 34B illustrates an intrapartum pelvic floor support device according to an embodiment of the present disclosure.

FIG. 34C illustrates an intrapartum pelvic floor support device according to an embodiment of the present disclosure.

FIG. 34D illustrates an intrapartum pelvic floor support device according to an embodiment of the present disclosure.

DETAILED DESCRIPTION

Figure 2A:
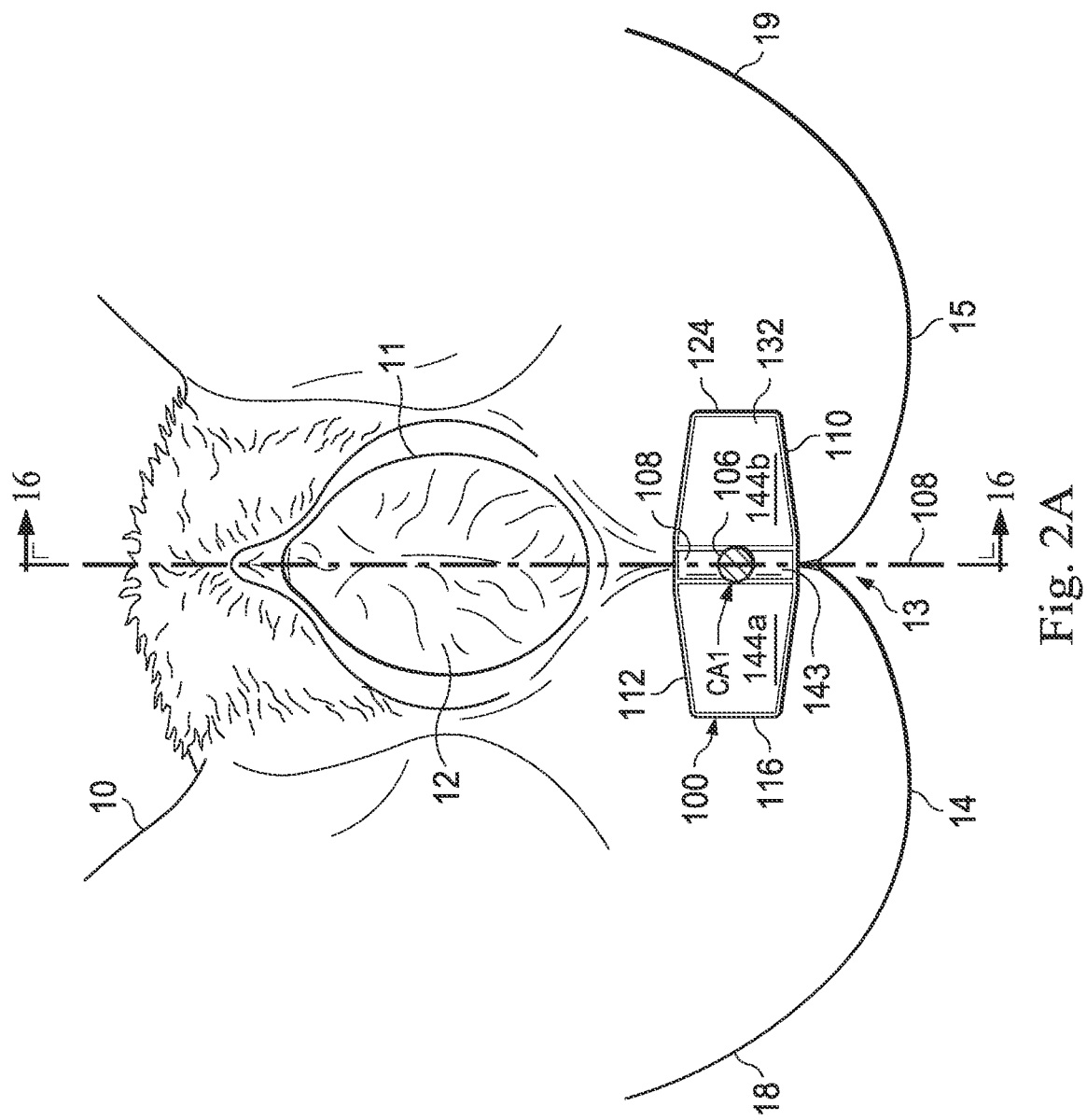
FIG. 2A illustrates a partial perspective bottom view of the labor assistance system shown in FIG. 1 applied to a patient during child delivery.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. The following patents and patent applications are incorporated by reference.

U.S. Pat. No. 8,123,760, filed Aug. 5, 2005, titled "Method, Apparatus and System for Preventing or Reducing the Severity of Hemorrhoids," and commonly assigned to the present applicant, is hereby incorporated by reference in its entirety.

U.S. patent application Ser. No. 11/743,858, filed August May 3, 2007, issued as U.S. Pat. No. 7,673,633,entitled "Apparatus and Method of Inhibiting Perianal Tissue Damage," and commonly assigned to the present applicant, is hereby incorporated by reference in its entirety.

U.S. patent application Ser. No. 12/106,956, filed August Apr. 21, 2008, and published as Patent Application Publication No. 2008/0202505, entitled "Apparatus and Method of Supporting Patient Tissue," and commonly assigned to the present applicant, is hereby incorporated by reference in its entirety.

U.S. Pat. No. 8,684,954, filed Mar. 15, 2013, entitled "Labor Management Devices for Decreasing the Incidence of Cesarean Childbirth," and commonly assigned to the present applicant, is hereby incorporated by reference in its entirety.

U.S. Pat. No. 5,871,499, filed Apr. 25, 1997, titled "Child Birth Assisting System," and assigned to Novatrix, Inc., is hereby incorporated by reference in its entirety.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The present disclosure is directed to systems, devices, and methods for monitoring and assisting the progression of labor during childbirth by providing a qualitative pressure indicator while supporting and/or treating the perianal and anococcygeal tissues of a patient. These labor assistance systems introduce novel elements and methods that may assist the management, progress, and effectiveness of labor along with supporting and/or treating the tissues, muscles, and organs of the pelvic region, including, by way of non-limiting example, the pelvic tissues, muscles, and organs within the anogenital triangle and the anal triangle (e.g., the pelvic diaphragm, the coccygeus muscle and the levator plate), the perianal region, the perineal region, and the anococcygeal region. The embodiments may provide visual and/or tactile feedback to healthcare providers and patients regarding changes in pressure levels due to device application or physiological transformations, such as those that occur with uterine contractions or voluntary contractions during child delivery (including, by way of non-limiting example, changes in uterine, pelvic, rectal, anal, perianal, intrauterine, intrapelvic, intrarectal, and/or intra-anal pressures). Application of pressure in the perianal and anococcygeal regions can be sensed as a tactile sensation by a patient, often even after administration of an epidural and provides a pushing focal point to enhance the effectiveness of contractions. For example, in some instances, the embodiments disclosed herein provide a tactile (and sometimes visual) focal point at the perianal region on which the patient can focus her pushing effort during voluntary muscle contractions. The embodiments described herein provide a qualitative sense to the user and/or the patient of the relative amount of pressure that is being applied to the device by the patient's tissue and/or the relative amount of pressure that is being applied to the patient by the device. Thus, the devices described herein provide an indication (e.g., a tactile, haptic, and/or visual indication) in real time of the change in pressure relationships between the device and the patient as the patient's labor progresses.

In addition, some embodiments may increase the intensity and/or number of intrauterine contractions, thereby shortening the second stage of labor and decreasing the occurrence of various negative effects of a prolonged labor (e.g., injuries of the pelvic floor, fetal distress, higher rate of infant mortality, neonatal seizures, postpartum hemorrhage, and/or to delivery by Cesarean section). In some instances, the embodiments disclosed herein may apply sufficient pressure to the perianal region to stimulate the patient's physiologic urge to push (e.g., similar to the Ferguson reflex, which triggers uterine contractions). These effects may result in a shortening of the second stage of labor by enhancing the effectiveness of contractions (e.g., by increasing the intensity and or number of contractions) in advancing the baby down the birth canal.

In some instances, the labor assistance systems disclosed herein may be used to support the perianal tissue and/or anococcygeal region of a patient during the second stage of labor, which may reduce the incidence of a number of complications and conditions, including, for example, pelvic floor incompetence or dysfunction (over-stretching of pelvic floor muscles, ligaments and tendons), organ prolapse results from the over stretching, incontinence secondary to pressure and stretching exerted on bladder and bladder neck, over-stretching due to use of forceps in delivery, perineum tears and lacerations due to over stretching, vacuum or forceps use, uncontrolled flexion/extension of the fetal head as it descends, and hemorrhoids. The pelvic floor, sometimes referred to as the pelvic diaphragm, is the inferior border of the pelvic cavity defined between the lower openings of the pelvic girdle. The pelvic floor has two hiatuses (gaps or openings): the anterior urogenital hiatus through which the urethra and vagina pass and the posterior rectal hiatus through which the anal canal passes. The pelvic floor facilitates birth by resisting the descent of the presenting part of the baby (i.e., typically the head of the baby), causing the baby to rotate forward to navigate through the pelvic girdle and exit through the vaginal opening in the anterior urogenital hiatus in the pelvic floor (see, for example, FIG. 16A). In particular, the pelvic floor, the sacrum, and the coccyx provide resistance against the downward descent of the baby (along the longitudinal axis of the baby and toward the posterior rectal hiatus) caused by force of the mother's uterine contractions. This passive resistance causes the baby's head to rotate and descend in the direction of least resistance, which is usually in the direction of the midline of the maternal pelvis.

In one aspect, an external labor assist device is provided to apply pressure to and push against the skin of the anococcygeal and/or perianal tissues outside the pelvic floor to thereby support the internal pelvic floor tissues in their function of guiding the baby toward the vaginal opening. Support of the posterior pelvic floor by the devices disclosed herein facilitates the progression of the baby through the birth canal toward the vaginal opening by acting as a type of external scaffolding to lengthen the path of passive resistance that turns and guides the baby towards the vaginal opening. In some instances, the pelvic floor and anococcygeal support provided by the devices disclosed herein facilitate the delivery of the baby with fewer uterine and voluntary contractions for the mother, thereby reducing the overall length of the second stage of labor and reducing injury to the mother (e.g., from the distention of pelvic floor and anal tissues that result from force applied by the baby in the direction of the posterior rectal hiatus).

In some instances, the embodiments disclosed herein provide external birth canal support devices that may be manually repositioned throughout the labor process to effectively channel the mother's pushing force along the appropriate axis to guide the child's head through a desirable exit path from the birth canal. In some instances, the embodiments disclosed herein may cover all or most of the anal orifice, and thereby provide defecation suppression, hemorrhoid development, and/or the advancement of existing hemorrhoids. In some instances, the embodiments disclosed herein enhance the willingness of the patient to push when instructed by lessening the patient's fear of trauma and/or involuntary defecation as a result of pushing.

The labor assistance systems disclosed herein can efficiently, effectively, removably, and safely prevent prolonged duration of labor and dystocia due to various causes, including, without limitation, systemic analgesia, epidural anesthesia, and/or maternal exhaustion, which may avoid a Cesarean section and/or an instrument-assisted delivery. Given that weakening of the secondary labor force has been reported in patients receiving epidural anesthesia, the systems may effectively enable a safer and less painful delivery under anesthesia by preventing weakening of the secondary labor force (e.g., even under anesthesia). Thus, the labor assistance systems disclosed herein may reduce the necessity of Cesarean section deliveries and/or instrument-assisted deliveries by guiding the patient and monitoring (via pressure feedback) the strength and focus of contractions to generate a more effective pushing effect on the baby. By reinforcing the secondary labor force, the labor assistance systems disclosed herein may lower the dosage of oxytocin (or other pharmacological contraction aides) necessary during labor. In some instances, the systems disclosed herein may be used to cooperatively complement the effects of oxytocin during labor.

Figure 2B:
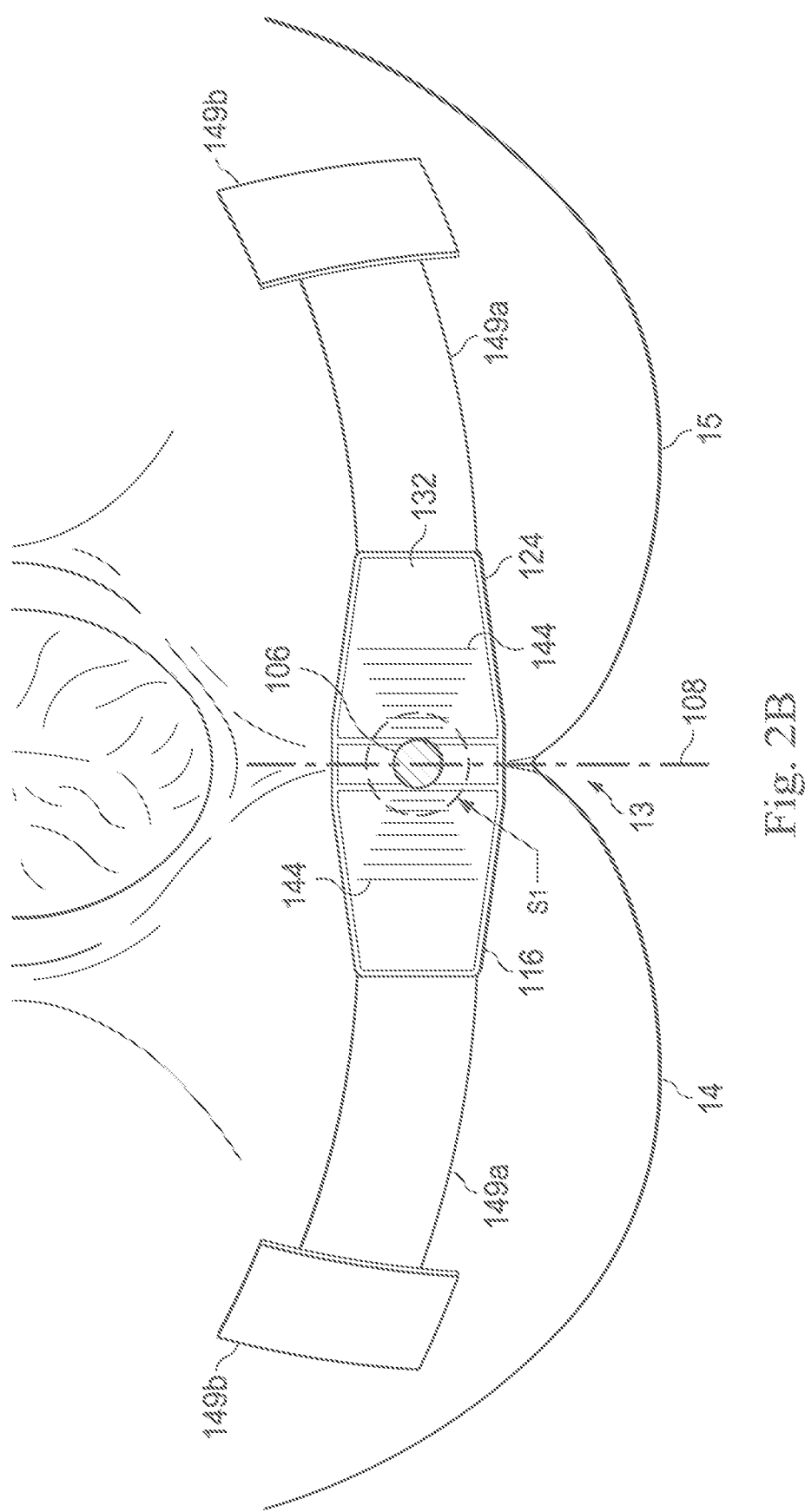
FIGS. 2B and 2C illustrate partial perspective bottom views of an exemplary labor assistance system positioned against a patient during two different pressure situations during child delivery. In addition.
Figure 2C:
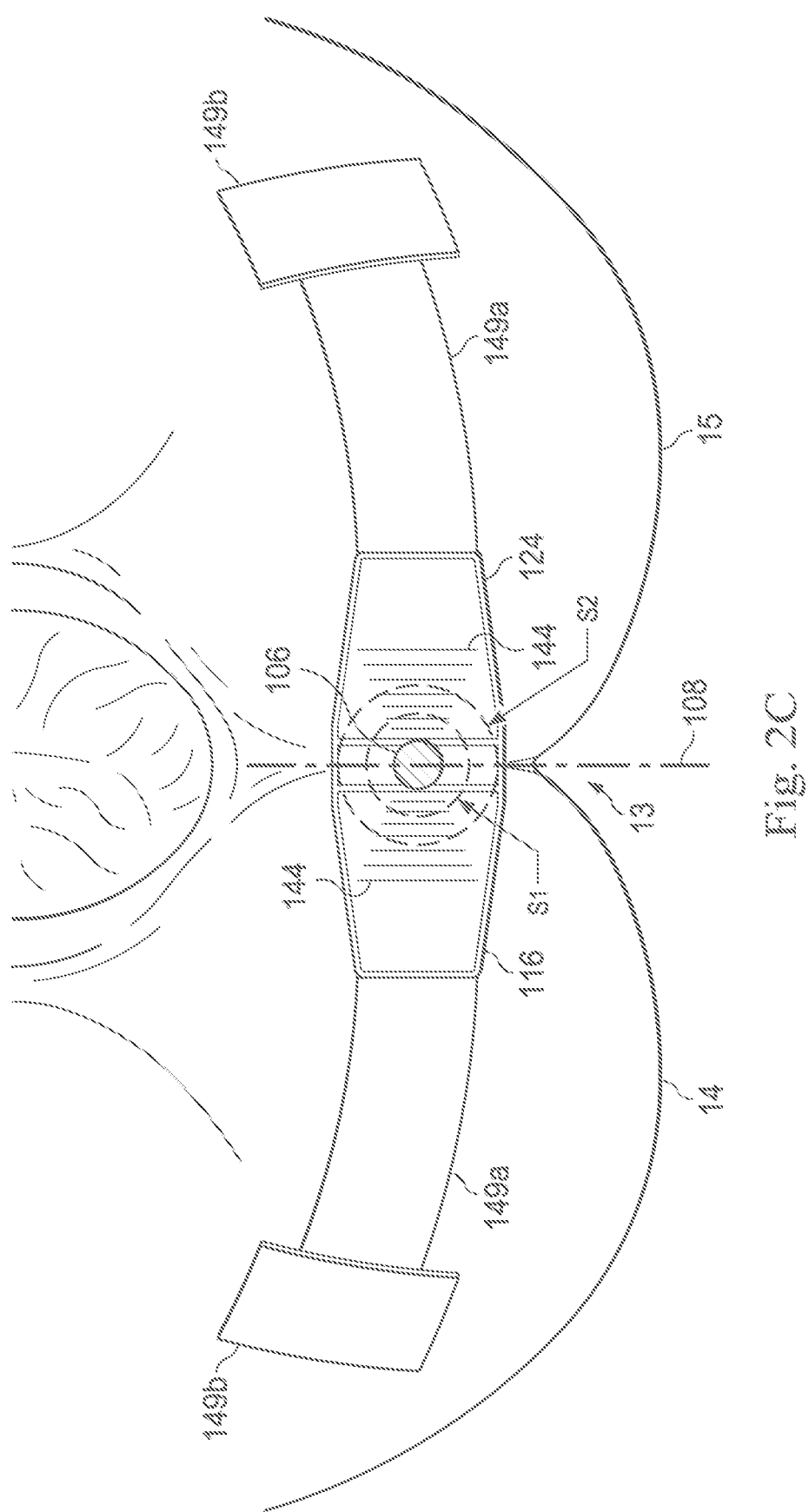
Figure 3:
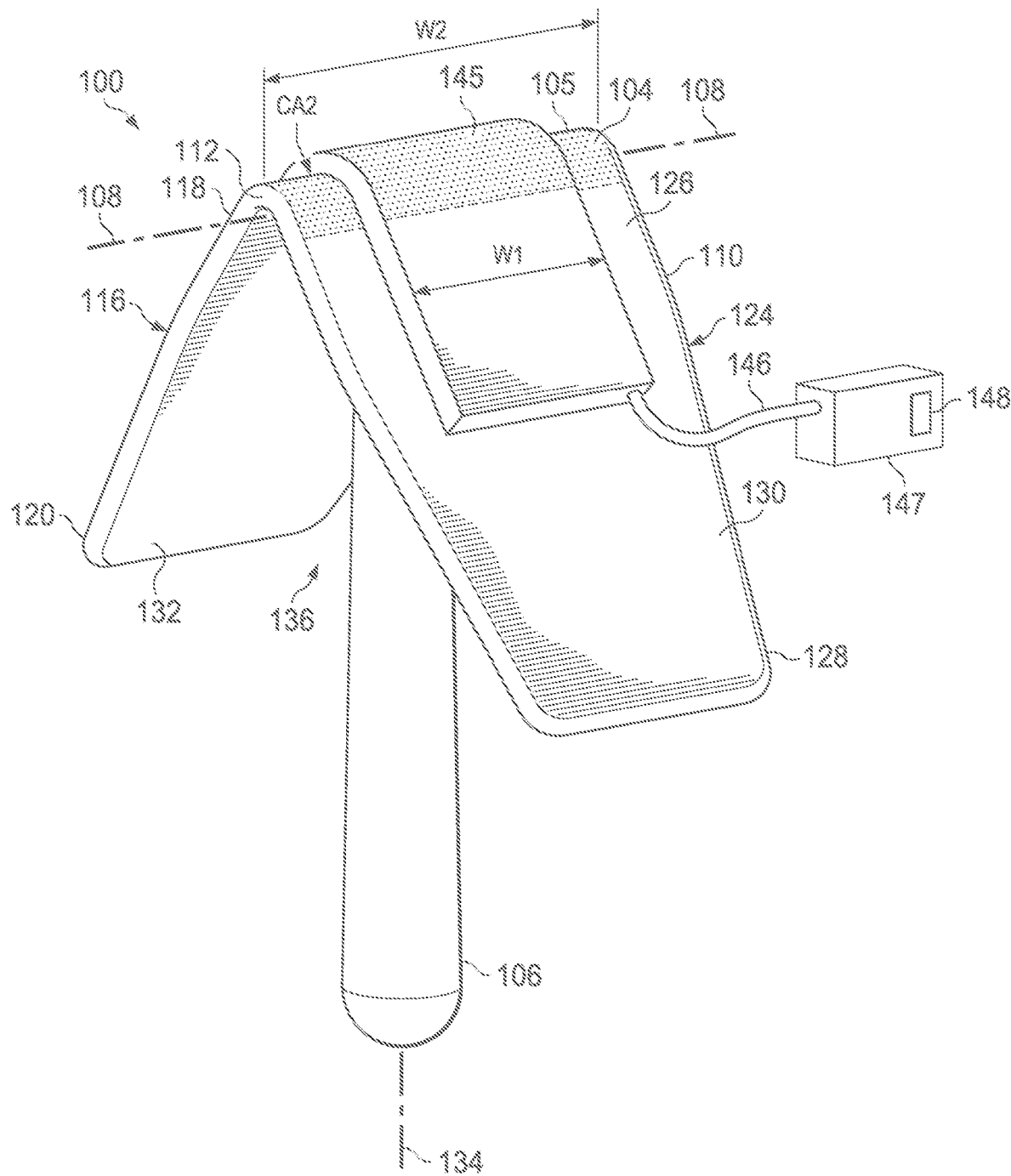
FIG. 3 illustrates a perspective view of the labor assistance system shown in FIG. 1 according to one embodiment of the present disclosure.
Figure 4:
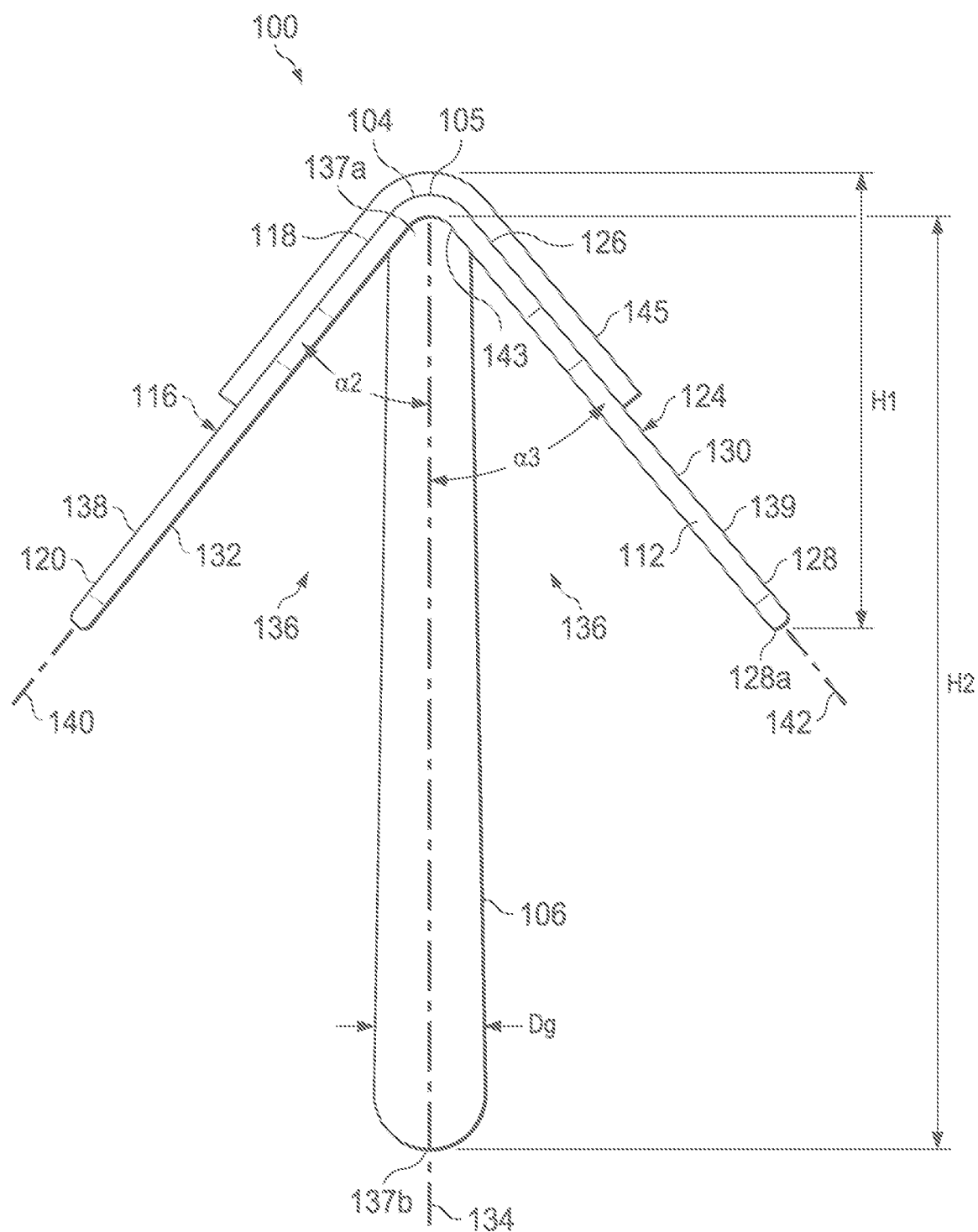
FIG. 4 illustrates a side view of the labor assistance system shown in FIG. 1 according to one embodiment of the present disclosure.

Turning now to FIG. 1-4, a labor assistance system 100 according to one exemplary embodiment disclosed herein is illustrated. FIGS. 1 and 2 show the labor assistance system 100 in association with the perianal tissue of a patient 10, and FIGS. 3 and 4 show the labor assistance system 100 independent of the patient 10.

In FIG. 1, the patient 10 is shown in partial cross section to illustrate a portion of the rectum 54, anal canal 36, anal orifice 26, internal venous plexus 29, pectinate line 37 (also known as the dentate line), and external venous plexus 28. The patient's buttocks 14 and 15 are shown with the crowns of the buttocks 16 and 17, respectively, laterally adjacent the perianal region 38. The gluteal cleft 13 (FIG. 2) is between the buttocks 14 and 15. The buttocks 14 and 15 extend laterally beyond crowns 16 and 17 toward lateral flanks 18 and 19, respectively. The crowns 16 and 17 of each buttocks 14 and 15 in essence define the midline of each leg and the lateral flanks 18 and 19 are the area lateral of the leg/buttocks midline. The lateral flanks 18 and 19 may include, for example but without limitation, all or a portion of the lateral buttocks, hips, or upper thigh of the patient.

FIG. 2 illustrates the patient 10 during a child birthing process. Contractions during labor move a child 12 into the birth canal and ultimately, for a vaginal delivery, through the vaginal opening 11, as shown in FIG. 2. In an alternative birthing process, labor is commenced to move the child 12, but for a variety of reasons, the delivery does not occur vaginally but instead caesarian delivery is performed through a surgical opening in the mother's abdomen. During the birthing process, tremendous pressure is exerted (e.g., generated by voluntary and involuntary muscle contractions) in an effort to move the child 12 toward delivery through the vaginal opening 11. By applying counter pressure with the labor assistance system 100 in the opposite direction to the perianal region 38 and the anal orifice 26 (FIG. 1), a user (e.g., a healthcare practitioner or the patient 10) can provide the patient 10 with a tactile, discrete source of resistance against which to push and support pelvic floor tissues to direct forces applied to the baby toward the vaginal opening.

In some embodiments, as described further below in relation to FIG. 15, the labor assistance systems disclosed herein can provide indicators that detect changes in intra-uterine pressure or pelvic tissue distension (e.g., by way of non-limiting example, anal distension, pelvic floor distension, perineal distension), and/or indicate when desired application pressures are achieved. Some exemplary embodiments provide feedback to users regarding changes in relevant pressure levels due to device application or physiological transformations, such as those that occur during muscle contractions during child delivery. The embodiments disclosed herein allow for real-time user adjustment systems and techniques, allowing a patient as well as a doctor to adjust the device for maximum comfort and effectiveness.

At least some of the pressure generated during labor is exerted against the tissues of the pelvic floor adjacent the anal orifice 26 in the perianal region 38 (FIG. 1). The result of these forces is that blood vessels near the anus, such as those in the external venous plexus 28, may bulge or rupture causing hemorrhoids or increasing their severity. Still further, other tissues in the perianal region 38 adjacent the anus may distend outwardly opposite arrow A4 in FIG. 1 causing lacerations such as tearing around the vaginal opening 11 or fissures from the anus. In addition to the blood loss, pain, and discomfort, these lacerations can be a location for infections in the mother. The systems, devices, and methods disclosed herein, including the exemplary labor assistance system 100, are shaped and structured to not only increase the strength and/or number of contractions by providing a tactile and/or visual guide to the mother during the birthing process, but also include features, elements, or structure that support the perianal tissues (tissue forming or supporting the perianal region 38) without interfering with the birthing canal or vaginal opening 11. For example, the exemplary systems, devices, and methods disclosed herein may support the tissue of the pelvic floor to inhibit damage to the tissue near the anal orifice 26, both internally and externally, to inhibit, for example but without limitation, the formation or advancement of external hemorrhoids, and/or to inhibit the formation or advancement of lacerations of the perianal tissues.

As shown in FIGS. 1 and 2, the labor assistance system 100 includes a perianal support member 102 having an external pressure surface or contact surface 104 and a grip 106. The contact surface 104 includes a continuous compression surface apex 105 dimensioned to span across an anal orifice for engagement with at least a portion of the external perianal tissue on opposing sides of the anal orifice of the patient. The contact surface 104 is anatomically configured to not enter the anal canal. For example, the contact surface 104 in the pictured embodiment comprises a convex, curved surface having a radius of curvature sized to substantially prevent the apex from entering the anal canal of the patient. The contact surface, and in particular the compression surface apex 105, is oriented to extend along a first direction in a sagittal plane of the patient when the system 100 is positioned within the gluteal cleft 13. As shown in FIG. 2, the contact surface 104 extends along a midline axis 108 extending longitudinally between a posterior edge 110 and an anterior edge 112 of the perianal support member. The grip 106 is configured to assist a user in holding the perianal support member 102 in pressurized engagement with the perianal tissue in the perianal region 38. In the pictured embodiment, the grip 106 is configured as a handle.

FIG. 3 shows a perspective view of the labor assistance system 100 independent of the patient 10, and FIG. 4 shows a side view of the labor assistance system 100 independent of the patient 10. The perianal support member 102 includes a pair of compression elements 116, 124 extending laterally from the contact surface 104. In the pictured embodiment, the compression elements 116, 124 are formed as flanges extending laterally from the contact surface 104. The first compression element 116 has a distal end portion 118 adjacent the contact surface 104 and an opposing proximal end portion 120. The opposing second compression element 124 has a distal end portion 126 adjacent the contact surface 104 and an opposing proximal end portion 128. The perianal support member 102 includes an outer surface 130 and an opposing inner surface 132 defining an access cavity 136.

Figure 5A:
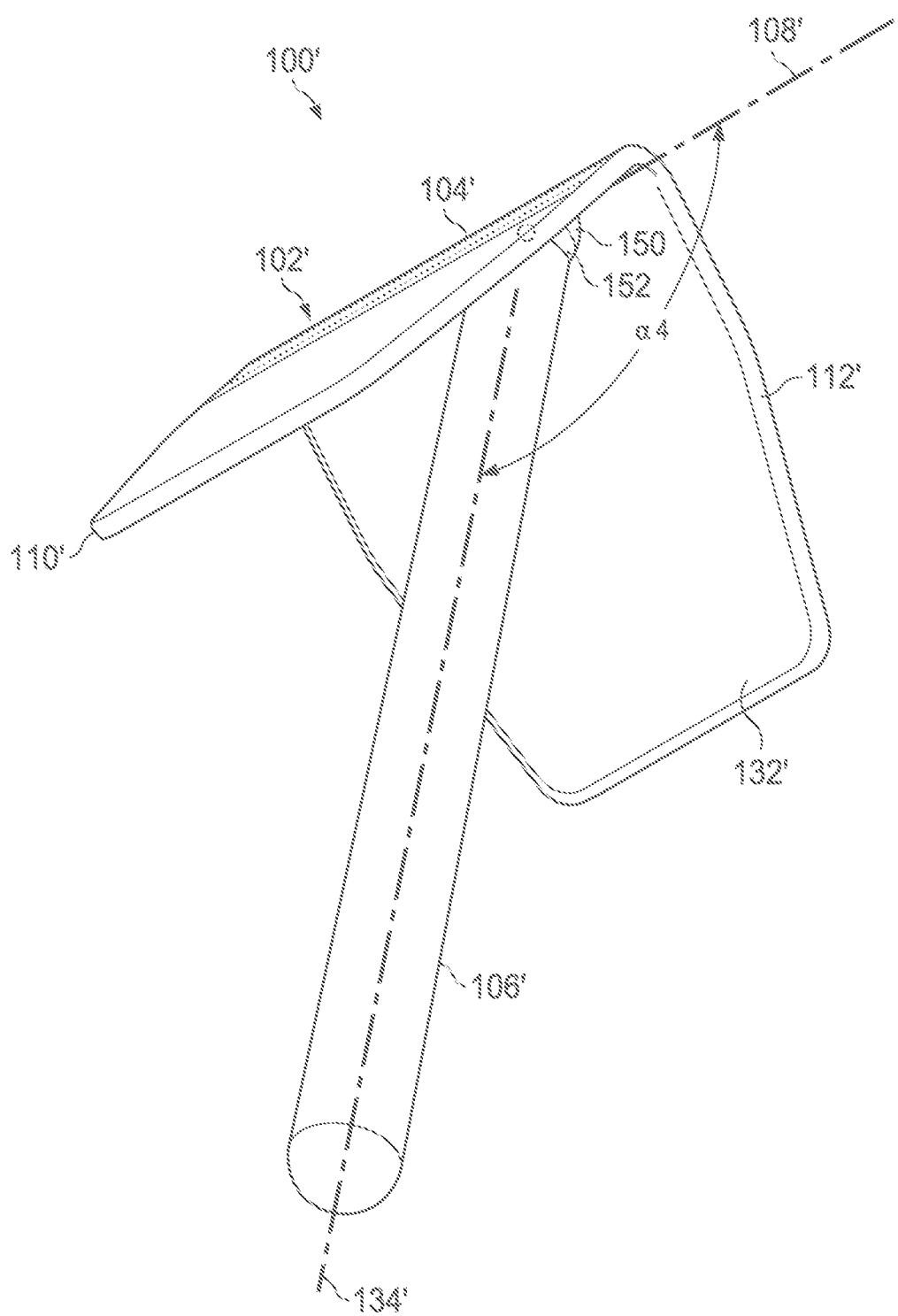
FIG. 5A illustrates a perspective side view of an exemplary labor assistance system according to one embodiment of the present disclosure.

In the pictured embodiment, the grip 106 extends from an area of the inner surface 132 located opposite the contact surface 104 (e.g., an internal contact surface 143). The grip 106 extends from the internal contact surface 143 in a direction away from the contact surface 104. In the pictured embodiment, the grip is spaced substantially equidistant from the anterior edge 112 and the posterior edge 110. In other embodiments, the grip 106 may be spaced closer to the anterior edge 112 or the posterior edge 110. In other embodiments, as described below with reference to FIGS. 10-14, the grip 106 may be formed in a variety of other shapes and coupled to the inner surface 132 in a variety of different ways. In the pictured embodiment, the grip 106 extends from the inner surface 132 at a constant angle relative to the midline axis 108 along an axis 134, which lies substantially perpendicular to the midline axis 108. It can be understood that the contact surface 104 is configured to be positioned at the gluteal cleft of the patient 10 with the midline axis 108 lying along the sagittal plane. In other embodiments, as shown in FIG. 5A, the grip 106 may be coupled to the inner surface 132 at a dynamic angle. In other embodiments, the coupling angle may be a non-perpendicular angle with respect to the midline axis 108.

Figure 13:
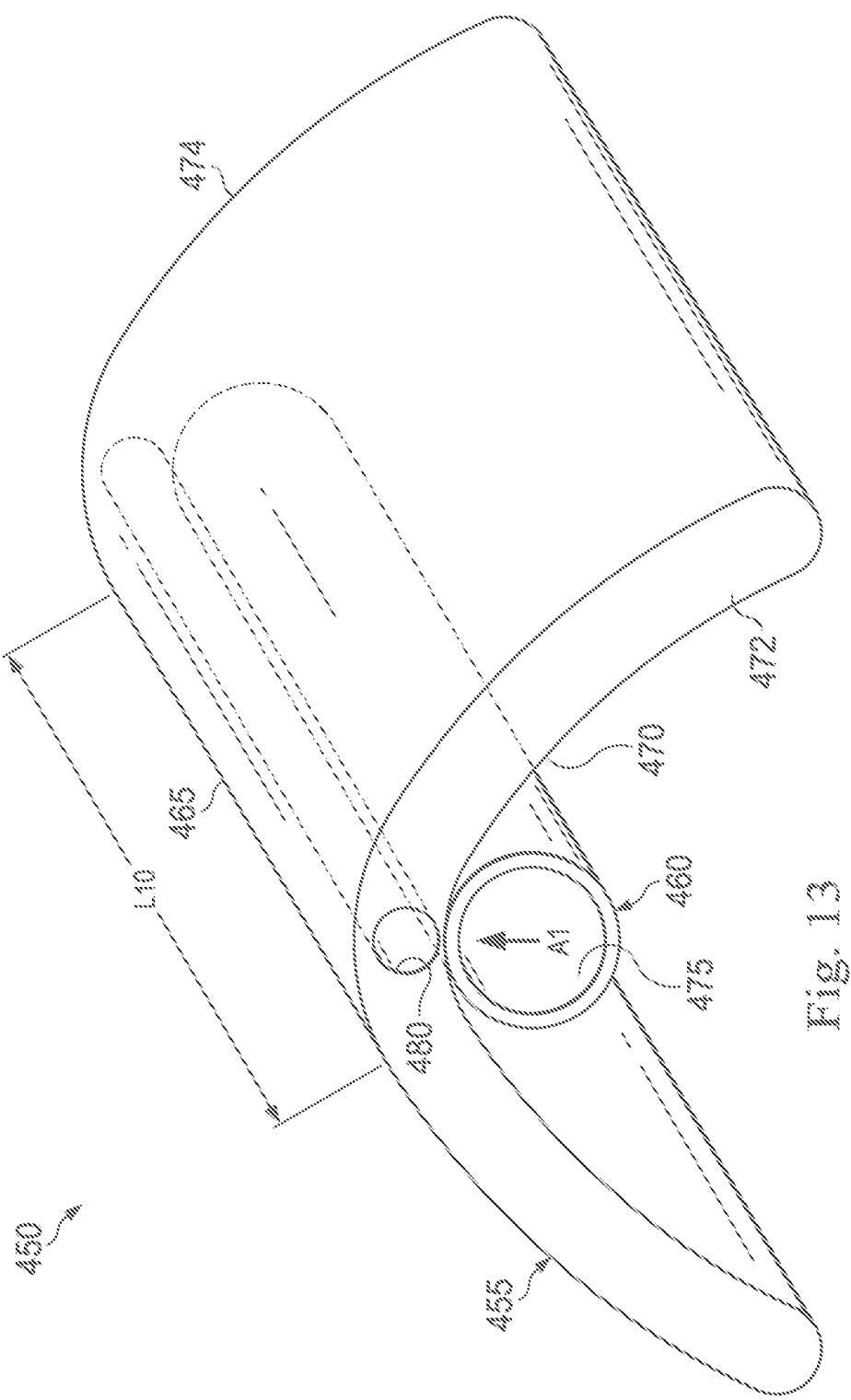
FIG. 13 illustrates an exemplary labor assistance system including the perianal support member shown in FIG. 1 coupled to an exemplary grip according to one embodiment of the present disclosure.
Figure 14:
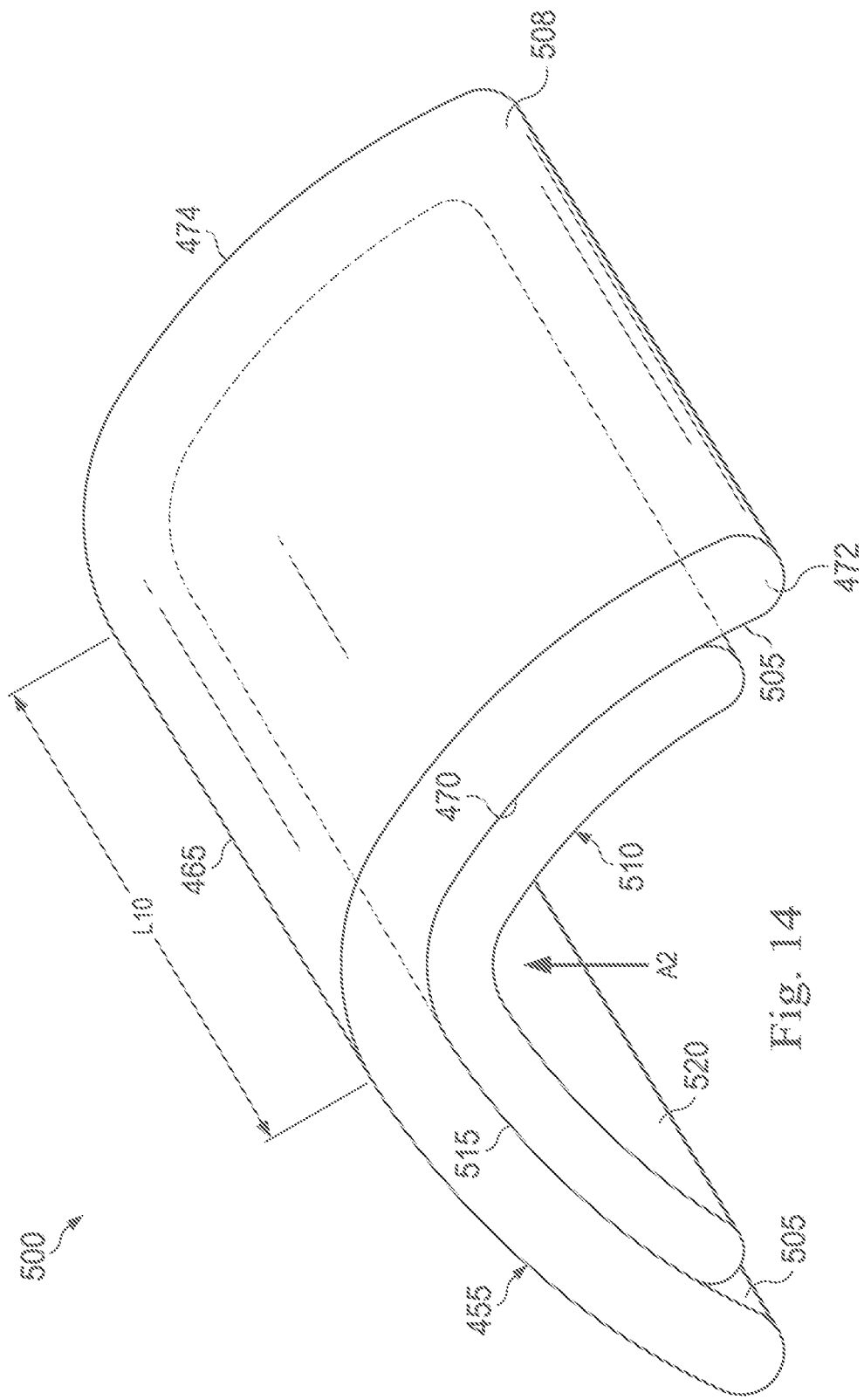
FIG. 14 illustrates an exemplary labor assistance system including the perianal support member shown in FIG. 1 coupled to an exemplary grip according to one embodiment of the present disclosure.

As shown in FIG. 4, the perianal support member 102 includes a height H1 extending from an apex of the contact surface 104 to the distal tip of the compression members (e.g., a distal tip 128a of the compression member 124). The height H1 may range from 1 cm to 10 cm. The grip 106 includes a height H2 extending from a distal end 137a (at the inner surface 132) to a proximal end 137b. The height H2 may range from 3 cm to 30 cm. Although the height H2 of the grip 106 is greater than the height H1 of the perianal support member 102, in other embodiments, the height H2 may be less than the height H1 (e.g., as shown in FIGS. 13 and 14). Although not limited to specific dimensions, the grip 106 includes a diameter Dg that may range from approximately 1 cm to 8 cm. As shown in FIG. 2, the grip 106 includes a cross-sectional area CA1 that may range from approximately 3 cm$^2$ to 25 cm$^2$. As shown in FIG. 3, the contact surface 104 includes a cross-sectional area CA2. In the pictured embodiment, the cross-sectional area CA1 of the grip 106 is substantially smaller than the cross-sectional area CA2 of the contact surface 104 (indicated in part by the dotted area shown in FIG. 3). In the illustrated embodiment of FIGS. 2 and 3, the ratio of CA2:CA1 is greater than 5:1. In other embodiments, the ratio of the cross-sectional areas CA2:CA1 may be larger (e.g., the ratio CA2:CA1 may be 1 or greater than 1). For example, in the embodiment described below with respect to FIG. 13, the cross-sectional area CA2 of the grip (e.g., the grip 460) may be substantially similar to the surface area CA1 of the contact surface 465. Other dimensions are contemplated, and the above dimensions are supplied for exemplary purposes only.

The first compression element 116 and the second compression element 124 meet at a first angle α1 to form the access cavity 136. In one embodiment angle α1, is between 140 degrees and 30 degrees. In the illustrated embodiment, angle α1 is approximately 80 degrees. In the example shown the first and second compression elements 116, 124 are integral with and define a portion of the perianal support member 102. The distal end portion 118 of the compression element 116 transitions into the contact surface 104. In a similar manner, the distal end 126 of the compression element 124 transitions into the contact surface 104. The compression element 116 comprises an elongated, planar exterior side wall 138 extending from the distal end 118 to the proximal end 120. The compression element 118 comprises an elongated, planar exterior side wall 139 extending from the distal end 126 to the proximal end 128. The compression member 116 extends generally along an axis 140, which is substantially transverse to the midline axis 108. The compression element 124 extends generally along an axis 142, which is substantially transverse to the midline axis 108. As shown in FIG. 4, the compression element 116 extends at an oblique angle α2 with respect to the axis 134 (e.g., the sagittal plane extending through the midline axis 108), and the compression element 118 extends at an oblique angle α3 with respect to the axis 134. It will be appreciated that in the illustrated embodiment, compression element 124 extends at an oblique angle α3 substantially equal to the oblique angle α2 at which compression element 116 extends with respect to axis 134. In some embodiments, the oblique angles α2 and α3 are each within the range of about 5 to 25 degrees. In other embodiments, the oblique angles α2 and α3 are each within the range of about 10 to 20 degrees, and in yet other embodiments, are with a range of about 15 to 20 degrees.

Referring back to FIG. 1, each compression element 116, 124 has a length L, and the maximum lateral distance of the access cavity 136 is defined by the distance D1 extending between the distal end portions 120, 128. In one embodiment, L is greater than 4 cm in length. In a preferred aspect, L is approximately 8 cm. In one embodiment, the maximum lateral distance D1 of the access cavity 136 is greater than 4 cm. In the illustrated embodiment of FIG. 1, the maximum lateral distance is approximately 10 cm.

The perianal support member 102 of the labor assistance system 100 has the internal contact surface 143 defined along the midline 108 opposing the contact surface 104. It will be understood that a health care provider may apply pressure to the contact surface 143 to move the perianal support member 102 into the operative position shown in FIGS. 1 and 2 and/or apply additional pressure to apply pressure to (and, in some instances, compress) at least some perianal and/or perineal tissue. The first compression element 116 includes an interior wall 144a while the second compression element 124 has an opposing interior wall 144b generally facing the interior wall 144a. The interior walls 144a, 144b, along with the internal contact surface 143 define the access cavity 136 within the labor assistance system 100. As shown in FIGS. 3 and 4, the configuration of the perianal support member 102 as described above results in a generally wedge shaped device. Still further, with the inclusion of the access cavity 136, the perianal support member 102 has a substantially V-shaped configuration with the contact surface 104 defined at the apex of the V and the compression elements 116, 124 forming the legs of the V. In other embodiments, as described below with reference to FIG. 8, the perianal support member may lack an access cavity altogether.

FIGS. 2B and 2C illustrate partial perspective bottom views of the labor assistance system 100 positioned against a patient during two different pressure situations during child delivery. In some embodiments, the perianal support member 102 is formed of an opaque material. In other embodiments, the perianal support member 102 is formed of an optically clear material that enables the user to see through the compression elements 116, 124 and/or the contact surface 104. For example, in the pictured embodiment, the perianal support member 102 is formed of a clear, transparent, translucent, or semi-translucent material. The material composition of the perianal support member 102 allows the user to visually observe and/or measure the changes in tissue distension (e.g., secondary to pressure changes against the perianal support member 102) occurring on the contact surface 104 and the exterior side walls 138, 139 of the compression elements 116, 124, respectively, shown in FIG. 4. The clear, transparent, translucent, or semi-translucent material of the perianal support member 102 allows the user to view the changes in tissue distension through the perianal support member 102 without removing the perianal support member 102 from the patient 10.

In the pictured example, FIG. 2B illustrates an area S1 that represents the initial tissue spread against the perianal support member 102 upon an initial placement of the labor assistance system 100 on the patient 10. FIG. 2C illustrates an area S2 that represents the subsequent tissue spread against the perianal support member 102 during different pressure conditions (e.g., as might occur during voluntary or involuntary contractions, while the patient 10 pushes, and/or while the user applies more pressure to the perianal support member 102 through the grip 106). The user may observe the changes in tissue spread or tissue distension to evaluate the changes in pressure associated with the progress of labor. If the tissue spread is not adequate or is excessive, this may indicate that the mother's labor or labor efforts (e.g., voluntary contractions) are not progressing appropriately.

In some embodiments, as shown in FIGS. 2B and 2C, the perianal support member 102 includes markings 144 designed to indicate measurements, a ruler, or a scale that assist the user in making precise measurements and comparisons of tissue distention through different pressure conditions throughout the labor process. The markings 144 may comprise any variety of indicators (e.g., shapes, lines, colors) designed to convey measurement data. The markings 144 may extend across the perianal support member from one compression element to the other, as shown, or may extend along the contact surface along the midline axis 108 (e.g., as shown in FIG. 22A). The markings 144 may be positioned across only a portion of the perianal support member 102, or may be positioned across the entirety of the perianal support member 102. In some embodiments, the markings 144 may be on the contact surface 104 and the exterior side walls 138, 139 of the compression elements 116, 124, respectively, and in other embodiments, the markings 144 may be on the inner surface 132.

In some embodiments, the perianal support member 102 may lack predefined markings for measurements, such as the markings 144 in FIGS. 2B and 2C. In such embodiments, the user may manually mark the perianal support member 102 (e.g., on the inner surface 132) to mark the relevant or desired margins of the area S1 and the area S2, and then quantitatively (by measuring the difference in areas as indicated by the hashed area in FIG. 2C) or qualitatively (by visually observing the marked areas) compare the different degrees of tissue distension to evaluate the progress of labor and/or the effectiveness of the pushing effort of the patient 10. The user may use a marker or a grease pencil, by way of non-limiting example, to permanently or temporarily mark the perianal support member 102.

In the embodiment shown in FIGS. 3 and 4, the labor assistance system includes a pad 145 positioned on the contact surface 104. In some embodiments, the pad 145 has a width W1 that is substantially equivalent to a width W2 of the contact surface 104, and in other embodiments, as shown in FIG. 3, the pad 145 has a width W1 less than the width W2 of the contact surface 104. The anterior to posterior width W2 of the contact surface 104 between the anterior edge 112 and the posterior edge 110 is approximately 5 cm in the illustrated embodiment. This midline width W2 can be adjusted in some embodiments depending on the amount and extent of perianal tissue that needs to be supported. In the embodiment shown the pad 145 extends along the contact surface 104 and extends at least partially along the outer surface 130 of the perianal support member 102, covering at least a portion of the first compression element 116 and the second compression element 124. The pad 145 may be disposed and arranged as an interfacing structure disposed between the contact surface 104 of the perianal support member 102 and the patient's perianal tissue 38 (shown in FIG. 1) when the labor assistance system 100 is positioned in contact with the patient 10.

In some embodiments, the pad 145 comprises an anatomically conformable structure. In some embodiments, the pad 145 comprises a compliant pad. In some instances, the pad 145 may be formed of a compliant material such as, by way of non-limiting example, polyurethane, silicon, rubber, foam, or cotton. Such materials may enable the pad 145 to conform to the patient's anatomy as the labor assistance system 100 is positioned in contact with the patient 10. In some embodiments, the pad 145 is formed of a material that retains its shape (e.g., a complementary shape to the patient's tissue surface) upon removal of the pad 145 from the patient's tissue. For example, in some embodiments, the pad is formed of a clay or clay-like polymer that has a high degree of conformability when pushed against the patient, but retained that "conformed" shape upon removal of the pad 145 from the patient. In some embodiments, the pad 145 is a sterile gauze pad. In other embodiments, the pad 145 includes an internal cushioning structure, such as polyurethane, silicon, rubber, foam, cotton, etc., with a non-abrasive skin contact surface.

In other instances, the pad 145 comprises a hollow, inflatable structure that may be selectively inflated with various amounts of fluids (e.g., by way of non-limiting example, air, liquid, gels). In some embodiments, the pad 145 may be adjusted by the user to exhibit different degrees of conformability. For example, in some embodiments, the pad 145 may be inflated through a tube 146 that may be attached to the pad 145 from a fluid source 147. In some embodiments, the tube 146 is a detachable tube that may be removed or disengaged from the pad 145 and/or the fluid source 147. In some embodiments, the fluid source 147 comprises a pump-like structure which may be electronically or manually operated to increase or decrease the amount of fluid within the pad 145. In some embodiments, the fluid source 147 includes a control feature 148 that allows the user to control the fluid ingress and/or egress from the pad 145. In some instances, increasing the amount of fluid within the pad 145 will increase the turgidity and lessen the degree of conformability of the pad 145. If the user fills the pad 145 with fluid, the pad 145 may hold its shape and stop conforming to the patient's tissue contours. If, however, the pad 145 is incompletely filled with fluid, the pad 145 may retain a high degree of conformability and assume a complementary shape to the contours of the patient's tissue as the labor assistance system 100 is positioned in contact with the patient 10.

In some instances, the pad 145 is opaque. In other instances, the pad 145 may be clear or translucent, thereby allowing the user to visually observe changes in tissue distension through the pad (i.e., by observing changes in the area of tissue contact against the pad 145 over time). The pad 145 may be adhered to the perianal support member 102 across the majority of the contact surface 104.

In one embodiment, the pad 145 is die cut from 1776 and 1772 stock materials from 3M. In another embodiment, pad 145 is an absorbent material adapted to absorb bodily fluids. It will be appreciated that the pad 145 may make placement and application of the labor assistance system 100 more comfortable for the patient. In addition, the surface of the pad 145 is configured to frictionally engage the patient's perianal tissue to inhibit movement between the labor assistance system 100, particularly the contact surface 104 and the patient.

In still a further aspect, the pad 145 includes a treating compound. The treating compound can be disposed within the pad 145, applied on the surface, or a combination of both. Treating compounds useful for combination with pad 145 include, but without limitation to other compounds, antibacterial compounds, antibiotic compounds, sclerants, antimicrobial compounds, anti-inflammatory compounds, anti-fungal agents, anti-itching agents, humicants, moisture absorbing agents, gas absorbing agents, buffering agents for pH control, drying agents and the like and coagulants.

In yet a further embodiment, the pad 145 is not fixed to the perianal support member 102 but is instead positioned on the patient in advance of positioning the perianal support member 102 or is loosely held to the perianal support member 102 as it is applied to the body. In this embodiment, the pressure applied via the grip 106 on the perianal support member 102 can maintain the position of the pad 145 relative to the patient's body and in particular the anal orifice 26 (shown in FIG. 1).

Returning to the embodiment shown in FIGS. 2B and 2C, the labor assistance system includes two securing members 149a that terminate in anchor pads 149b. The anchor pads 640 are shaped and configured to be removably attached to the buttocks 14, 15 (e.g., within the gluteal cleft 13) of the patient 10. The securing system is substantially the same as described in U.S. Pat. No. 7,673,633, entitled "Apparatus and Method of Inhibiting Perianal Tissue Damage," which is hereby incorporated by reference in its entirety. In some embodiments, the anchor pads 149b may be adhesively attached to the patient 10. In the pictured example, each securing member 149a is fixedly coupled to one of the compression elements 116, 124 and one of the anchor pads 149b. In some examples, the securing members 149a include a first half of a releasable fastening system coupled to the compression elements, such as a hook and loop system or a releasable adhesive system. In the illustrated embodiment, the anchor pads 149b have a generally rectangular shape that is shorter in length and wider than elongated securing members 149a. The shape of the anchor pad is shown for illustration purposes and may take any form that is suitable for fixing to a patient or inanimate object, as well as joining to the elongated fixation member. Each anchor pad 149b includes a first surface having an adhesive surface (substantially similar to the adhesive surface 642 described in more detail with relation to FIG. 15) adapted for joining to the patient's skin or some inanimate object. The opposing surface (substantially similar to the adhesive surface 644 described in more detail with relation to FIG. 15) includes the second half of the fastening system, which couples to the securing member 149a. In some embodiments, at least a portion of a surface of the first surface includes an adhesive coating that can fix the securing member to another object. In one embodiment, the adhesive coating is adapted for releasably adhering to a patient's skin.

Figure 5B:
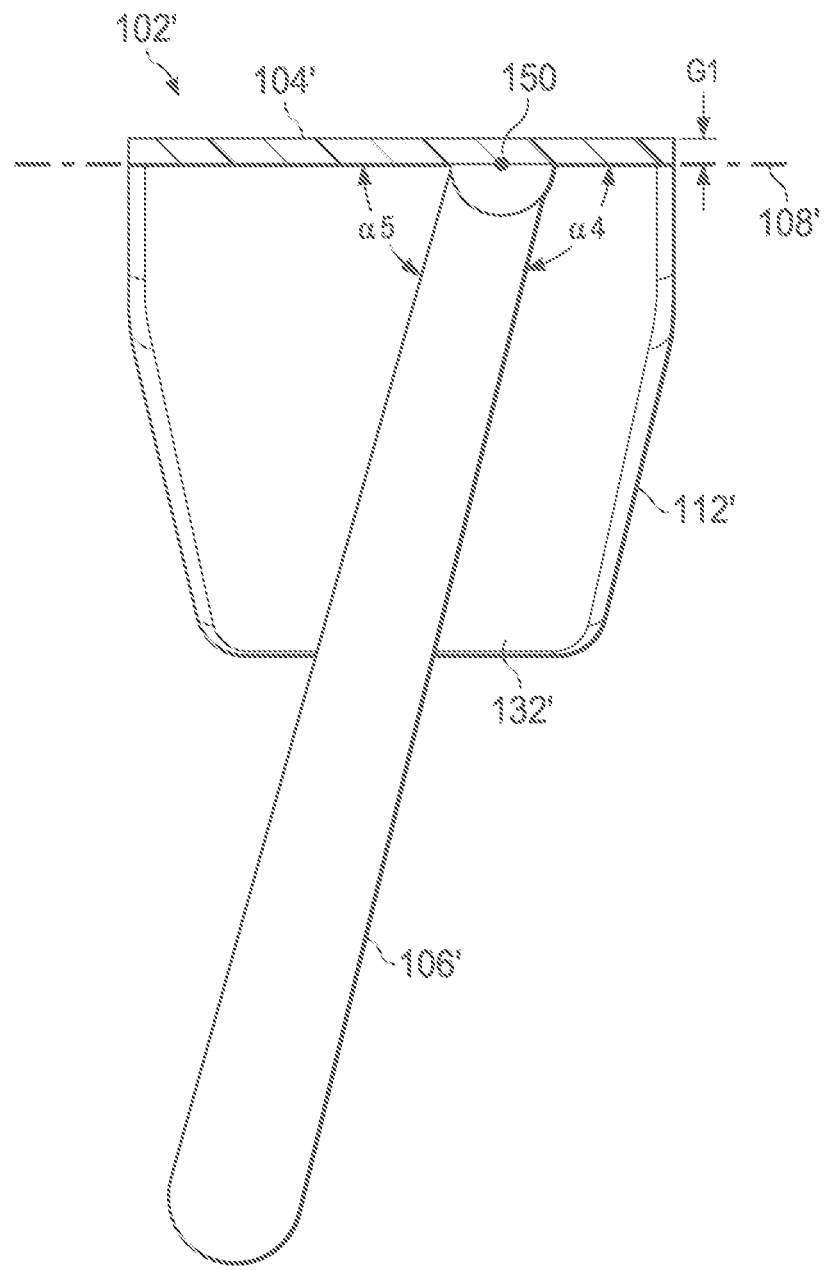
FIG. 5B illustrates a cutaway side view of the exemplary labor assistance system shown in FIG. 5A according to one embodiment of the present disclosure.

FIG. 5A shows a side view of an exemplary labor assistance system 100' according to one embodiment of the present disclosure, and FIG. 5B shows cutaway side view of the labor assistance system 100'. The labor assistance system 100' is substantially similar to the labor assistance system 100 except for the differences described herein. For example, the labor assistance system 100' includes a grip 106' movably coupled to an inner surface 132' of a perianal support member 102' at a pivot element 150. The pivot element 150 may comprise any of a variety of coupling elements configured to permit the grip 106' to move with respect to a midline axis 108' of a contact surface 104' of the perianal support member 102'. For example, the pivot element 150 may comprise, without limitation, a hinge, a rotatable ball-and-socket joint, a knuckle joint, a pin joint, and a screw joint. As shown in FIG. 5B, the pivot element 150 may be spaced by a distance or gap G1 from the contact surface 104' of the perianal support member 102'. In the pictured embodiment, the grip 106' is shown positioned at a non-perpendicular angle with respect to the midline axis 108'. A longitudinal axis 134' of the grip 106' intersects the midline axis 108' to form an acute angle α4 and, as shown in FIG. 5B, an obtuse angle α5. In some embodiments, the pivot element 150 couples the grip 106' to the perianal support member 102' at the dynamic angle α4 which changes in response to the actions of the user holding the grip 106' and/or the movements of the patient 10. As shown in FIG. 5B, in some embodiments, the pivot element 150 couples the grip 106' the perianal support member 102' in a manner that allows the grip 106' to be repositioned anywhere within the 180° degree arc indicated by angles α4 and α5. In other embodiments, the pivot element 150 includes a locking feature 152 that enables the user to temporarily and reversibly lock or fix the angle α4. The locking feature 152 may be positioned on the grip 106' and/or the perianal support member 102'. The locking feature 152 may include any variety of locking means shaped and configured to temporarily lock the grip 106' in at a fixed angle α4 relative to the midline axis 108'. For example, by way of non-limiting example, the locking feature 152 may comprise a protrusion on the grip 106' configured to mate with a depression on the inner surface 132'. In the pictured embodiment, the grip 106' is coupled to the inner surface 132' at a position closer to an anterior edge 112' than a posterior edge 110' of the perianal support member 102'. In other embodiments, the pivot element 150 (and the grip 106') may be spaced closer to the posterior edge 110'.

FIGS. 6 - 9 illustrate different embodiments of a perianal support member according to various embodiments of the present disclosure. The perianal support members described herein may be combined or coupled with any of the grips described in this disclosure to form various labor assistance systems. For purposes of illustration, the grip 106 is shown in dotted lines coupled to the exemplary perianal support members shown in FIGS. 6-9. The grips may be coupled to the exemplary perianal support members via a pivot element (e.g., the pivot element 150 described above). In other embodiments, the grips may be attached to the exemplary perianal support members in a fixed relationship.

The grips extend from the perianal support member and are configured and arranged to permit the patient to adjust the relative position and orientation of the labor assistance system. The adjustment may include modifying the pressure applied by the perianal support member on the perianal tissue or may include adjusting the physical location of the perianal support member on the patient. Accordingly, during contractions or during pushing, the user can apply additional pressure on the perianal and/or perineal tissue if desired. Therefore, the user has some level of control of the pressure on the perianal and/or perineal tissue.

When additional pressure loading is desired, the user may press on the grip in the general direction of the patient's head so that the perianal support member applies additional loading onto the perianal tissue. In some embodiments, the user may monitor the push strength of the patient, the force, duration, and strength of intrauterine contractions, and/or other markers of the progression of labor described herein, and may adjust the labor assistance system using the grip to maintain the applied pressure against the patient in a desired pressure range. The grip allows a user to quickly and easily adjust the relative position and orientation of the perianal support member on the perianal tissue and to increase or decrease the pressure on the perianal tissue. In particular, the user may adjust the position or the pressure applied by the perianal support member by manipulating the grip relative to patient.

Figure 6:
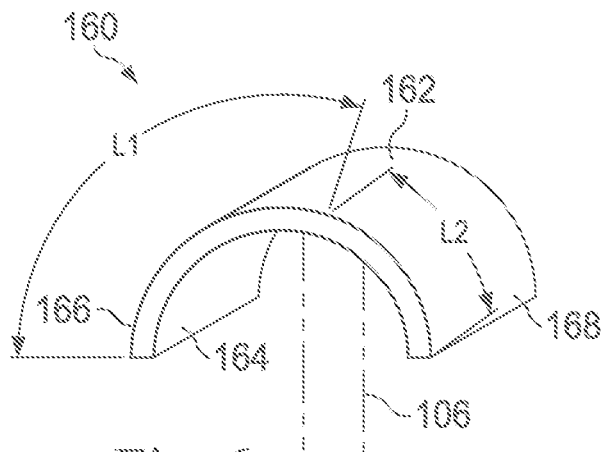
FIG. 6 illustrates a perspective view of an exemplary perianal support member according to one embodiment of the present disclosure.

FIG. 6 illustrates a perspective view of an exemplary perianal support member 160 according to one embodiment of the present disclosure. The perianal support member 160 is substantially similar to the perianal support member 102 except for the differences described herein. Unlike the perianal support member 102, which has a V-shaped side profile, the perianal support member 160 has a generally U-shaped side profile. The perianal support member 160 includes a curved or rounded contact surface 162 and an opposing inner surface 164. A grip (e.g., the grip 106 discussed above) may be coupled to and extend from the inner surface 164. The perianal support member 160 includes compression elements 166 and 168 that flank the contact surface 162 and have substantially the same radius of curvature as the contact surface 162. In some embodiments, the compression elements 166, 168 are integral extensions of the contact surface 162. In other embodiments, the compression elements 166, 168 are coupled to the contact surface 162. The compression elements 166, 168 may extend equal distances from the contact surface 162, as shown in FIG. 6, or they may extend unequal or different distances from the contact surface 162. For example, in some embodiments, the compression element 166 may include a length L1 that is less than or greater than a length L2 of the compression element 168.

Figure 7:
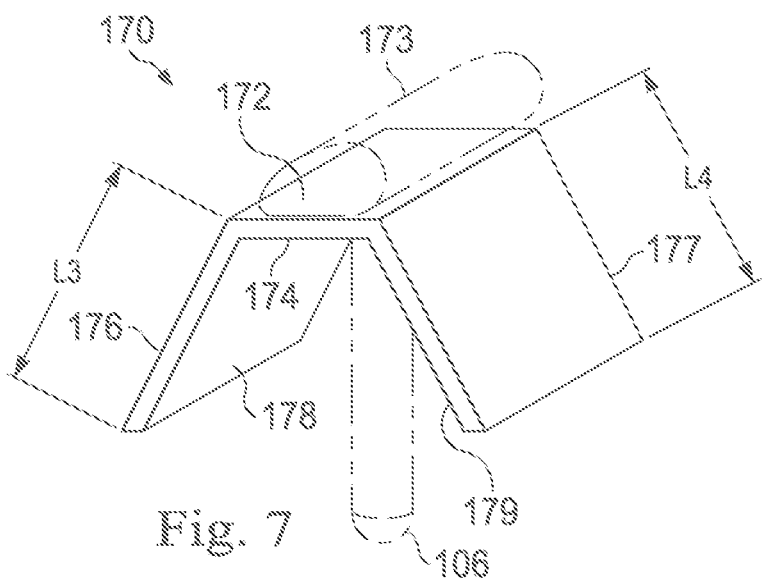
FIG. 7 illustrates a perspective view of an exemplary perianal support member according to one embodiment of the present disclosure.

FIG. 7 illustrates a perspective view of an exemplary perianal support member 170 according to one embodiment of the present disclosure. The perianal support member 170 is substantially similar to the perianal support member 102 except for the differences described herein. Unlike the perianal support member 102, which has a V-shaped side profile, the perianal support member 170 has a trapezoidal side profile. The perianal support member 170 includes a flat contact surface 172 and an opposing inner surface 174. A grip (e.g., the grip 106 discussed above) may be coupled to and extend from the inner surface 174. The perianal support member 170 includes compression elements 176 and 177 that flank the contact surface 172. The compression elements 176, 177 include inner surfaces 178, 179, respectively. In some embodiments, the compression elements 176, 177 are integral extensions of the contact surface 172. In other embodiments, the compression elements 176, 177 are coupled to the contact surface 172. The compression elements 176, 177 may extend equal distances from the contact surface 172, as shown in FIG. 7, or they may extend unequal or different distances from the contact surface 172. For example, in some embodiments, the compression element 176 may include a length L3 that is less than or greater than the length L4 of the compression element 177.

In an alternative form, a compliant pad 173 (shown in dash) is added to the contact surface 172. It is joined to the surface 172 by adhesive or any suitable joining technique. In one method, the pad 173 may be a separate component that is positioned on the patient before the support member 170 is positioned in a supporting fashion on the patient. In some embodiments, the pad 173 comprises an anatomically conformable structure. In some embodiments, the pad 173 comprises a compliant pad. In some instances, the pad 173 may be formed of a compliant material such as, by way of non-limiting example, polyurethane, silicon, rubber, foam, or cotton. Such materials may enable the pad 173 to conform to the patient's anatomy as the labor assistance system 170 is positioned in contact with the patient 10. In some embodiments, the pad 173 is formed of a material that retains its shape (e.g., a complementary shape to the patient's tissue surface) upon removal of the pad 173 from the patient's tissue. For example, in some embodiments, the pad is formed of a clay or clay-like polymer that has a high degree of conformability when pushed against the patient, but retained that "conformed" shape upon removal of the pad 173 from the patient. In some embodiments, the pad 173 is a sterile gauze pad. In other embodiments, the pad 173 includes an internal cushioning structure, such as polyurethane, silicon, rubber, foam, cotton, etc., with a non-abrasive skin contact surface.

In other instances, the pad 173 comprises a hollow, inflatable structure that may be selectively inflated with various amounts of fluids (e.g., by way of non-limiting example, air, liquid, gels). In some embodiments, the pad 173 may be adjusted by the user to exhibit different degrees of conformability. For example, in some embodiments as described above with respect to FIG. 3, the pad 173 may be inflated through a tube that may be attached to the pad 173 from a fluid source. In some instances, increasing the amount of fluid within the pad 173 will increase the turgidity and lessen the degree of conformability of the pad 173. If the user fills the pad 173 with fluid, the pad 173 may hold its shape and stop conforming to the patient's tissue contours. If, however, the pad 173 is incompletely filled with fluid, the pad 173 may retain a high degree of conformability and assume a complementary shape to the contours of the patient's tissue as the labor assistance system 170 is positioned in contact with the patient.

Figure 8:
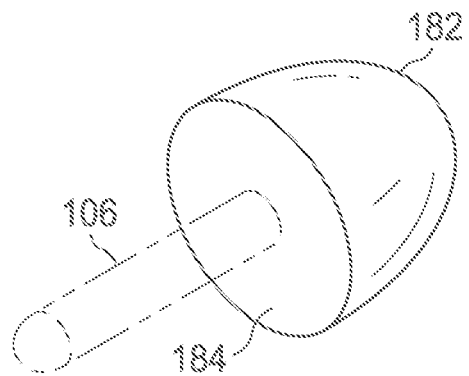
FIG. 8 illustrates a perspective view of an exemplary perianal support member according to one embodiment of the present disclosure

FIG. 8 illustrates a perspective view of an exemplary perianal support member 180 according to one embodiment of the present disclosure. The perianal support member 180 is substantially similar to the perianal support member 102 except for the differences described herein. Unlike the perianal support member 102, which has a V-shaped, concave side profile, the perianal support member 180 has a curved, dome-like, solid side profile. The perianal support member 180 is shaped and configured as a solid shape having an arcuate contact surface 182. The perianal support member 180 includes the curved or rounded contact surface 182 and an opposing inner surface 184. The inner surface 184 forms a substantially flat, planar surface. Thus, the perianal support member 180 lacks an access cavity (e.g., the access cavity 136 shown in FIG. 3). In other embodiments, the inner surface 184 may be slightly convex or slightly concave. A grip (e.g., the grip 106 discussed above) may be coupled to and extend from the inner surface 184.

The perianal support member 180 includes compression elements 186, 188 that form integral or continuous extensions of the contact surface 182.

Figure 9A:
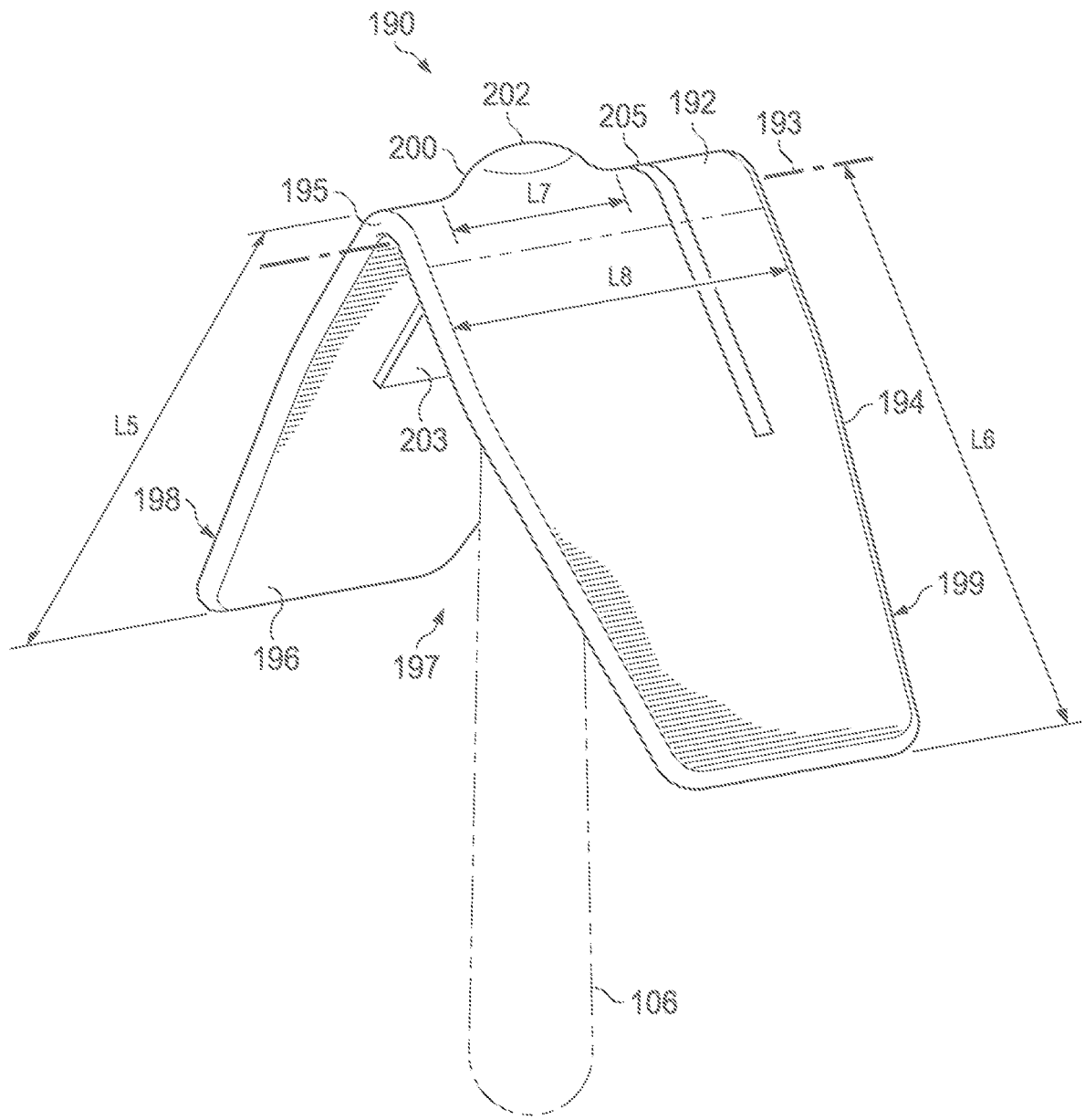
FIG. 9A illustrates a perspective view of an exemplary perianal support member according to one embodiment of the present disclosure.

FIG. 9A illustrates a perspective view of an exemplary perianal support member 190 according to one embodiment of the present disclosure. The perianal support member 190 is substantially similar to the perianal support member 102 except for the differences described herein. For example, the perianal support member 190 includes a contact surface 192 extending along a midline axis 193 from a posterior edge 194 to an anterior edge 195. An opposing inner surface 196 defines an access cavity 197. A grip (e.g., the grip 106 discussed above) may be coupled to and extend from the inner surface 196. The perianal support member 190 includes compression elements 198 and 199 that flank the contact surface 192. In some embodiments, the compression elements 198, 199 are integral extensions of the contact surface 192. In other embodiments, the compression elements 198, 199 are coupled to the contact surface 192. The compression elements 198, 199 may extend equal distances from the contact surface 192, as shown in FIG. 9A, or they may extend unequal or different distances from the contact surface 192. For example, in some embodiments, the compression element 198 may include a length L5 that is less than or greater than a length L6 of the compression element 199.

The perianal support member 190 includes a focusing pressure element or focal protrusion 200 disposed on the contact surface 192. In the pictured embodiment, the focusing pressure element 200 comprises a raised protrusion extending outwardly from the contact surface 192 away from the compression elements 198, 199 and having a curved shape. In other embodiments, the focusing pressure element 200 may comprise any structure shaped and configured to apply a focal area of increased pressure upon the perianal region 38 or perineal region of the patient 10 (shown in FIG. 1). For example, without limitation, the focusing pressure element 200 may comprise a textured area (e.g., having a different texture than the remainder of the contact surface 192), a protrusion having a polygonal shape, or a plurality of protrusions or ridges. In the pictured embodiment, the focusing pressure element 200 is spaced farther from the posterior edge 194 than the anterior edge 195. This configuration enables the user to position the perianal support member 190 against the patient 10 such that the focusing pressure element 200 abuts the perineal region between the anal orifice 26 and the vaginal opening 11 (shown in FIGS. 1 and 2) without obstructing the vaginal opening 11. In other embodiments, the focusing pressure element 200 may be spaced equidistant from the anterior edge 195 and the posterior edge 194, or may be positioned closer to the posterior edge 194 than the anterior edge 195. In the pictured embodiment, the focusing pressure element 200 includes a length L7 along the axis 193 that is less than a length L8 of the contact surface 192. In other embodiments, the length L7 of the focusing pressure element 200 may comprise any fraction of the length L8 of the contact surface 192. For example, the length L7 may comprise one-fourth, one-third, or one-half the length L8 of the contact surface.

In some embodiments, the perianal support member 190 may include a pressure sensor 202 on the contact surface 192. In the pictured embodiment, the pressure sensor 202 is positioned on the focusing pressure element 200. In other embodiments, the pressure sensor 202 may be found on another part of the contact surface 192. In some embodiments, the pressure sensor 202 may protrude outward from the contact surface 192 and may be configured to extend completely or partially into the patient's anal canal. In other embodiments, the pressure sensor 202 may be configured for external placement against the pelvic tissues (e.g., perianal tissue) of the patient 10. The pressure sensor 202 may be includes on any of the perianal support member embodiments described herein.

In some embodiments, the perianal support member 190 may include a haptic feedback generator 203, which may be positioned on the inner surface 196 as shown in the pictured embodiment or, on the contact surface 192, or on the grip 106. In some embodiments, the haptic feedback generator 203 may be positioned on the focusing pressure element 200. In other embodiments, the haptic feedback generator 203 may be found on another part of the contact surface 192. In some embodiments, the haptic feedback generator 203 may be configured to provide haptic feedback to the user and/or the patient 10 via any type of suitable tactile feedback (e.g., by way of non-limiting example, vibrations, forces, or motions) through the perianal support member 190 and/or the grip 106. In some embodiments, the haptic feedback generator 203 may be connected to the pressure sensor 202 (either wirelessly or through a wired connection) to provide varying degrees of haptic feedback depending upon the amount of pressure registered by the pressure sensor 202. For example, in one instance, the haptic feedback generator 203 may provide increasing (e.g., stronger or faster) vibrations through the perianal support member 190 when a pressure increase is sensed by the pressure sensor 202. The haptic feedback generator 203 may be included on any of the labor assistance system embodiments described herein.

In use, the user (e.g., the health care provider, the patient, or another) can position the perianal support member 190 against the patient's perianal region 38 or perineal region to apply increased pressure to the focal area in contact with the focusing pressure element 200. In some embodiments, this focused application of increased pressure (relative to the surrounding tissues) stimulates a nerve or bundle of nerves to enhance the pushing reflex in the patient 10 (e.g., similar to the Ferguson reflex). For example, a user may push the grip 106 at the appropriate angle to transfer sufficient pressure through the focusing pressure element 200 against a focal area of the perianal or perineal region of the patient 10 to stimulate the patient's urge to push the child out of the birth canal. In other instances, the focal application of pressure through the pressure element 200 against the perianal or perineal region of the patient 10 may assist in guiding the child's head and body along an optimal route through the vaginal canal.

FIG. 9A shows a visual indicator or marker 205 that can assist a user in properly positioning the perianal support member 190 on the patient 10. In this example, the marker 205 is an elongated shape formed on the contact surface 192 of the perianal support member 190 that extends onto the compression elements 198, 199. In other embodiments, the marker 205 may have any of a variety of shapes or patterns, including, without limitation, oblong, round, ovoid, target-shaped, or striped. In some embodiments, the marker 205 may comprise a window (e.g., either an open cut-out from the perianal support member 190 or a solid window formed of a suitably clear material) that allows the user to see through the perianal support member 190 during and after placement of the perianal support member 190 on the patient 10. In other embodiments having a clear or translucent contact surface 192, where the user may visually observe the spread of tissue contacting the contact surface 192 through the member 190, the marker 205 may comprise a manually drawn marking on the contact surface 192 or the inner surface 196 that marks a particular anatomic reference structure, point, margin, or distance for the user. In some embodiments, the user may mark the a first location on the inner surface 196 to indicate the initial margin of tissue contacting the contact surface 192 after the initial placement of the perianal support member 190 on the patient 10, and then mark a second location on the inner surface 196 to indicate the spreading margin of tissue contacting the contact surface 192 after the change in pressure relationships between the contact surface 192 and the patient 10. The user can measure the distance between the first and second markings to evaluate the extent of tissue distension and pressure changes and analyze the progress of labor.

In use, the user can align the marker 205 with a body reference marker, such as the anus or anal orifice 26 (shown in FIG. 1). This may help ensure that the perianal support member 190 is properly located to apply focal pressure through the focusing pressure element 200 in the correct area (e.g., to stimulate the pushing reflex and/or give the patient a physical focal point to direct the pushing effort), to properly shape the exit portion of the vaginal canal to facilitate the baby's egress from the birth canal, and/or to support or treat perianal tissue while maintaining suitable spacing from the vaginal opening.

The other embodiments of perianal support members described herein (e.g., perianal support members lacking the focusing pressure element 200) may also include a marker 205. Application of the perianal support member 190 on the patient 10 is described further below in relation to FIG. 16B.

Figure 9B:
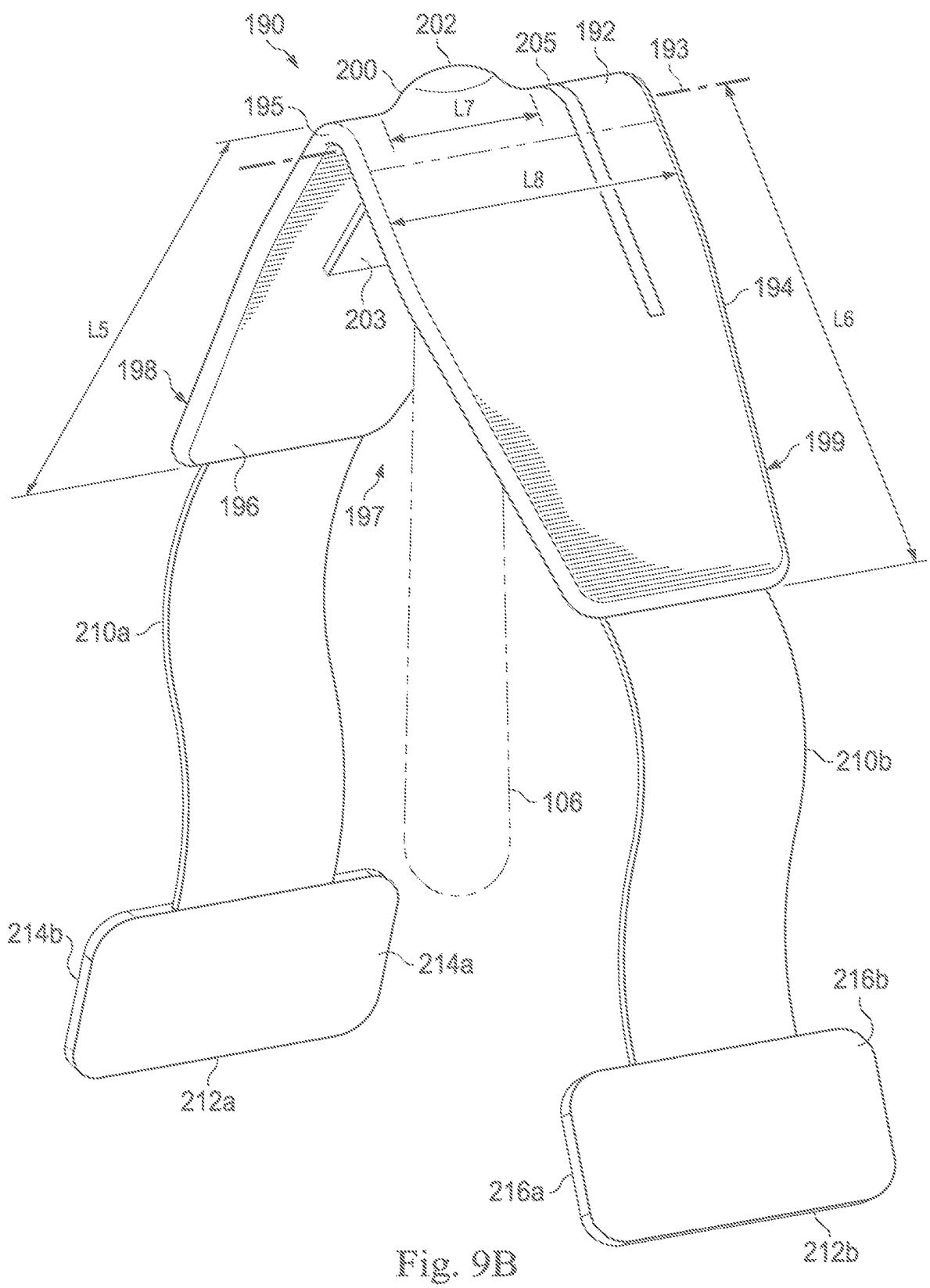
FIG. 9B illustrates a perspective view of the exemplary perianal support member shown in FIG. 9A including exemplary securing members according to one embodiment of the present disclosure.

FIG. 9B illustrates a perspective view of the exemplary perianal support member shown in FIG. 9A including two securing members 210a, 210b that terminate in anchor pads 212a, 212b. The anchor pads 212a, 212b are shaped and configured to be removably attached to the buttocks 14, 15 (e.g., within the gluteal cleft 13) of the patient 10 (in a similar fashion as shown in FIG. 2C). In some embodiments, the anchor pads 212a, 212b may be adhesively attached to the patient 10. In the pictured example, the securing members 210a, 210b are fixedly coupled to the compression elements 198, 199 and the anchor pads 212a, 212b, respectively. In some examples, the securing members 210a, 210b include a first half of a releasable fastening system coupled to the compression elements 198, 199, such as a hook and loop system or a releasable adhesive system. In the illustrated embodiment, the anchor pads 212a, 212b have a generally rectangular shape that is shorter in length and wider than elongated securing members 210a, 210b. The shape of the anchor pads 212a, 212b is shown for illustration purposes and may take any form that is suitable for fixing to a patient or inanimate object, as well as joining to the elongated fixation member. Each anchor pad 212a, 212b includes a first surface 214a, 214b having an adhesive surface (substantially similar to the adhesive surface 642 described in more detail with relation to FIG. 15) adapted for joining to the patient's skin or some inanimate object. The opposing surface 216a, 216b (substantially similar to the surface 644 described in more detail with relation to FIG. 15) includes the second half of the fastening system, which couples to the securing member 210a, 210b, respectively. In some embodiments, at least a portion of a surface of the first surface 214a, 214b includes an adhesive coating that can fix the securing member to another object. In one embodiment, the adhesive coating is adapted for releasably adhering to a patient's skin.

Figure 10:
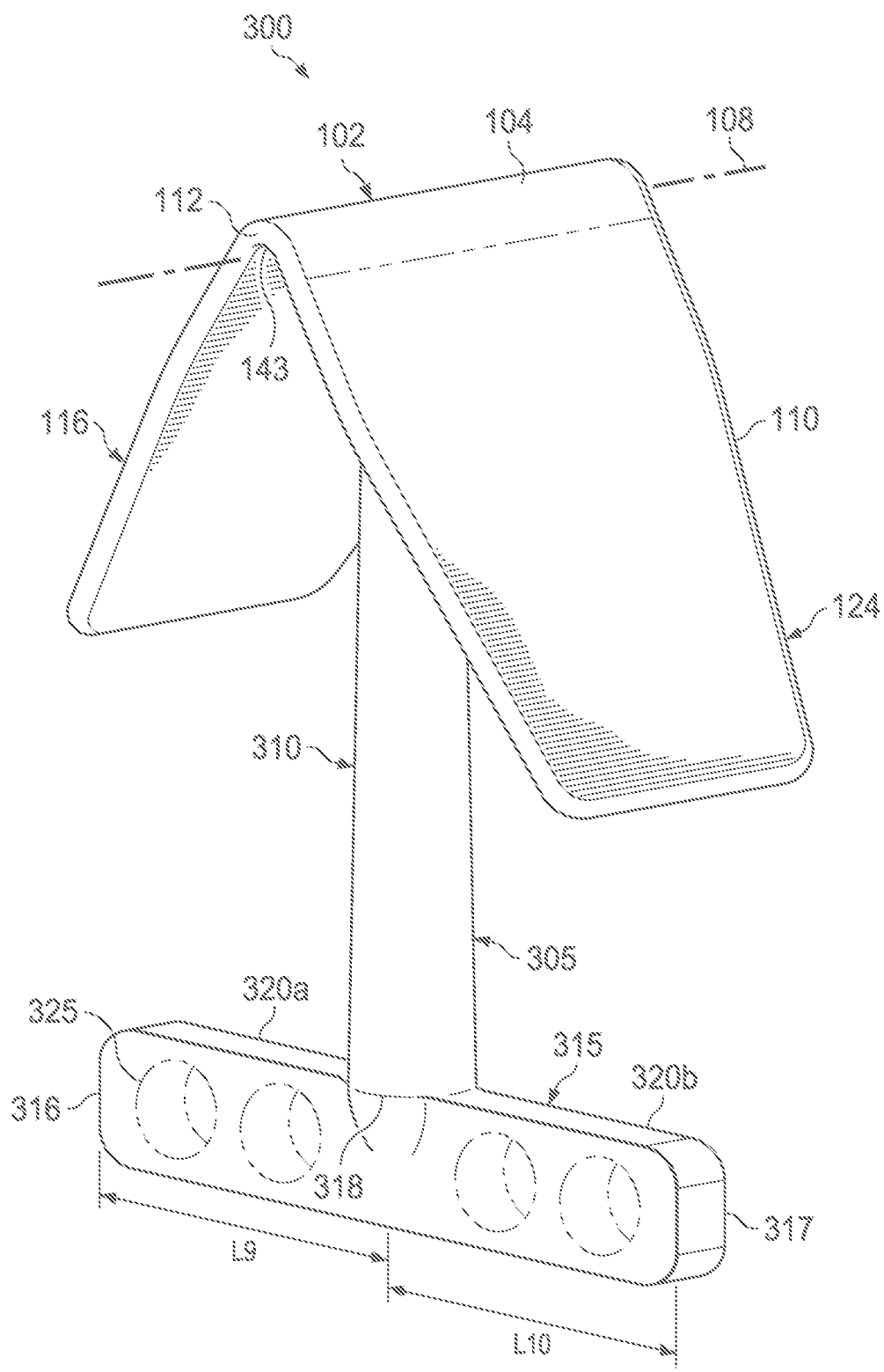
FIG. 10 illustrates an exemplary labor assistance system including the perianal support member shown in FIG. 1 coupled to an exemplary grip according to one embodiment of the present disclosure.
Figure 11:
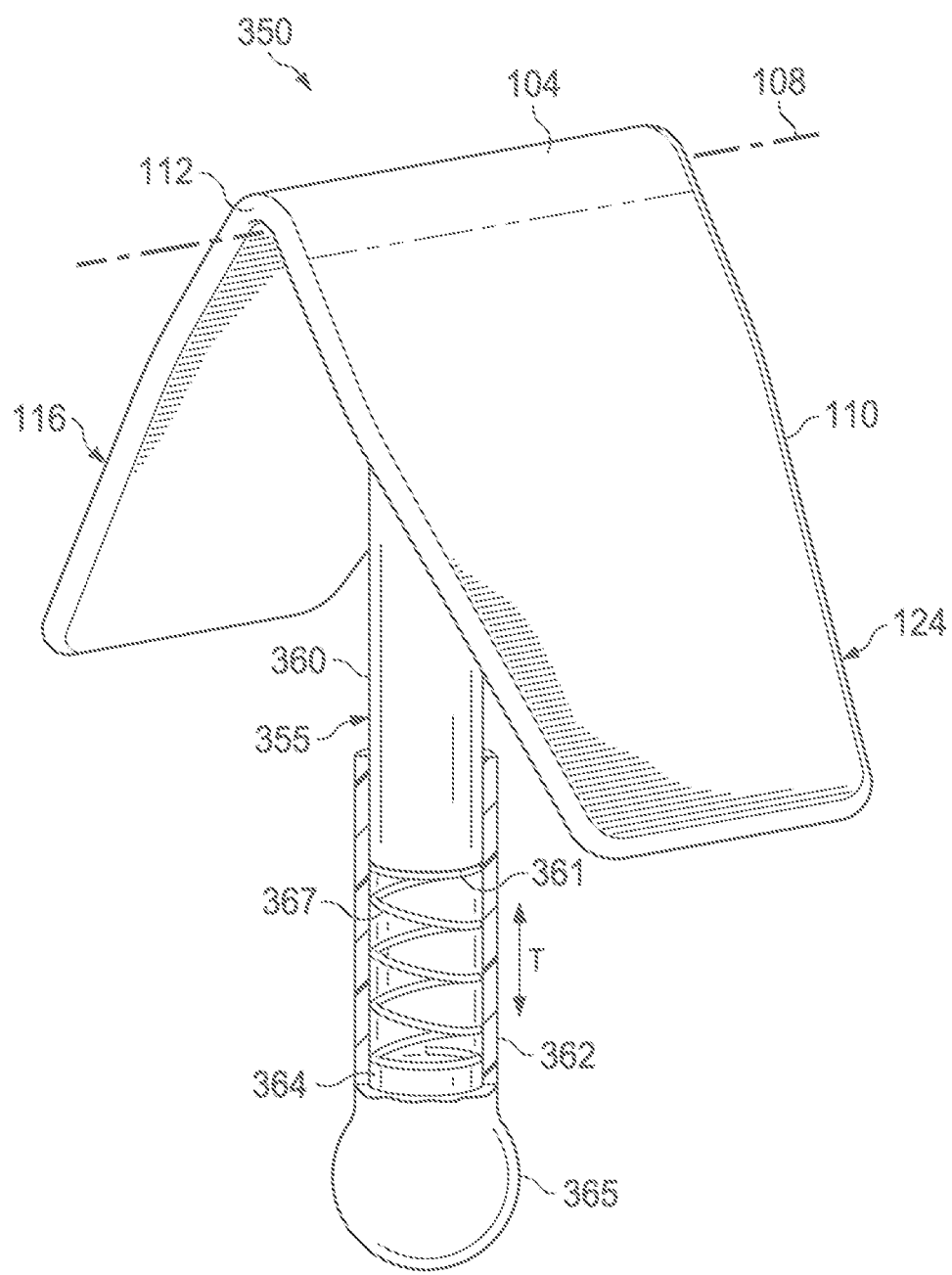
FIG. 11 illustrates an exemplary labor assistance system including the perianal support member shown in FIG. 1 coupled to an exemplary grip according to one embodiment of the present disclosure.
Figure 12:
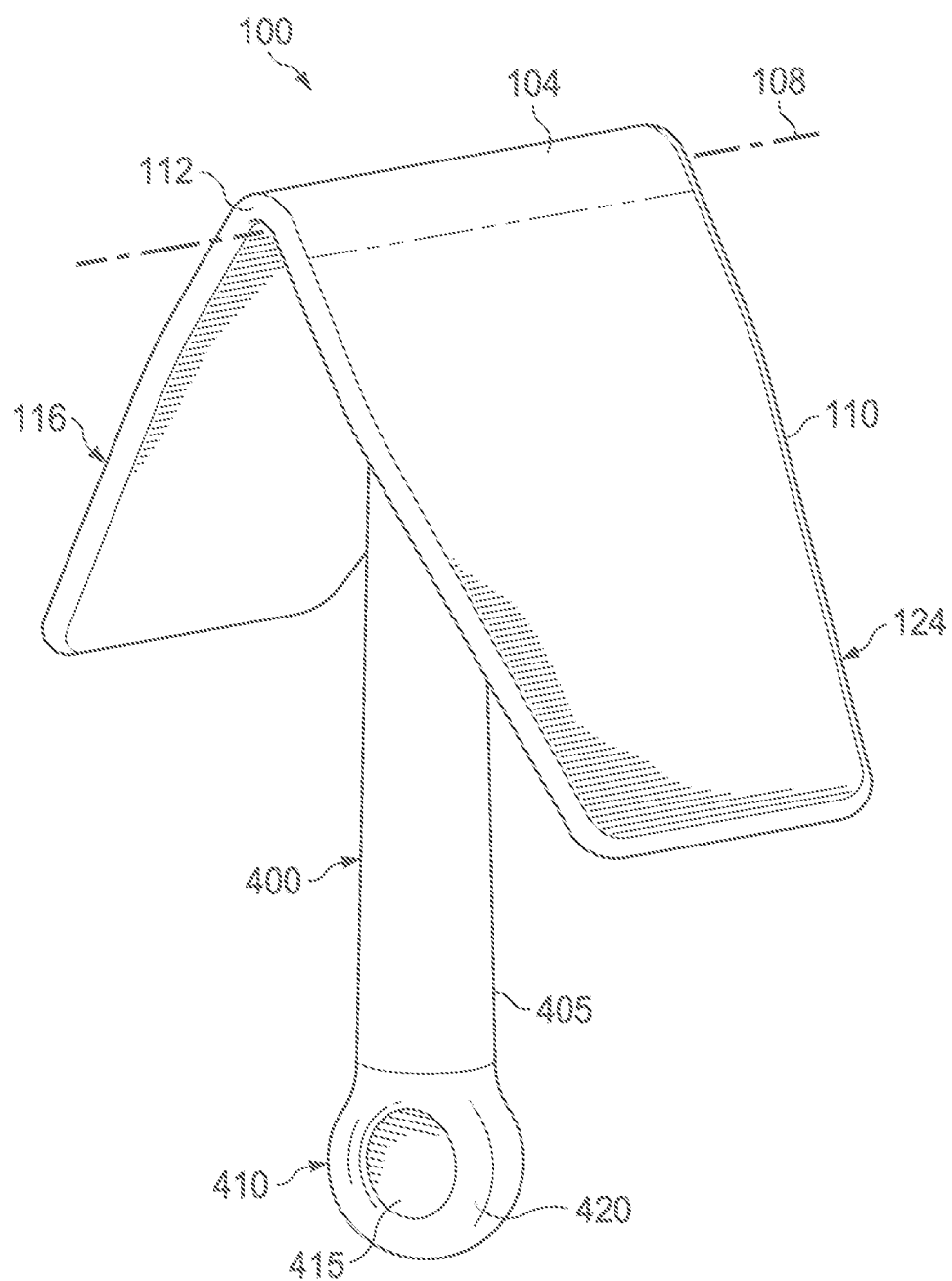
FIG. 12 illustrates an exemplary labor assistance system including the perianal support member shown in FIG. 1 coupled to an exemplary grip according to one embodiment of the present disclosure.

In addition to including different types of perianal support members, as described above, various embodiments of the labor assistance systems may include different types of grips. In this regard, FIGS. 10-12 illustrate the perianal support member 102 coupled to a variety of different exemplary grips, and FIGS. 13 and 14 illustrate a perianal support member 455 coupled to a variety of different exemplary grips. The different types of grips are meant to be illustrative only, and are in no way limiting. Other types of grips are contemplated. In addition, it should be understood that each of the different perianal support members and grips described herein can be combined in any of a variety of combinations to create labor assistance systems having different configurations and pressure-application characteristics.

FIG. 10 illustrates an exemplary labor assistance system 300 including the perianal support member 102 coupled to an exemplary grip 305. The grip 300 is substantially similar to the grip 106 described above except for the differences described herein. The grip 300 is shaped as a "T-bar" including a shaft 310 and a bar 315. The bar 315 extending from an end 316 to an end 317, and is attached to the shaft 310 at a midpoint 318 to form two sections 320a and 320b on either side of the shaft 310. In the pictured embodiment, the section 320a has approximately a same length L9 as a length L10 of the section 320b. In other embodiments, the bar 315 may be positioned such that the sections 320a, 320b are not of equal lengths. In some embodiments, bar 315 may be attached to the shaft 310 to form an "L-bar" shape (e.g., with the shaft 310 meeting the bar 315 at one end 316 or 317 instead of the midpoint 318). In the pictured embodiment, the bar 315 is disposed substantially perpendicular to the shaft 310. In other embodiments, the bar 315 may be disposed at an oblique angle with respect to the shaft 310. The bar 315 forms a handle for the user to hold while positioning and maintaining the labor assistance system 300 against the patient 10. For example, in some instances, the user may wrap his or her fingers around the sections 320a, 320b to obtain a secure grasp of the grip 305.

In some embodiments, the bar 315 (and/or the shaft) may include grip-enhancing features that enhance the graspability of the grip 305 such as, by way of non-limiting example, through holes 325 that enable a portion of the user's hand or fingers to extend therethrough. In other embodiments, the bar 315 (and/or the shaft 310) may include grip-enhancing features such as, by way of non-limiting example, indentations or protrusions that allow a portion of the user's hand or fingers to conform to or rest within. In other embodiments, the bar 315 (and/or the shaft 310) may be coated with polyurethane or other friction enhancing material to allow the patient to comfortably grip the grip 305 and provide pressure. Such grip-enhancing features may be found in any of the variety of grips described herein.

FIG. 11 illustrates an exemplary labor assistance system 350 including the perianal support member 102 coupled to an exemplary grip 355. The grip 355 is substantially similar to the grip 106 described above except for the differences described herein. The grip 355 includes an inner shaft 360 received within a hollow cylindrical portion of outer shaft 362 such that the inner shaft can telescope within the outer shaft. A spring 367 is positioned within the hollow cylindrical portion of the outer shaft and is compressed between inner shaft end 361 and outer shaft shoulder 364. The outer shaft 362 terminates in a knob 365. The knob 365 forms a graspable portion for the user to hold while positioning and maintaining the labor assistance system 350 against the patient 10. For example, in some instances, the user may wrap his or her hand around the knob 365 to obtain a secure grasp of the grip 355 while positioning and maintaining the labor assistance system 350 in pressurized engagement with the patient 10. In some instances, the knob 365 may be shaped and sized to comfortably fit in an average user's palm. The spring has a stiffness that maintains the amount of force the user can apply to the patient even at multiple knob position along the directions of arrow T. For example, if the user applies significant force to knob, the force will overcome the spring force and the knob will move in the direction of arrow T toward the patient. If the user's hand moves slightly away from the patient, the spring will move the knob away from the patient in the direction of arrow T and maintain substantially constant pressure on the patient even if the user's hand moves in and out in the directions of arrow T.

FIG. 12 illustrates an exemplary labor assistance system 400 including the perianal support member 102 coupled to an exemplary grip 405. The grip 405 is substantially similar to the grip 106 described above except for the differences described herein. The grip 405 includes a shaft 405 that terminates in a tab 410 having a central portion 415 and a raised rim 420. The tab 410 forms a graspable portion for the user to hold while positioning and maintaining the labor assistance system 400 against the patient 10. For example, in some instances, the user may wrap his or her fingers around the tab 410 to obtain a secure grasp of the grip 405 while positioning and maintaining the labor assistance system 400 in pressurized engagement with the patient 10. In some embodiments, the tab 410 forms an annular ring and the central portion 415 forms an aperture through which a user may pass one or more fingers. In other embodiments, instead of an aperture, the central portion 415 forms a central depression encircled by the raised rim 420.

FIG. 13 illustrates an exemplary labor assistance system 450 including the exemplary perianal support member 455 coupled to an exemplary grip 460. The perianal support member 455 is substantially similar to the perianal support member 102 described above except for the differences described herein. In particular, the perianal support member 455 includes a more rounded contact surface 465 and internal contact surface 470 than the contact surface 104 and internal contact surface 143 of the perianal support member 102. The grip 460 comprises an elongate, hollow tube that is coupled to the internal contact surface 470. In some embodiments, the grip 460 may extend the entire length L10 of the internal contact surface 470, which extends from an anterior edge 472 to a posterior edge 474. In other embodiments, the grip 460 may extend only partially along the length L10. For example, in some embodiments, the grip 460 may not extend to the anterior edge 472 and/or the posterior edge 474. In the pictured embodiment, the grip 460 forms a hollow cylinder having a passageway 475, through which the user may extend one or more fingers. Although the pictured embodiment shows the grip 460 having a circular side profile (e.g., the circular side profile of a cylindrical tube) the grip 460 may form a tube having any of a variety of side profile shapes. The grip 460 extends along the midline axis 108. In use, a user may slide one or more fingers through the passageway 475 and apply pressure towards the contact surface 465 to position and maintain the labor assistance system 400 against the patient 10. For example, in some instances, the user may push his or her fingers in the direction of the arrow A1 within the passageway 475 to maintain the labor assistance system 400 in pressurized engagement with the patient 10. In some embodiments, the grip 460 may form a tunnel or channel 480 through the perianal support member 455 through which a user may pass one or more fingers (instead of comprising a separate tubular element as shown in FIG. 13). In such embodiments, the perianal support member 455 may be thicker than shown in FIG. 13 (e.g., with a greater distance between the contact surface 465 and the internal contact surface 470).

FIG. 14 illustrates an exemplary labor assistance system 500 including the exemplary perianal support member 455 coupled to an exemplary grip 510. The perianal support member 455 includes an inner surface 505 disposed opposite an outer surface 508, which extends across the perianal support member 455 to include the contact surface 465. The grip 510 comprises a curved support structure or compliant pad that is coupled to the inner surface 505. In some embodiments, the grip 510 substantially mimics the shape and contour of the perianal support member 455. For example, in the pictured embodiment, the grip 510 forms a curved, wedge-shaped structure including an upper surface 515 that has the same curvature and contour as the inner surface 505 of the perianal support member 455. In some embodiments, the grip 510 may extend the entire length L10 of the internal contact surface 470, which extends from the anterior edge 472 to the posterior edge 474. In other embodiments, the grip 510 may extend only partially along the length L10. For example, in some embodiments, the grip 510 may not extend to the anterior edge 472 and/or the posterior edge 474. Although the pictured embodiment shows the grip 510 having a side profile that substantially mimics the side profile of the perianal support member 455 (e.g., a wedge or curving V-shaped side profile), the grip 510 may have any of a variety of side profile shapes provided that the upper surface 515 is configured to contact the inner surface 505 of the perianal support member 455.

In use, a user may press one or more fingers against a lower surface 520 of the grip 510 and apply pressure towards the contact surface 465 to position and maintain the labor assistance system 400 against the patient 10. For example, in some instances, the user may push his or her fingers in the direction of the arrow A2 to maintain the labor assistance system 400 in pressurized engagement with the patient 10. In some embodiments, the grip 510 comprises a pad of compliant material that conforms or molds to the pressure applied by the user's fingers. In other embodiments, the grip 510 comprises a pad of non-compliant material. In some embodiments, the grip 510 may form an integral extension of the perianal support member 455 (instead of comprising a separate element as shown in FIG. 14). In some embodiments, the grip 510 can provide additional structural support for the perianal support member 455 as the user pushes the contact surface 465 against the patient 10. In some embodiments, the grip 510 can help the perianal support member 455 better conform to the patient 10, particularly when the contact surface 465 includes a conformable material. In some embodiments, the labor assistance system 500 also includes a handle-like grip (e.g., the grip 106) coupled to the grip 510.

In some embodiments, contact surface 465 includes a conformable material. Details of the types of materials and certain properties that may form contact surface 465 are described in detail with respect to the embodiment of FIG. 7. In at least one aspect, contact layer 465 comprises a material that deforms under compressive force of 1-10 pounds of pressure applied to the grip, and more preferably deforms at loads of 3-7 pounds of pressure applied to the grip. These same properties may be experienced with use of pad 173 described with respect to FIG. 7.

Figure 15:
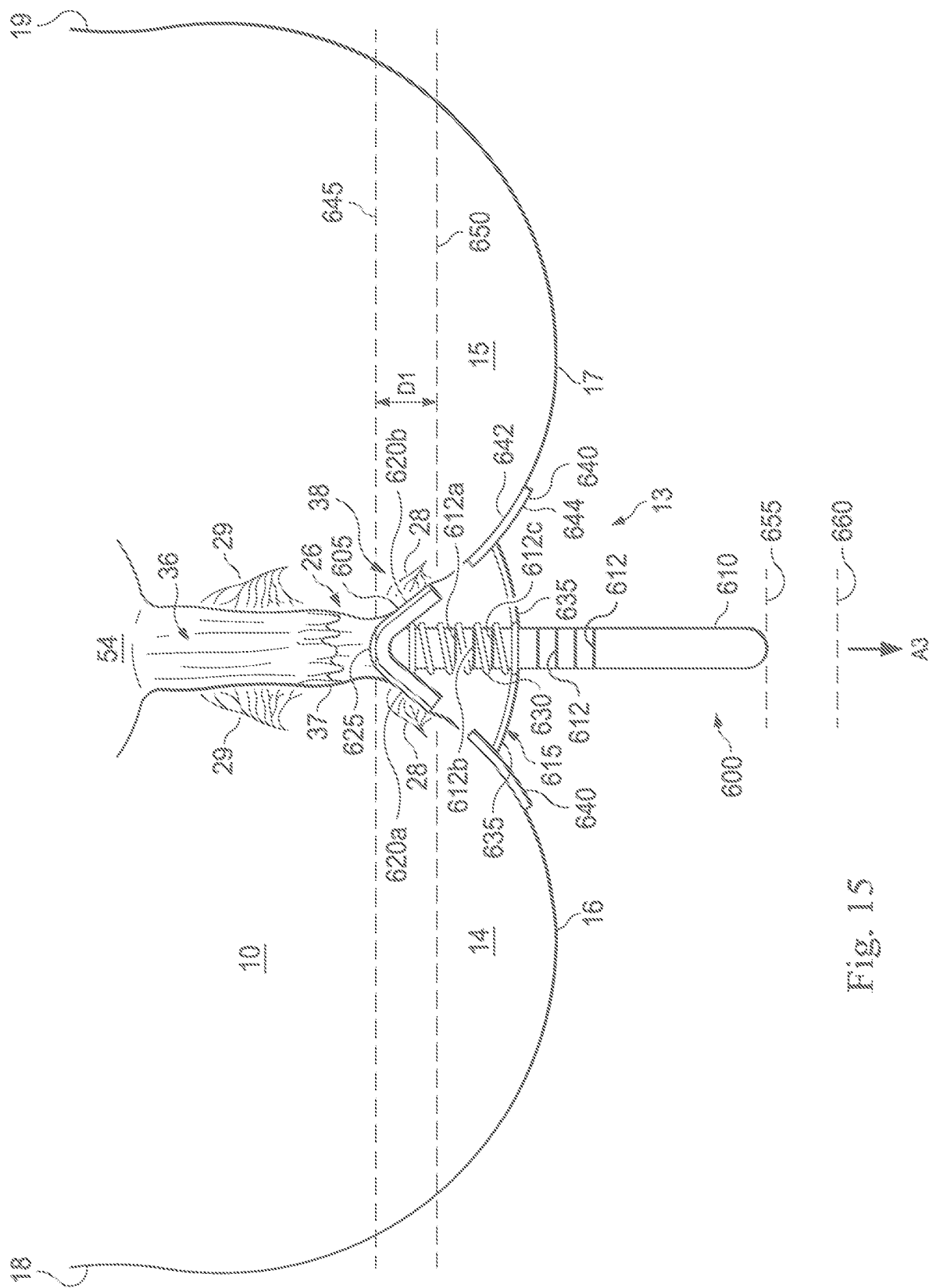
FIG. 15 illustrates an exemplary labor assistance system including an exemplary push evaluation system positioned on the patient 10 according to one embodiment of the present disclosure.

FIG. 15 illustrates an exemplary labor assistance system 600 positioned within the gluteal cleft 13 of the patient 10. In particular, FIG. 15 shows the labor assistance system 600, including a perianal support member 605 and a grip 610, and a push evaluation system 615. In some embodiments, the push evaluation system 615 is integrally formed with components of the labor assistance system 600 discussed above. That is, in some embodiments, the push evaluation system 615 is a part of the labor assistance system 600. In other embodiments, the push evaluation system 615 is associated with the support system 100 in a manner enabling the push evaluation system 615 to monitor or detect the pressure on the labor assistance system 600 or on the patient. The perianal support member 605 is substantially similar to the perianal support member 102 except for the differences described herein. For example, the perianal support member 605 is sized and shaped to fit within the gluteal cleft 13 of the patient 10. In particular, in the pictured embodiment, compression members 620a, 620b are shaped and sized to extend within the gluteal cleft 13 without extending past the gluteal cleft 13. The grip 610 may be substantially similar to the grip 106 except for the differences described herein. For example, the grip 610 in the pictured embodiment is coupled to the push evaluation system 615. The grip 610 includes a series of markings 612. The markings 612 may be used to indicate the amount of anal displacement, the amount of displacement of the perianal support member 605, and/or the amount of force or pressure applied to the perianal support member 605.

The push evaluation system 615 is shaped and configured to measure and convey the extent of the pushing force applied by the patient 10 on a contact surface 625 of the perianal support member 605. The push evaluation system 615 may be configured and arranged to detect changes in pressure, stress, or strain, either directly or indirectly, that may be indicative of the amount of force being applied on the labor assistance system 600 by the patient 10. The push evaluation system 615 may be associated and configured with other components of the labor assistance system 600, such as the perianal support member 602 or the grip 610. For example, the push evaluation system 615 in the pictured embodiment is coupled to the grip 610. For example, the push evaluation system 615 may directly measure pressure or force upon the perianal support member 605 using pressure sensors, or may indirectly measure pushing force by detecting and conveying changes in the shape, structure, or arrangement of various components or elements making up the labor assistance system 600.

In the pictured embodiment, the push evaluation system 615 comprises a spring-loaded device including a spring 630 having two securing members 149a that terminate in anchor pads 149b. The anchor pads 149b are shaped and configured to be removably attached to the buttocks 14, 15 (e.g., within the gluteal cleft 13) of the patient 10. In some embodiments, the anchor pads 149b may be adhesively attached to the patient 10. In the pictured example, the securing members 149a are fixedly coupled to the spring 630 and the anchor pads 149b. In some examples, the securing members 149a include a first half of a releasable fastening system coupled to the spring 630, such as a hook and loop system or a releasable adhesive system. In the illustrated embodiment, the anchor pads 149b have a generally square shape that is shorter in length and wider than elongated securing members 149a. The shape of the anchor pad is shown for illustration purposes and may take any form that is suitable for fixing to a patient or inanimate object, as well as joining to the elongated fixation member. Each anchor pad 149b includes a first surface 642 having an adhesive surface adapted for joining to the patient's skin or some inanimate object. The opposing surface 644 includes the second half of the fastening system, which couples to the securing member 149a. In some embodiments, at least a portion of a surface of the first surface 642 includes an adhesive coating that can fix the securing member to another object. In one embodiment, the adhesive coating is adapted for releasably adhering to a patient's skin.

The push evaluation system 615 is configured to monitor uterine contractions and pushing by the patient by reflecting the force and/or pressure applied on the perianal support member 605 by the anal orifice 26 and the perianal tissue 38. That is, during contractions, the push evaluation system 615 described herein may be configured to detect a change in pushing force and pressure that occurs due to muscle displacement or distention of the perianal tissue (e.g., caused by the contractions and pushing effort of the patient 10). During labor, the contractions of the uterus, along with movement of the baby's head as a result of the uterine muscles, physically displace the perianal tissue. When the perianal tissue is supported by the perianal support members described herein, the result is less perianal tissue displacement and an increase in net pressure and force against the contact surface 625 of the perianal support member 605. These increases in pressure against the contact surface 625 can be detected using the push evaluation system 615. In particular, as the pushing force increases toward the labor assistance system 600, the perianal support member 605 will move in the direction of the force as indicated by the arrow A3. As the perianal support member 605 moves a distance D1 from a first position 645 to a second position 650 in response to the displacement of the perianal tissue, the grip 610 can slide within the spring 630 in the direction of the arrow A3 from a third position 655 to a fourth position 660. Although the movement of the grip 610 may compress the spring 630, the securing members 149a and the anchor pads 149b remain substantially fixed in place relative to the patient 10. The greater the pushing force and/or effort of the patient 10, the greater the distance D1 the perianal support member 605 will shift away from the line 645.

This distance D1 and pushing force may be reflected by the markings 612 on the grip 610 relative to the securing members 149a. For example, in one embodiment, when the contact surface 625 of the perianal support member 605 is positioned relative to the anal orifice 26 at the first position 645, the marking 612c may be level with or adjacent to the securing member 149a. As the patient pushes, the perianal support member 605 may shift downward by the distance D1 until the contact surface 625 is positioned at the second position 650, simultaneously shifting the grip 610 the distance D1 from the line 655 to the line 660. When the grip 610 is positioned at the line 660, the marking 612a may be level with or adjacent to the securing member 149a, indicating the change in force and/or pressure applied to by the patient's pushing upon the perianal support member 605. Accordingly, in addition to measuring the pushing force and pressure statically upon application of the labor assistance system 600, the push evaluation system 615 may be used to monitor dynamic force and pressure by detecting changes in force and pressure on the labor assistance system 600 resulting from uterine contractions ad maternal pushing.

In addition, by monitoring the changes in pressure on the perianal tissue by the perianal support member 605 that occur during a push, the pressure detection systems may be able to provide a pressure indication of the strength of a push. Accordingly, during the birthing process, the patient and/or the healthcare provider may observe the system 615 to determine the strength of a push. The position of the markings 612 on the grip 610 relative to the securing members 149a may suggest whether or not the patient is effectively pushing the baby toward the vaginal opening during a contraction. Moreover, if the grip 610 compresses the spring 630 to the extent that the position of the markings 612 relative to the securing members 149a can no longer change, the user may be alerted to a pushing effort by the patient 10 in an unsafe force or pressure range. This may indicate that pressure on the perianal tissue should be reduced, and the user may instruct the patient 10 to halt pushing and/or remove the labor assistance system 600 from contact with the patient 10. Therefore, this condition alerts the user and patient 10 to either cease the pushing contractions and/or to reposition or remove the labor assistance system 600. As such, the push evaluation system 615 may provide positive user feedback on dynamic pressure changes indicative of the success or lack thereof of pushing associated with contractions. It's worth noting that the labor assistance system 600 may be retained in position on the patient 10 both during the static support phase and the dynamic support phase of the birthing process.

The push evaluation systems disclosed herein may enable a health care provider of the patient to apply the labor assistance system with at least a proper amount of pressure to provide therapeutic support to the patient during childbirth. Accordingly, by evaluating the strength and effectiveness of the patient's pushing and adjusting the position and pressure application of the labor assistance system accordingly, utilizing the systems disclosed herein may reduce the incidence of a number of complications, including for example and without limitation, pelvic floor incompetence or dysfunction, organ prolapse, incontinence secondary to pressure and stretching exerted on bladder and bladder neck, over stretching, perineum tears and lacerations, forceps use, and hemorrhoids.

Returning now to FIGS. 1 and 2, in use the user (e.g., the patient 10, a health care provider, or another) positions the patient 10 to expose the perianal region 38. During the child birthing process, the patient 10 may be positioned in stirrups attached to a delivery table (not shown). The labor assistance system 100 is then moved adjacent the gluteal cleft 13 between the buttocks 14 and 15. The support system 100 is positioned such that the midline axis 108 of the perianal support member 102 is substantially aligned with the patient's midline within the sagittal plane. Referring to FIG. 1, the perianal support member 102 is advanced in the direction of arrow A4 toward the anal orifice 26 (generally within the sagittal plane toward the head of the patient 10) to bring the contact surface 104 into contact with the perianal tissues 38. Continued advancement of the perianal support member 102 toward the anal orifice 26 applies pressure through the contact surface 104 and the compression members to the perianal tissues. The user may hold the grip 106 to position the perianal support member 102 within the gluteal cleft 13 and to advance the perianal support member 102 against the perianal tissues 38. In one aspect, the healthcare provider may place at least one finger within the access cavity 136 and preferably against the inner surface 132 to further advance the device against the anal orifice 26.

The user may utilize the pressure feedback (e.g., tactile or haptic feedback) associated with the labor assistance system 100, the push evaluation system 615, and/or an intrauterine contraction monitor to sense whether the patient 10 is or should be actively pushing. In one aspect, the labor assistance system 100 is initially positioned to be spaced from or only in touching engagement with the patient 10 without creating pressure when the patient 10 is not experiencing a contraction. As a contraction occurs or the patient 10 pushes, the perianal tissues 38 will tend to protrude thereby engaging the system 100 with a pressure that can be felt by the mother through tactile or haptic feedback and/or sensed by the push evaluation system 615. With continued pressure applied by the user to the grip 106 and/or the inner surface 132 of the labor assistance system 100, the patient 10 can feel increasing tactile pressure from the perianal support member 102 against which to focus her pushing effort and direct the force of her pushing.

The extent of tissue deformation surrounding the anal orifice 26 when the labor assistance system 100 is applied is a function of the patient anatomy, the amount of pushing force exerted by the patient 10, and the amount of compressive force applied in the direction of arrow A4 through the grip 106 during application of the system 100. As shown in FIG. 1, the maximum extent of perianal tissue engagement inwardly on the patient 10 in the sagittal plane is shown by the line 645. In one aspect, it is contemplated that pressure applied in the direction of arrow A4 moves the anal orifice 26 inwardly 1 cm to 3 cm. The compression elements 116, 124 exert tension forces generally in the direction of arrows A5 and A6, respectively. The compression elements 116, 124 are substantially rigid members capable of transmitting compressive forces to the perianal support member 102 and the perianal tissues 38. The compressive forces A5 and A6 are transmitted by substantially rigid compression elements 116, 124 and ultimately to the contact surface 104 to apply support and/or pressure to the perianal tissues in the direction of arrow A4. It will be appreciated that the lateral components of compressive forces applied in A5 and A6 help to maintain the position of the perianal support member 102 as well as tending to maintain the access cavity 136 in an open position. It will be understood that while compression elements 116, 124 are sufficiently rigid to transmit compressive force toward the contact surface 104, in one embodiment they are flexible, at least laterally, to bow or bend in response to forces applied by the buttocks 16, 17.

As shown in FIG. 1, a distance D2 between the anal orifice 26 and the buttocks crown 16 is less than a distance D3 between a distal end 670 of the compression member 116 and the anal orifice 26. Thus, tension applied to the grip 106 is transferred through the substantially rigid compression elements 116, 124 to exert a compressive force on the contact surface 104 in the direction of arrow A4. In other embodiments, the distance D3 may be greater than the distance D4 (e.g., as shown in FIG. 15). It will be appreciated that with the illustrated embodiment, the user may maneuver the grip 106 to reposition the perianal support member 102 and adjust the compressive force applied through the grip 106 to the contact surface 104 by decreasing or increasing the force applied through the grip 106 in the direction A4 toward the patient 10.

The extent of tissue deformation surrounding the anal orifice 26 is a function of the patient anatomy and of the amount of compressive force applied during application of the labor assistance system 100. In one aspect, the health care provider makes initial contact with anal orifice 26 and then applies pressure in the sagittal plane (generally toward the patient's head) to advance the device 1 cm to 3 cm. This advancement of the device approximately 1 cm to 3 cm compresses the perianal tissue and thereby supports the tissue to inhibit distention as the patient 10 pushes during the birthing process. It will be appreciated that with the illustrated embodiment, the user may reposition the device and adjust the compressive force applied through the grip 106 and the compression members 116, 124 to the contact surface 104 by adjusting his or her grasp on the grip 106 to adjust the strength and directionality of force and/or pressure applied through the contact surface 104.

In an alternative approach, the contact surface 104 is positioned in engagement with the anal orifice 26 with little if any compressive force applied to deform the perianal tissue 38. The perianal support member 102 is then manually maintained in position using the grip 106 as described above. With this technique, the labor assistance system 100 will resist movement of the device in a direction generally away from the patient's head and will thereby support the perianal tissue to maintain its position. In a further feature, the push evaluation system 615 may indicate outward pressure on the perianal tissue to provide feedback to the patient 10 and/or other users on successful pushing during contractions.

Still referring to FIGS. 1 and 2, with the system 100 in position, a user may position one or both hands within the access cavity 136 extending into the gluteal clef 13. In this manner, the hands may be below the lowest portion of the vaginal opening 11 as the head of the baby 12 passes out of the vagina. Thus, the hand within the access cavity 136 is positionable less than 1 cm from the mother's vaginal opening or perineum so the healthcare provider may support the head of the baby as is it is being born. As shown in FIG. 2, the position of the anterior edge 112 of the perianal support member 102 also allows access to the tissue immediately posterior to the vaginal opening 11 in the event an obstetric maneuver, such as an episiotomy, manual manipulation of the fetus, etc., is necessary. In some instances, the anterior edge 112 of the perianal support member 102 may be curved or concave to allow better access to the vaginal opening 11 while the labor assistance system 100 remains in position against the perianal tissues. Further, as discussed above, in some instances, the perianal support member 102 can be quickly repositioned or removed, an obstetric maneuver can be performed, the perianal support member 102 is repositioned in a supporting position adjacent the anus, and its position can be maintained by manually handling the grip 106.

Additionally, in the illustrated embodiments, the perianal support member 102 of the labor assistance systems is sized and positioned with respect to patient 10 to allow for the passage of a child through the birthing canal during childbirth. The labor assistance system 100 is positioned on the patient 10 such that the perianal support member 102 does not extend along the patient midline 108 in the gluteal cleft 13 with the potential for interference with the birthing process, but instead extends substantially laterally from the patient's midline (e.g., the compressive members 116, 124 extend laterally from the midline axis 108). It is contemplated that the perianal support member 102 may be placed to support more or less of the external perineum region located between the anal orifice 26 and the vaginal opening 11 depending on the user's judgment and the progress of the child birthing process. Still further, it is contemplated that an exemplary labor assistance device having an elongated anterior to posterior width W2 (as shown in FIG. 3) may be positioned to support at least a portion of the perianal tissue and the vaginal tissue during the labor process. In some embodiments, the anterior edge 112 of the perianal support member may be curved toward the posterior edge 110 (e.g., having a concave profile) to allow for greater access to the vaginal opening 11 and provide ample room for the baby 12 to crown. It is anticipated that the system 100 will be repositioned posteriorly away from the vaginal opening prior to delivery of the child through the vaginal opening.

Figure 16A:
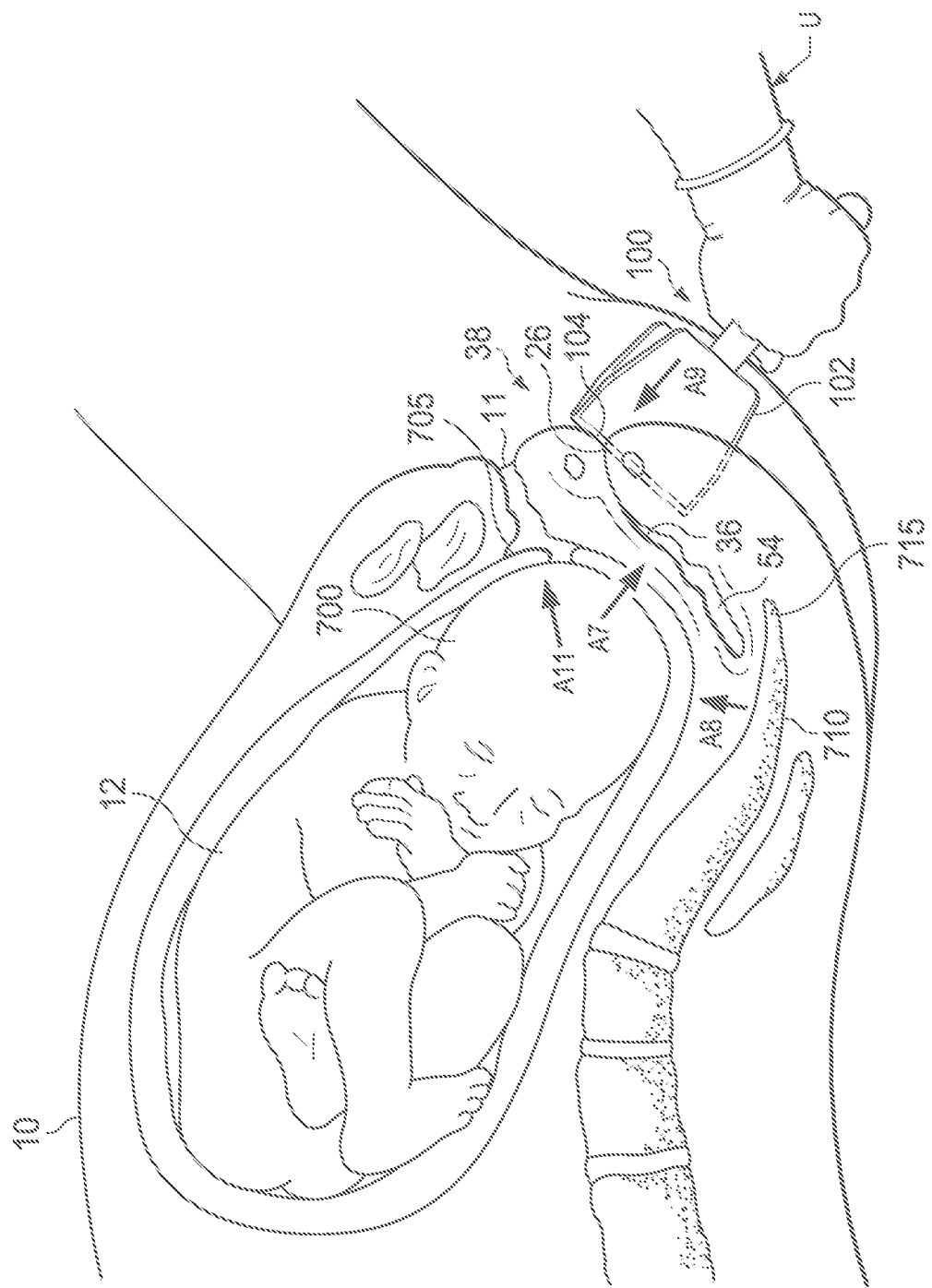
FIG. 16A illustrates a cross-sectional view of a patient in the sagittal plane and the labor assistance system taken along the lines 16-16 shown in FIG. 2.
Figure 16B:
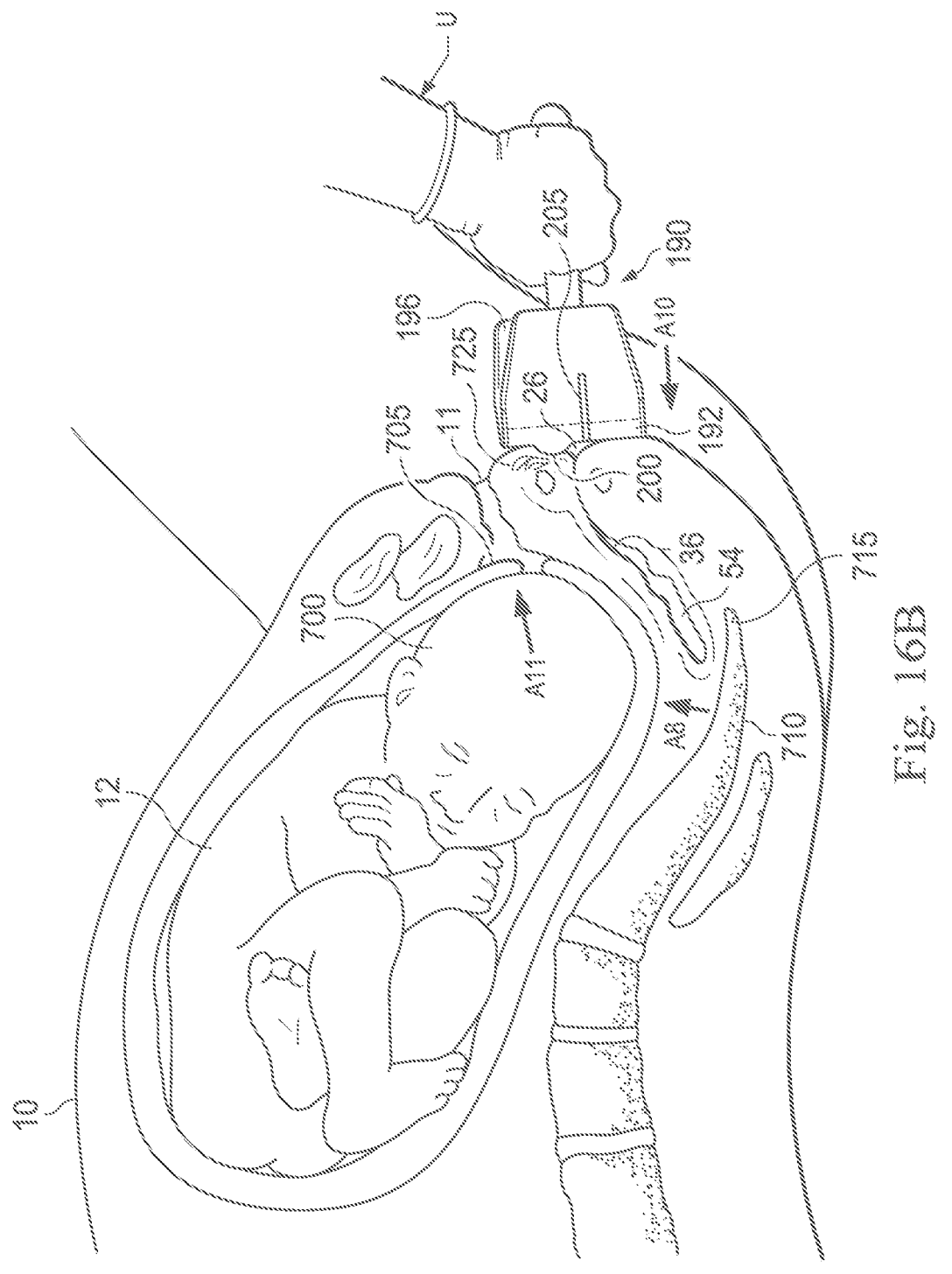

FIGS. 16A and 16B illustrate cross-sectional views of a patient 10 in the sagittal plane taken along the lines 16-16 shown in FIG. 2. FIG. 16A illustrates the perianal support member 102 positioned against the patient 10, and FIG. 16B illustrates the perianal support member 190 (described above in relation to FIG. 9A) positioned against the patient 10. In FIG. 16A, the labor assistance system 100 is shown held by a user U and positioned against the perianal region 38 of the patient 10. In other instances, the labor assistance system 100 may be secured to the patient 10 by means of securing members and anchor pads, as described above in relation to FIGS. 2B and 2C. For example, the perianal support member 102 may be secured to the patient 10 in a manner to apply pressure to the perianal and/or anococcygeal regions by securing members substantially similar to the securing members 149*a* and anchor pads substantially similar to the anchor pads 149*b* described above in relation to FIGS. 2B and 2C. Such securing members and anchor pads are not shown in FIG. 16A due to the difficulty of illustrating such an embodiment in the depicted view.

In FIG. 16A, the perianal support member 102 is positioned with the contact surface 104 in contact with the anal orifice 26. In one instance, the user U holds the grip 106 to position the perianal support member 102 against the perianal region 38 at an angle and with sufficient pressure to assist in shortening the second stage of labor. As shown in FIG. 16, uterine contractions and the patient's pushing force may act in the direction of an arrow A7, directing the baby 12 downwards but not necessarily toward the vaginal opening 11. The baby 12 is shown in a downward position with a baby's head 700 contacting the cervix 705. As the baby 12 progresses through the birth canal, the mother's anatomy assists in guiding the baby 12 along an optimal path toward the vaginal opening 11. For example, a sacrum 710, and, in particular, a coccyx 715, can provide an internal brace or scaffolding to provide counter pressure in the direction of an arrow A8 that can guide and/or shift the exit trajectory of the baby 12 toward the vaginal opening 11 in the direction of arrow A11 as the patient 10 pushes the baby 12 in the direction of the arrow A7.

Similarly, in some instances, the labor assistance system 100 may be used as an external guide or brace that provides counter pressure along the contact surface 104 to help guide the baby 12 along a desired path through the birth canal and toward the vaginal opening 11. In particular, the labor assistance system 100 can act as a sacral extension member or anococcygeal support member configured to provide counter pressure in the anococcygeal region (i.e., the region between the anus and the coccyx of the patient 10) in the direction of an arrow A9 against the pushing forces acting in the direction of the arrow A7. The contact surface 104 of the labor assistance system 100 can act as a relatively firm and selectively yielding external scaffolding that prevents the patient's pushing force from driving the baby's head 700 in a direction away from the ideal exit path towards the vaginal opening 11. For example, the patient's pushing force may direct the baby's head 700 towards the posterior of the patient 10 (e.g., towards the posterior rectal hiatus or rectum 36) instead of more anteriorly towards the vaginal opening 11. The sacrum 710 provides a natural guide or internal scaffold that assists in redirecting the baby's head 700 towards the vaginal opening 11. Like the sacrum 710, the labor assistance device 100 can act as a physical guide or external scaffold against the anococcygeal region that assists in redirecting the baby's head 700 towards the vaginal opening 11, especially once the baby's head 11 has descended past the sacral promontory 715. Unlike the sacrum 710, however, which is relatively stationary within the patient 10, the labor assistance system 100 can act as a dynamic guide to assist the baby's exit from the birth canal. In particular, as labor progresses and the baby's head 700 descends through the birth canal, the user may adjust the direction and strength of the counter pressure applied through the labor assistance system 100 against the anococcygeal and perianal regions by changing the strength and directionality of his or her grasp on the grip 106. Thus, the user may change the angle A9 as the angle A7 changes with the progression of labor to best guide the baby's head 700 through the birth canal.

In FIG. 16B, the perianal support member 190 is shown positioned against the perianal region 38 of the patient 10. In particular, the perianal support member 190 is positioned with the contact surface 192 in contact with the anal orifice 26, and the focusing pressure element 200 positioned against the perineum between the anal orifice 26 and the vaginal orifice 11. In one instance, the user U holds the grip 106 to position the contact surface 192 and the focusing pressure element 200 against the perianal region 38 (e.g., against a nerve or nerve bundle or nerve plexus 725 that may stimulate the patient's urge to push) at an angle and with sufficient pressure to assist in shortening the second stage of labor. In some embodiments, the user U may observe the position of the marker 205 in relation to the patient's anatomy (e.g., the anal orifice 26) to appropriately position the focusing pressure element 200 against the patient 10.

In embodiments having a clear or translucent contact surface 192 (or 102), the user U may observe, mark (on the inner surface 196 or 132), and/or measure the extent of tissue distention against the contact surface 192 or 102 upon initial placement of the device, and then observe, mark (on the inner surface 196 or 132), and/or measure the extent of tissue distention against the contact surface 192 or 102 after the change of pressure on the contact surface due to the voluntary or involuntary contractions of labor. The difference between the two measurements or the distance between the two markings may suggest the extent of the pressure changes occurring in the labor process and may serve as an indication of the progress of labor.

As shown in FIG. 16B, the application of counter pressure in the direction of arrow A10 through the contact surface 192 and/or the focusing pressure element 200 may augment or spur the patient's pushing force and aid the descent of the baby 12 in the direction of arrow A11 toward the vaginal opening 11. As labor progresses and the baby's head 700 descends through the birth canal, the user U may adjust the direction and strength of the counter pressure applied through perianal support member 190 and/or the focusing pressure element 200 by changing the strength and directionality of his or her grasp on the grip 106. Thus, the user U may change the angle A10 as the angle A11 changes with the progression of labor to best guide the baby's head 700 through the birth canal.

Figure 17:
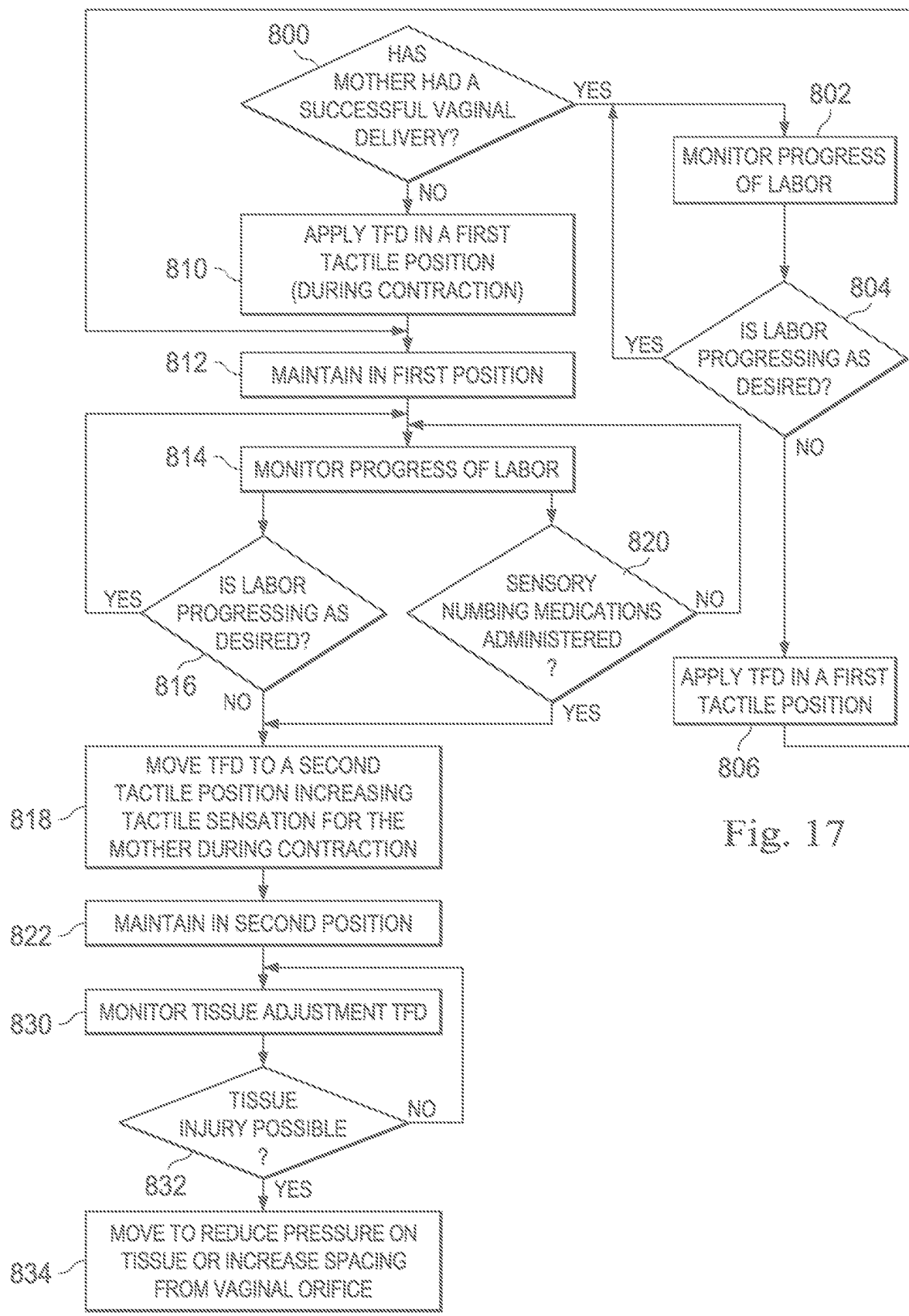
FIG. 17 illustrates a flow chart illustrating a method of utilizing an exemplary labor assistance system according to one aspect of the present disclosure.

In use, the user can position the patient 10 to expose the perianal region and vaginal opening 11. Referring now to FIG. 17, there is a shown a flow chart illustrating a method of utilizing a labor assistance system according to one aspect of the present disclosure to manage a mother's labor process to reduce the duration of second stage labor and increase the incidence of a vaginal delivery without increasing tissue damage to the mother. In general terms, the method includes applying a tactile or haptic feedback device (e.g., the labor assistance system 100) in engagement with the perianal tissue and monitoring the progression of labor during the second stage.

With respect to FIG. 17, in some instances, the method begins at step 800 by determining whether the expecting mother has previously delivered a child by a vaginal delivery. If the answer to this inquiry is yes, then at step 802, the progress of labor is monitored to determine if labor is progressing as desired at step 804. In one instance, the progression of labor can include the amount of movement of the child toward the vaginal opening over a given a period of time. In another instance, the progression of labor can include shortening or thinning of the cervix, the amount of cervical dilation, assessment of fetal position and/or descent (e.g., via digital assessment inside the vagina, via manual palpation of the abdomen, via visual observation, or via imaging), and the amount of movement of the child toward the vaginal opening in comparison to the number of contractions or successful pushes the mother has experienced. The determination of the progression of labor may be made by a healthcare provider monitoring the patient or by an electronic monitoring system receiving one or more inputs indicative of labor progression such as the strength and/or number of contractions, effective pushes, and movement of the child within the mother and/or overall time of labor. As long as labor is progressing as desired, the method continues with monitoring the progress of labor.

If labor is not progressing as desired in step 804, then the method progresses to the application of a tactile feedback device (TFD) in a first tactile position at step 806 which could include devices similar to any of the labor assistance system embodiments described above or any other device configured and applied to provide perianal tactile sensation to the patient. In some embodiments, the TFD may also supply haptic feedback to the user that is indicative of the extent of pressure applied on the TFD. A first tactile position can include applying a TFD in a pressure inducing and tissue compression engagement at a first pressure threshold, engagement with the perianal tissue without pressure inducement or tissue compression, or positioning adjacent the perianal tissue sufficiently close such that during a push by the mother, the protrusion of soft perianal tissue will engage the TFD to provide a tactile sensation to the mother. In some instances, the user may position the TFD in the first tactile position to contact the patient 10 only when the patient 10 is experiencing a contraction, as observed by the user or indicated by the electronic monitoring system. Once the TFD is positioned in the desired first tactile position, the method includes the step at 812 of maintaining the TFD in contact against the mother in the first position.

During initialization of the method in step 800, if it is determined that the mother has not previously had a successful vaginal delivery or has previously undergone a Cesarean section child delivery procedure, the method continues to step 810 where a TFD is applied in a first tactile position to provide perianal tactile sensation to the mother. Of course, use of the methods and devices described above can be applied to all patients; however, it may be desirable in some situations to limit use of the labor management devices and techniques to those patients mostly likely to benefit from the added attention and treatment. In some instances, the method omits the steps 800-806 and commences at step 810 with the application of the TFD against the patient 10 during the second stage of labor. As described above, a first tactile position can include applying the TFD in a pressure inducing and tissue compression engagement at a first pressure threshold, engagement with the perianal tissue without pressure inducement or tissue compression, or positioning adjacent, but spaced from, the perianal tissue in a sufficiently close arrangement such that during a push by the mother, the protrusion of soft perianal tissue will engage the TFD to provide a tactile sensation to the mother. Once the TFD is positioned in the desired first tactile position, the method includes the step at 812 of maintaining the TFD to the mother in the first position in any suitable manner, including the techniques disclosed herein of a user grasping the grip 106 and applying pressure through the perianal support member 102 against the patient 10.

After the TFD is positioned, the method of using the TFD to manage a mother's labor continues at step 814 by monitoring the progress of labor. In one instance, the progression of labor can include shortening or thinning of the cervix, the amount of cervical dilation, and/or the amount of movement of the child toward the vaginal opening over a given a period of time. In another instance, the progression of labor can include the amount of movement of the child toward the vaginal opening in comparison to the number of contractions or successful pushes the mother has experienced. In some instances, the TFD may include a counting component to track the number of successful pushing episodes experienced by the device. In some instances, as described above, the TFD may include a haptic feedback component to monitor the pressure applied against the device (e.g., the contact surface) by the patient. As described above, the determination of the progression of labor may be made by a healthcare provider monitoring the patient or by an electronic monitoring system receiving one or more inputs indicative of labor progression such as the number of contractions, effective pushes, and movement of the child within the mother and/or overall time of labor. As long as labor is progressing as desired in step 816, the method continues with monitoring the progress of labor in step 814.

If labor is not progressing as desired in step 816, then the method progresses to modifying the position of the TFD at step 818 to move the TFD to a second tactile position on the mother to thereby increase the tactile sensation and/or to change the degree of haptic feedback for the mother, which may improve her ability to effectively push the baby towards the vaginal opening by supplying a tactile focus point against which to push and/or by providing an external scaffolding or sacral extension member that supports the anococcygeal region tissues (including, for example, the posterior pelvic floor tissues) to guide the baby's head through the birth canal towards the vaginal opening. Similarly, the monitoring of the labor process also takes into account the administration of sensory numbing medications administered to the mother at step 820. As will be appreciated, the application of numbing medications, including spinal epidurals, orally administered pain relievers and intravenously injected pain relievers, may significantly reduce the mother's ability to feel pain along with tactile sensation in the perianal tissues. As a result, the method of managing the labor process advances to step 818 to increase the amount of tactile sensation applied to the perianal tissues. In some instances, the user may coordinate this repositioning of the TBD to apply more tactile sensation and/or to change the degree of haptic feedback against the mother with the mother's contractions. Thus, the user may gradually increase the pressure applied by the TBD in sync with the increase in intrauterine pressure due to contractions. In other instances, the user may decrease the pressure applied by the TBD in sync with the increase in intrauterine pressure due to contractions, particularly if labor is progressing as desired In one aspect, in order to increase tactile sensation at step 818, the TFD is moved to a second tissue engaging position where the amount of pressure applied to the perianal tissue is increased compared to the first tactile position. In an exemplary embodiment, the TFD includes a pressure indication mechanism that provides feedback to the individual moving the device about how pressure is being applied, or if the pressure is increasing from the first position, as the TFD is moved to the second position against the perianal tissues. In another exemplary embodiment, the TFD includes a push evaluation system (e.g., the push evaluation system 615 shown in FIG. 15) that provides feedback to the individual moving the device about the strength, directionality, and/or effectiveness of the mother's pushing effort. In an alternative form, the healthcare provider applies inward (toward the anus) movement of the TFD while receiving feedback from the mother concerning her ability to sense the increased tactile sensation. Once the mother indicates a desired level of tactile sensation, the healthcare provider (or the patient in patient manipulated embodiments) maintains the device in the second position at step 822.

As will be appreciated, the process of monitoring labor in step 814 and increasing the tactile sensation (or managing the labor process to decrease the tactile sensation if the mother experiences excessive pain or is pushing too hard) can be repeated multiple times throughout the labor process to manage a balance between causing pain/injury to the mother and provides the mother with a tactile sensation to push against to generate more effective pushes with increased movement of the child into and through the birth canal. More specifically, at step 830, tissue adjacent the TFD is monitored to avoid applying too high a pressure on the tissue for too long of a time period. Thus, in step 832 if it is determined that the current position of the TFD may cause tissue injury (e.g., to either the mother or the baby), then in step 834 the TFD device can be moved to reduce the pressure on the perianal tissue or increase spacing from the vaginal orifice. In one embodiment, the TFD includes a mechanism for alerting the user to an over pressure situation and this mechanism can provide feedback on the force exerted on the perianal tissue.

In embodiments employing pressure detecting systems, uterine contraction monitors, or push evaluation systems (e.g., in the grip 106) to determine whether a suitable pressure is being applied to the device and/or whether the patient's pushing force is sufficient, the user may visually observe the grip or may be able to identify by tactile feedback when a suitable pressure is applied by and/or to the labor assistance system 100. If more pressure is desired as indicated by the pressure detecting systems, the push evaluation systems, the uterine contraction monitors, and/or observation, then the user may provide additional pressure through the labor assistance system 100. In embodiments having device adjustment elements (e.g., such as a sufficiently long grip 106) that may be manipulated by the patient, the patient may adjust the pressure applied by the system 100 based on self-assessment or feedback from the various monitoring systems or healthcare professionals.

In some instances, the labor assistance systems described herein that are configured to apply an upward pressure in the pelvic regions may be used in combination with a child birth assisting system that is configured to apply downward pressure in the abdominal region. For example, in some instances, a labor assistance system may be positioned against the patient's perianal region in combination with a child birth assisting system positioned around the patient's abdomen (e.g., above the uterus). Both systems may be arranged and configured to work in concert to decrease the duration of the second stage of labor by assisting the patient's efforts to push the baby through the birth canal.

Figure 18:
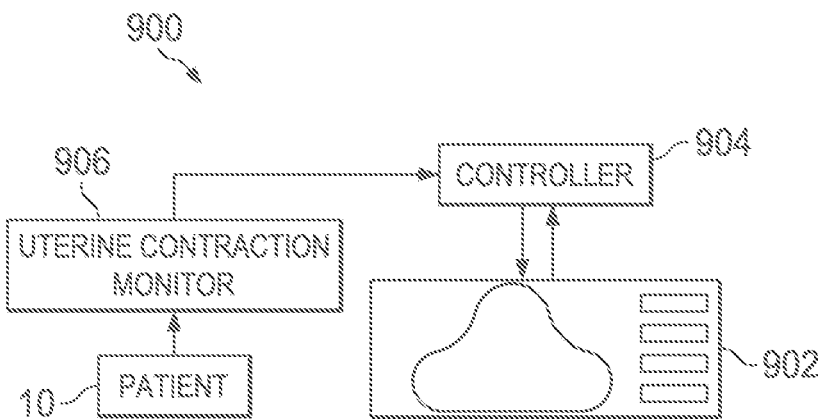
FIG. 18 illustrates an exemplary childbirth assisting system according to one embodiment of the present disclosure.

FIG. 18 illustrates an exemplary childbirth assisting system according to one embodiment of the present disclosure. In the pictured embodiment, the child birth assisting system comprises an expandable pneumatic girdle as described in U.S. Pat. No. 5,871,499, filed Apr. 25, 1997, titled "Child Birth Assisting System," which is incorporated by reference in its entirety. As shown in FIG. 18, a childbirth assisting system 900 includes an automatically synchronized expandable pneumatic girdle 902 configured to externally augment the secondary force of labor (e.g., the forces produced by the increase of intra-abdominal pressure through voluntary contractions of the abdominal muscles and diaphragm, as opposed to the primary force of labor produced by the increase of intrauterine pressure produced by involuntary contractions of the uterus). FIG. 18 is a block diagram of the childbirth assisting system 900 including a patient 10, the abdominal girdle 902, a controller 904, and a uterine contraction monitor 906. FIG. 18 illustrates a closed loop system using patient response and rule-based decision making methods to achieve operator specified responses. The device is a pneumatic closed loop system which is composed of the abdominal girdle 902 and the controller 904. The controller 904 possesses five main functions: (1) Receiving the uterine activity data from the uterine contraction monitor 906 and detecting the onset and offset of contractions; (2) Synchronizing the girdle pressure with the contraction, increasing the girdle pressure at the onset of contraction and decreasing it at the offset of contraction; (3) Adjusting the girdle pressure automatically to obtain the intrauterine pressure at a preset level; (4) Displaying information, including girdle pressure; and (5) Setting an alarm or alert system for abnormal situations. The uterine contraction activity can be monitored either externally (e.g., using an external tocodynamometer) or internally (e.g., using an intrauterine catheter) by the uterine contraction monitor 906. In alternate embodiments, the system may operate on an open loop principle which comprises a modification of functions 2 and 3 listed above. In the open loop system, the application and release of girdle pressure need not rely on intrauterine pressure. Instead, application of pressure to the girdle will be triggered by detection of contraction pressure by the external toco sensor only, and only after a pre-determined threshold pressure is attained and held for a specified period of time.

Figure 19:
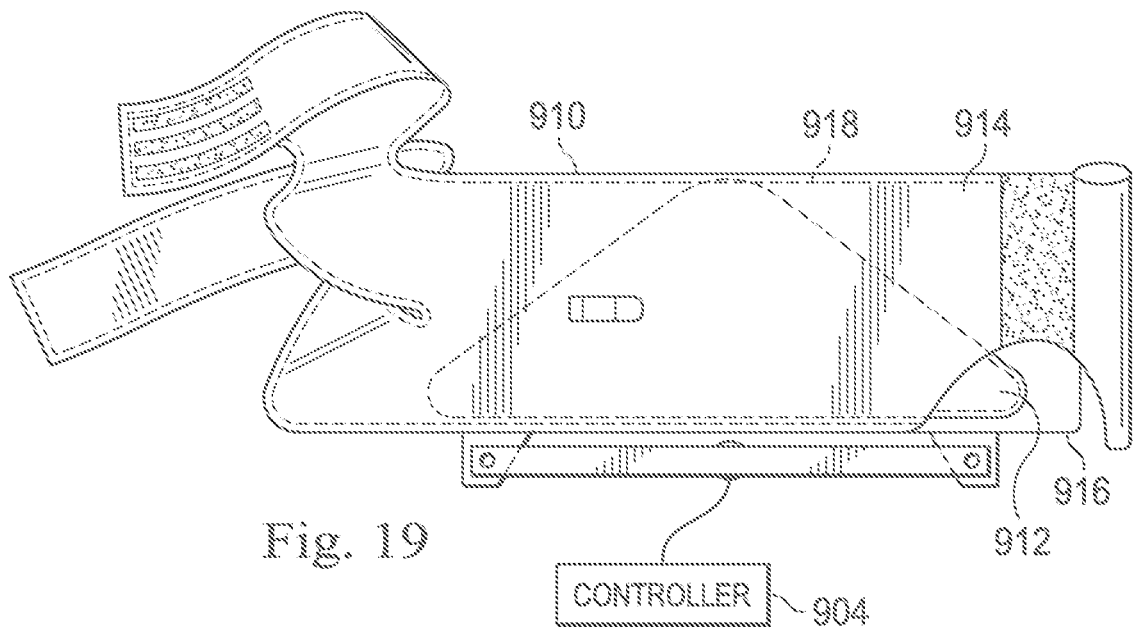
FIG. 19 illustrates an exemplary abdominal girdle according to one embodiment of the present disclosure.

FIG. 19 illustrates the abdominal girdle 902 according to one embodiment of the present disclosure. The girdle 902 is formed of two basic components: the belt 910 and the bladder 912. The design of the belt requires two considerations. The inner lining must be soft and comfortable to the mother while the outer lining must have high tensile strength so that it can be tightly secured around the mother to keep the bladder inflation pressure downward against the abdomen. The belt 910 may be formed from polyvinyl chloride (PVC) or an elastomer-coated fabric, such as polyurethane-coated nylon. For the patient's comfort, the interior lining of the belt which comes in contact with the skin should be a soft fabric, such as the loop material of a hook-and-loop fastener, velour, woven fabric such as cotton or nylon, netting, or a combination of materials including a laminate. The choice of materials will depend on the integration of the bladder. For example, the belt could serve as the reinforced lining to the bladder, or it could be part of the bladder. An elastomer coating on outer layer of the belt may be added to prevent the fabric from stretching, or the outer surface may be non-stretch cotton fabric or surgical tape. In one version illustrated in FIG. 5A, the belt is originally formed in two layers 914 and 916 so that the bladder 912 may be inserted between the layers. (Layer 914 represents the outer PVC layer and layer 916 represents the inner fabric-lined layer.) The layers may be sealed together after the bladder is inserted to firmly retain the bladder at a fixed position within the belt. The sealing welds 918 are indicated as dashed lines. Alternatively, the bladder 912 may be floating, sealed to only one of the two layers of the belt, or unattached to either layer and simply retained between the two layers once they have been sealed together. Selection of belt configuration may be made based upon pressure transfer efficiency, with the floating bladder version having demonstrated improved pressure transfer in prototypes of the invention. The choice of material of which the belt is made will depend upon whether the bladder is attached or floating.

Figure 20:
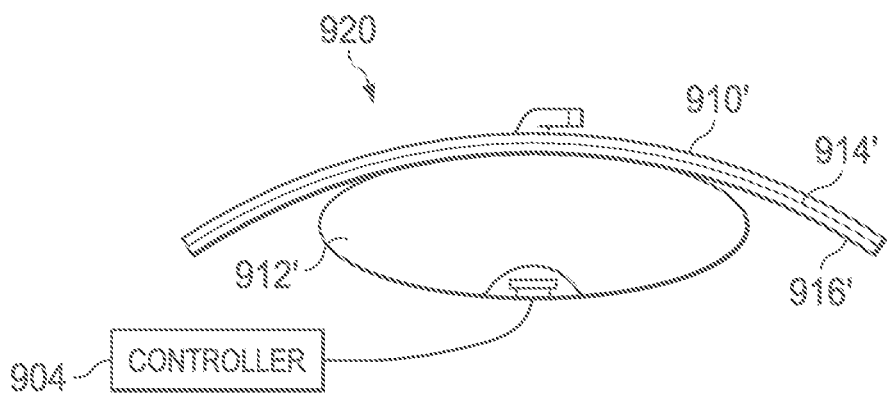
FIG. 20 illustrates an exemplary abdominal girdle according to one embodiment of the present disclosure.

FIG. 20 illustrates another exemplary abdominal girdle 920 in which the inner and outer layers 914' and 916' are sealed together without placing the bladder 912' between the layers. The bladder 912' is held directly against the mother's abdomen, with the inward force of the belt 910' providing means for maintaining the bladder 912' in the proper location.

Figure 21:
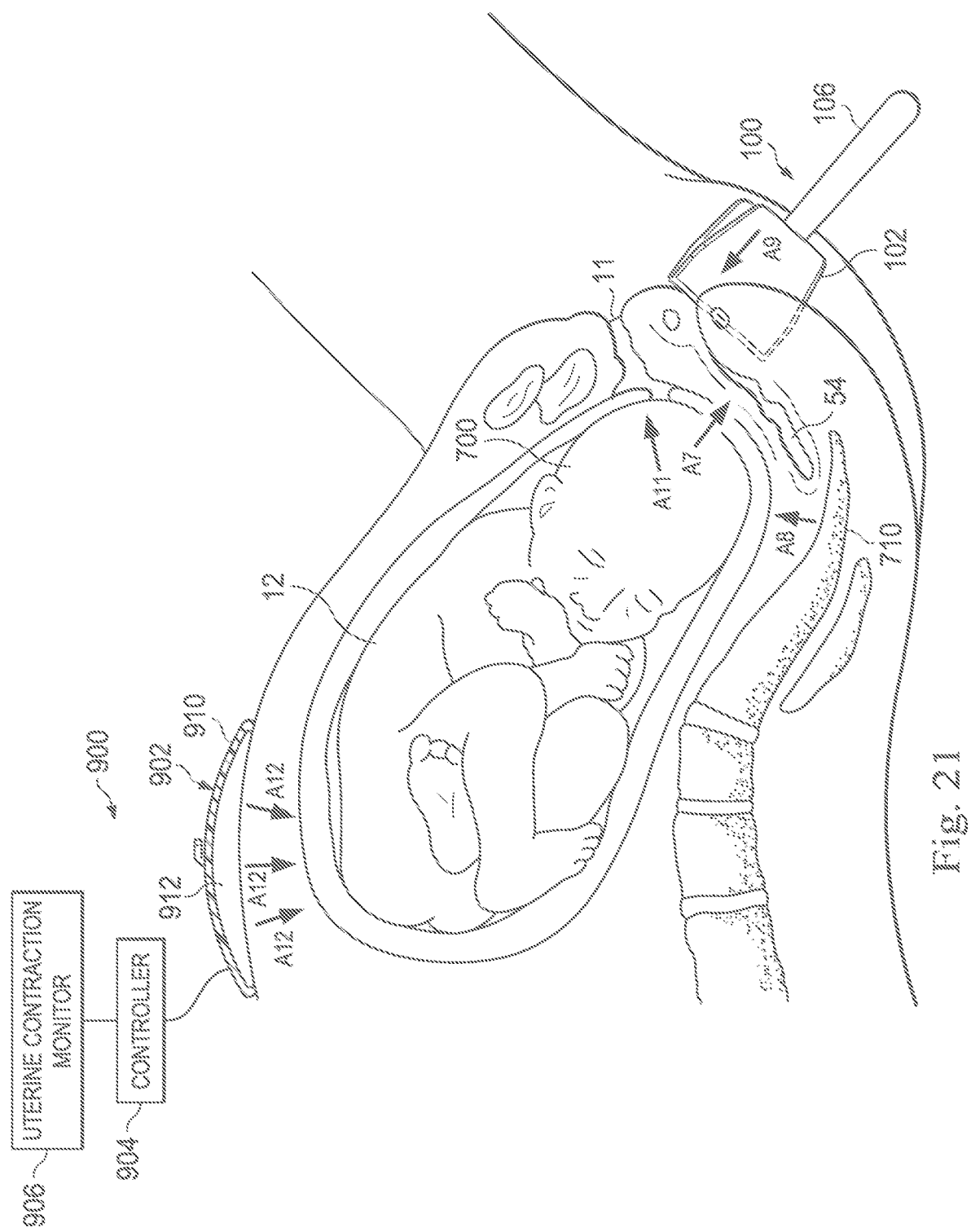
FIG. 21 illustrates a cross-sectional view of a patient in the sagittal plane, an exemplary labor assistance system, and an exemplary childbirth assisting system according to one embodiment of the present disclosure.

FIG. 21 illustrates a cross-sectional view of a patient 10 in the sagittal plane, and includes the childbirth assistance system 900 as well as the labor assistance system 100 positioned on the patient. In the pictured embodiment, the patient's labor is managed using both the childbirth assistance system 900 as well as the labor assistance system 100. For example, in a closed loop system, once the controller 904 detects the onset of contraction, the girdle pressure is increased at the pre-set rate until the desired or preset intrauterine pressure is obtained. Once the intrauterine pressure reaches the preset pressure, the girdle pressure will be maintained to obtain a constant intrauterine pressure. The offset of contraction can be detected when the girdle pressure increases sharply, and the girdle pressure will be released upon detection of the offset of contraction. In some embodiments, the user may apply increased pressure to the perianal tissues through the labor assistance system 100 in the direction of arrow A9 as the girdle pressure increases in the direction of arrows A12, and may decrease the application of pressure to the perianal tissues through the labor assistance system 100 as the girdle pressure decreases. Thus, the childbirth assistance system 900 and the labor assistance system 100 may work in concert to increase the intrauterine pressure and aid the baby's progression through the birth canal. Whereas the childbirth assistance system 900 works from "above" the uterus, increasing external pressure on the abdomen to force uterine contents (e.g., the baby) downward toward the vaginal orifice, the labor assistance system 100 may operate from "below" the uterus by providing the patient with a tactile, pressure-responsive focal point for pushing against and/or providing a sacral extension member. The labor assistance system 100 may also direct the added pressure on the uterus and the baby in the direction of arrow A11 toward the lower pressure area of the vaginal opening 11.

Figure 22B:
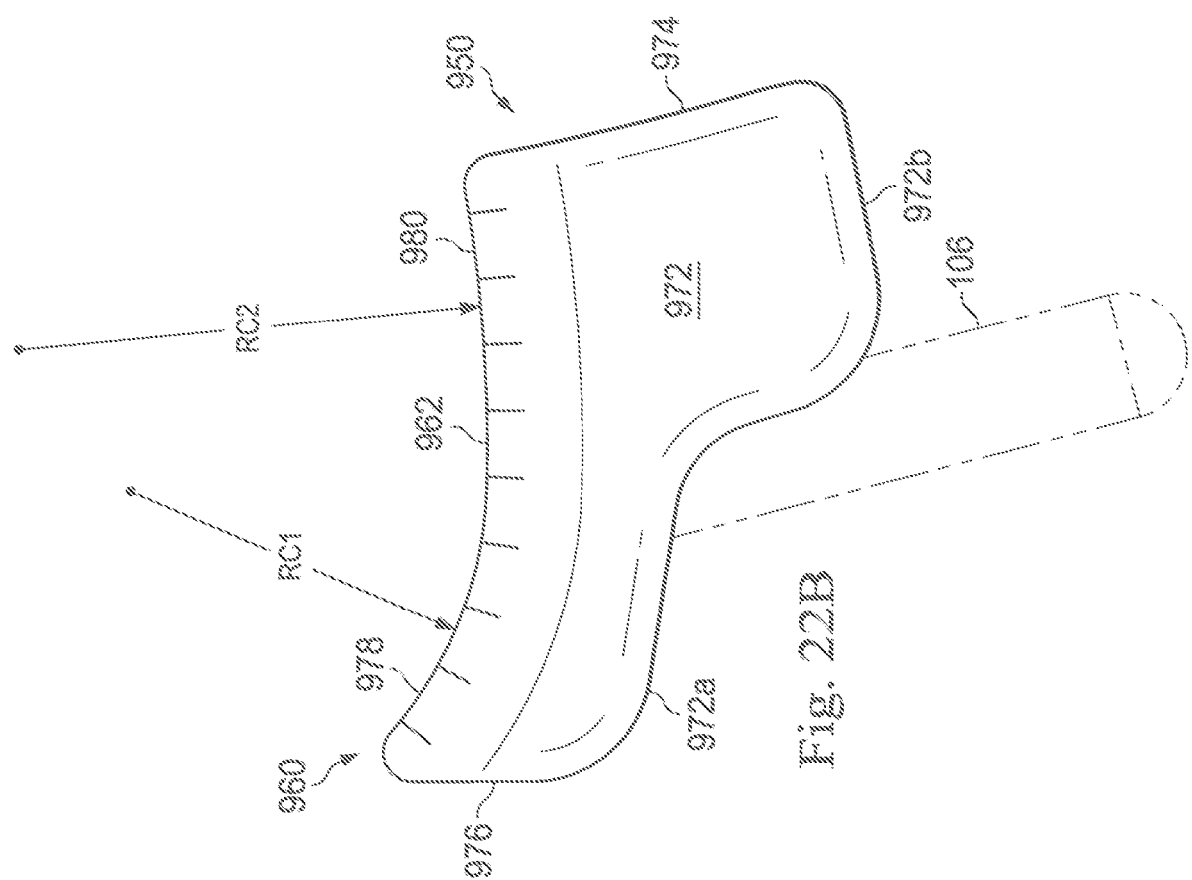
FIG. 22B illustrates a side view of the exemplary labor assistance system shown in shown in FIG. 22A according to one embodiment of the present disclosure.
Figure 22C:
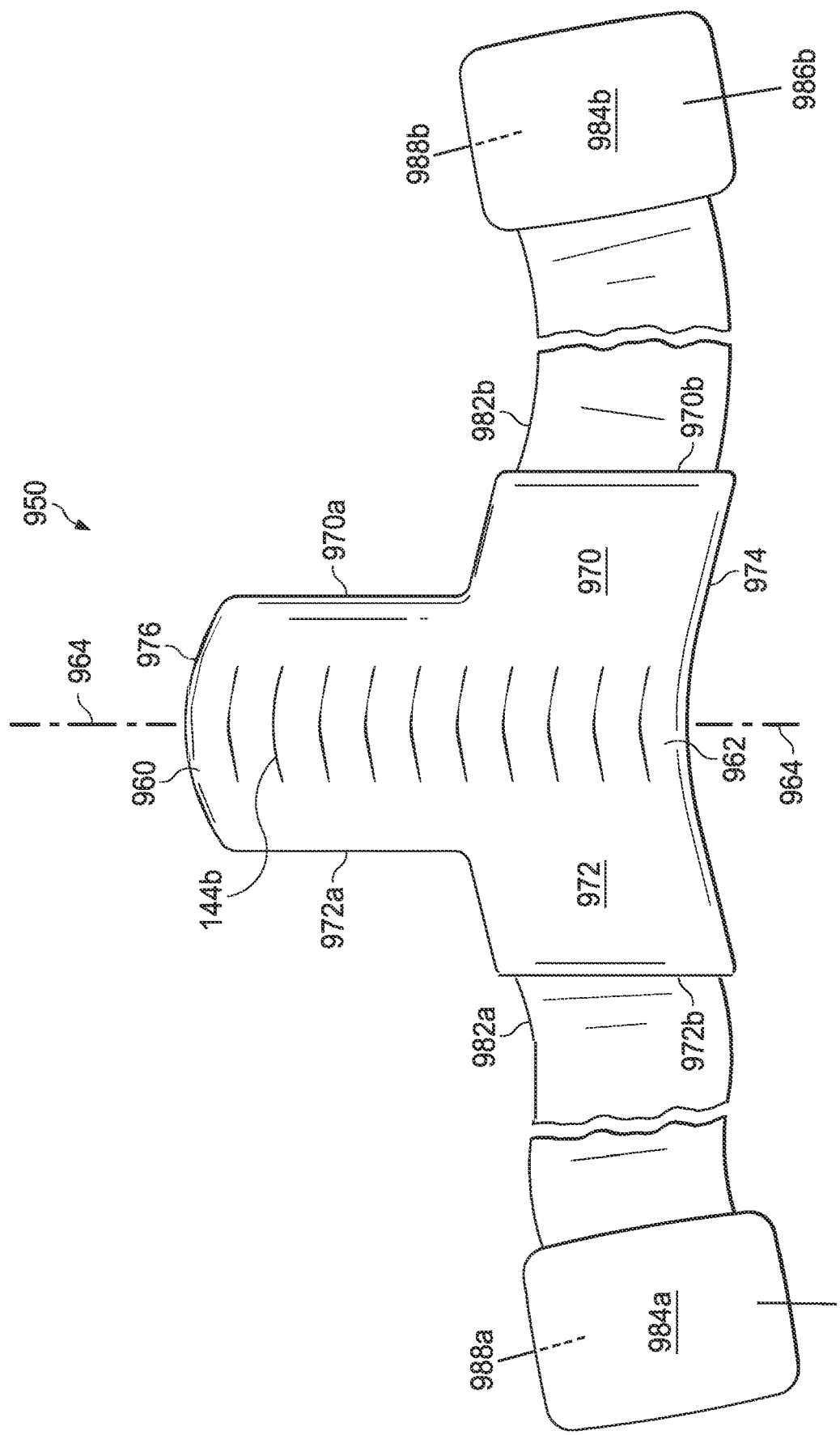
FIG. 22C illustrates a top view of the exemplary labor assistance system shown in FIG. 22B including exemplary securing members according to one embodiment of the present disclosure.
Figure 23:
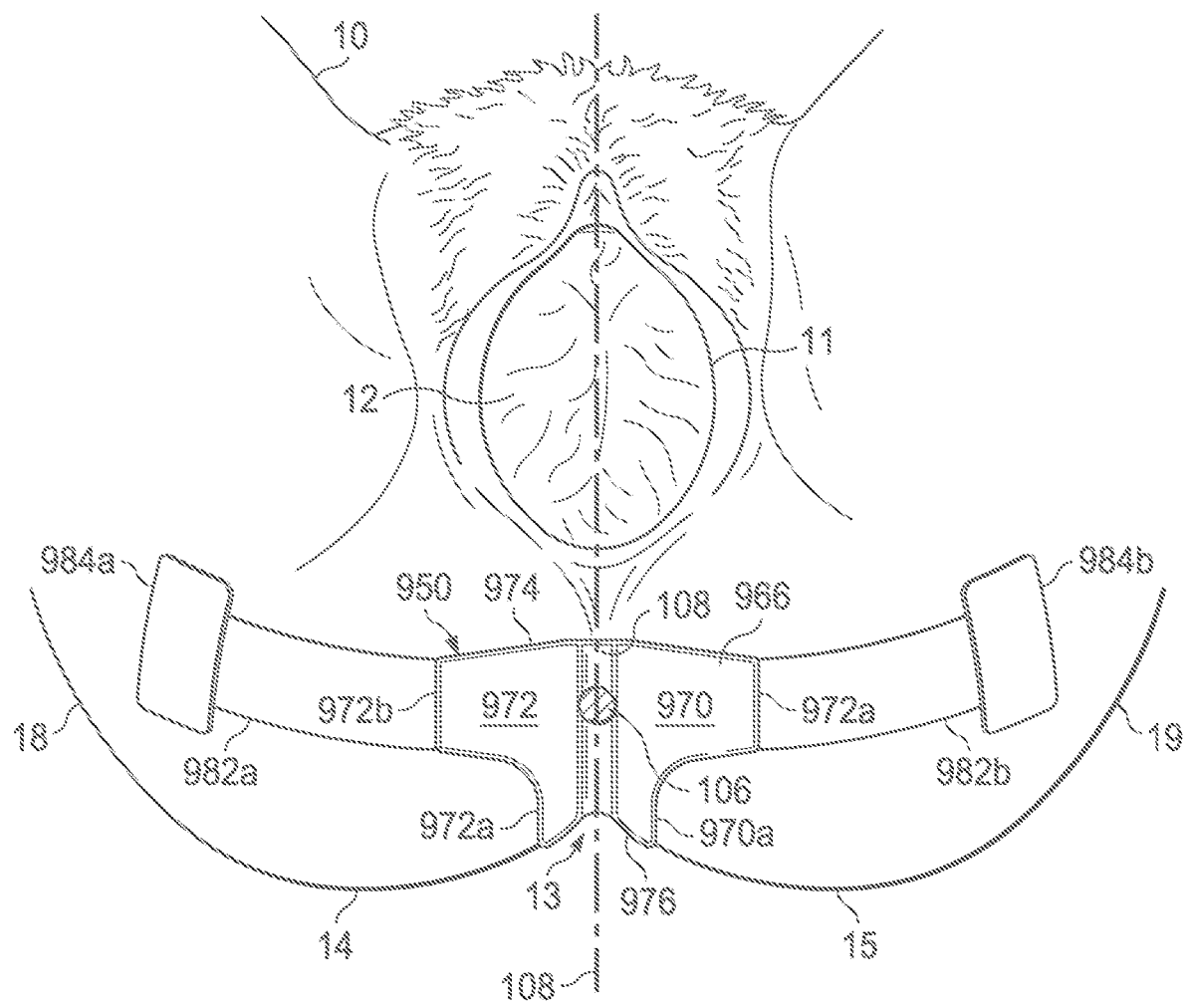
FIG. 23 illustrates a partial perspective bottom view of the labor assistance system shown in FIG. 22A applied to a patient during child delivery.
Figure 24:
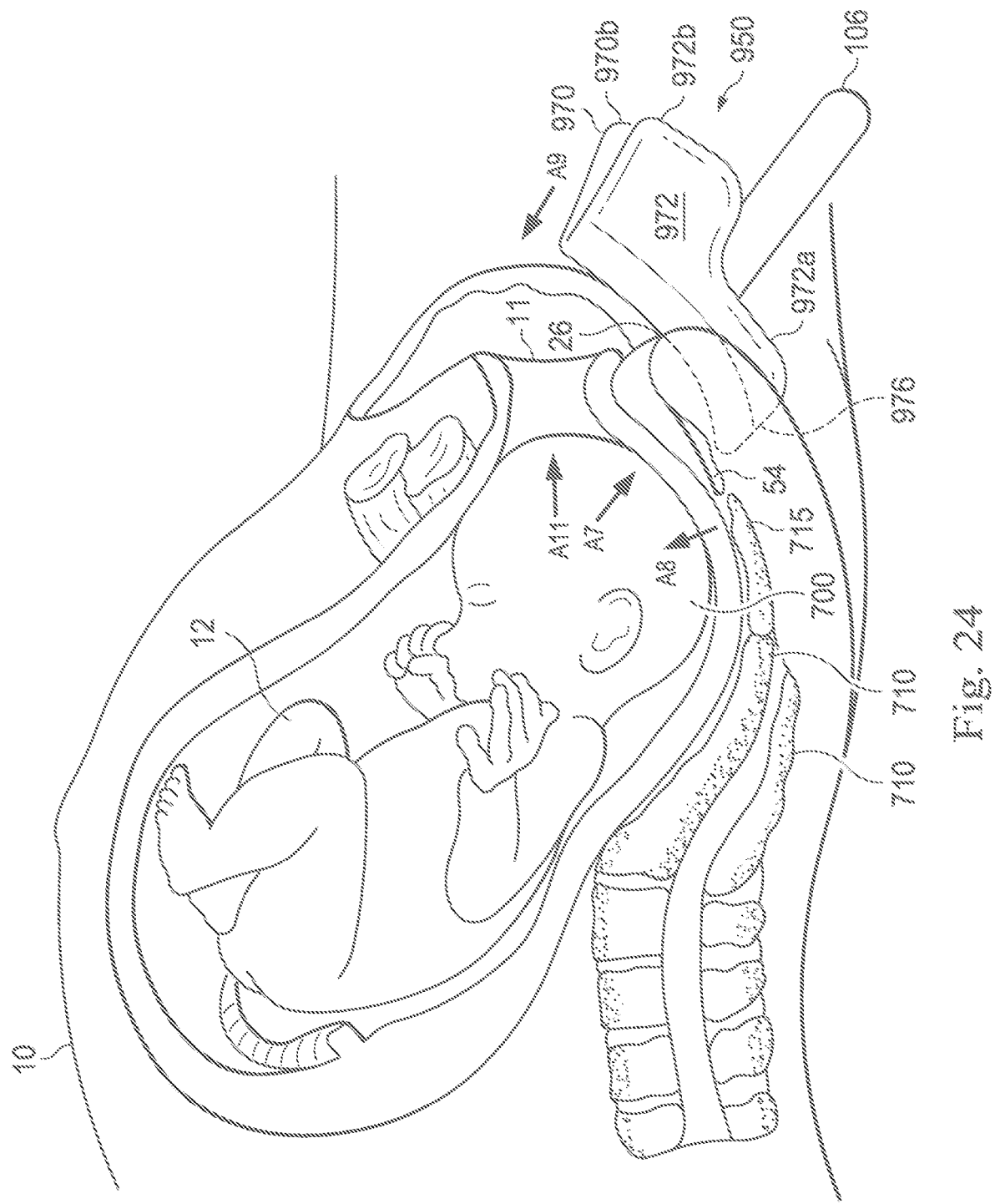
FIG. 24 illustrates a cross-sectional view of a patient in the sagittal plane, and includes the labor assistance system shown in FIG. 22A positioned on a patient.

FIG. 22A illustrates a perspective view of an exemplary labor assistance system 950 including a perianal support member 960 according to one embodiment of the present disclosure. FIG. 22B illustrates a side view of the exemplary labor assistance system shown in shown in FIG. 22A according to one embodiment of the present disclosure. FIG. 22C illustrates a top view of the exemplary labor assistance system shown in FIG. 22B including exemplary securing members according to one embodiment of the present disclosure. FIG. 23 illustrates a partial perspective bottom view of the labor assistance system 950 shown in FIG. 22C applied to a patient 10 during child delivery. FIG. 24 illustrates a cross-sectional view of the patient 10 in the sagittal plane, and includes the labor assistance system 950 positioned on the patient 10.

The perianal support member 960 is substantially similar to the perianal support member 102 except for the differences described herein. For example, the perianal support member 960 includes a contact surface 962 extending along a midline axis 964 from an anterior edge 974 to a posterior edge 976. In the pictured embodiment, the contact surface 962 is slightly curved (e.g., concave) as shown in FIGS. 22A and 22B. As best shown in FIG. 22B, the contact surface 962 of the perianal support member 960 includes areas having different radii of curvature. For example, in the pictured embodiment, a posterior region 978 of the contact surface 962 adjacent the posterior edge 976 has a smaller radius of curvature RC1 than the radius of curvature RC2 of an anterior region 980 adjacent the anterior edge 974. In other embodiments, the contact surface 962 may be substantially straight, as shown with respect to the contact surface 102 shown in FIG. 3). An opposing inner surface 966 defines an access cavity 968. A grip (e.g., the grip 106 discussed above) may be coupled to and extend from the inner surface 966. The perianal support member 960 includes compression elements 970 and 972 that flank the contact surface 192. In some embodiments, the compression elements 970, 972 are integral extensions of the contact surface 962. In other embodiments, the compression elements 970, 972 are coupled to the contact surface 962. The compression elements 970, 972 may extend equal distances from the contact surface 962, as shown in FIG. 22A, or they may extend unequal or different distances from the contact surface 192.

The compression elements 970, 972 meet the contact surface 962 to form a saddle-shaped structure. Each compression element 970, 972 is shaped and configured to include a short portion 970a (shown in FIG. 22C), 972a, and a long portion 970b, 972b. As best shown in FIG. 22C, the long portions 970b, 972b form the anterior edge 974 and the short portions 970a, 972a form the posterior edge 976 of the perianal support member 102. This configuration enables the narrower or shorter portion of the perianal support member 960 (i.e., the shorter portions 972a, 970a, and the contact surface 962 adjacent those portions) to be positioned more easily within the gluteal cleft, as shown in FIGS. 23 and 24.

In some embodiments, the perianal support member 960 is bendable along the axis 964. In the pictured embodiment, the perianal support member 960 includes markings 144b, which are substantially similar to the markings 144 described above in relation to FIGS. 2B and 2C. In some embodiments, the markings 144b comprise cutouts in the contact surface 962 that facilitate the bending of the perianal support member 960. For example, with reference to FIGS. 23 and 24, which illustrate the perianal support member 960 positioned against the patient 10, the contact surface 962 of the perianal support member 960 may be bent into a slightly concave shape upon application of pressure to the contact surface 962 (e.g., through the handle 106).

As described above, FIG. 22C illustrates a top view of the labor assistance system 950 including two securing members 982a, 982b that terminate in anchor pads 984a, 984b. The anchor pads 984a, 984b are shaped and configured to be removably attached to the buttocks 14, 15 (e.g., within the gluteal cleft 13) of the patient 10 (in a similar fashion as shown in FIG. 2C). In some embodiments, the anchor pads 984a, 984b may be adhesively attached to the patient 10. In the pictured example, the securing members 982a, 982b are fixedly coupled to the compression elements 972, 970 and the anchor pads 984a, 984b, respectively. In some examples, the securing members 982a, 982b include a first half of a releasable fastening system coupled to the compression elements 972, 970, such as a hook and loop system or a releasable adhesive system. In the illustrated embodiment, the anchor pads 984a, 984b have a generally rectangular shape that is shorter in length and wider than elongated securing members 982a, 982b. The shape of the anchor pads 984a, 984b is shown for illustration purposes and may take any form that is suitable for fixing to a patient or inanimate object, as well as joining to the elongated fixation member. Each anchor pad 984a, 984b, as shown in FIG. 22C, includes a first side 986a, 986b, respectively, and an opposite second side 988a, 988b, respectively (shown in phantom in FIG. 22C). A portion of each anchor pad 984a, 984b includes at least a portion of the opposite second side 988a, 988b having an adhesive surface (which, in some embodiments, may be substantially similar to the adhesive surface 642 described in more detail with relation to FIG. 15) adapted for joining to the patient's skin or some inanimate object. The opposing first side 986a, 986b (which, in some embodiments, may be substantially similar to the surface 644 described in more detail with relation to FIG. 15) includes the second half of the fastening system, which couples to the securing member 982a, 982b, respectively. In some embodiments, at least a portion of a surface of the anchor pads, whether the first sides 986a, 986b or the opposing second sides 988a, 988b, includes an adhesive coating that can fix the securing member to another object. In one embodiment, the adhesive coating is adapted for releasably adhering to a patient's skin.

Labor assistance systems as described herein may be applied to patients for a variety of reasons including, alone or in combination, any of the following: a) shortening the second stage labor by providing a push focal point to enhance the effectiveness of contractions in advancing the baby down the birth canal, b) reducing the necessity of Cesarean section births by encouraging and monitoring, via pressure feedback, the effectiveness of contractions to generate a pushing effect on the baby to move it toward the vaginal opening as sensed by pressure exerted on the perianal tissue, c) assisting the baby's progression through the vaginal canal by providing an external scaffolding using an anococcygeal support device or sacral extension member, d) covering all or most of the anal orifice and thereby providing defecation control, e) suppressing hemorrhoid development and/or advancement of existing hemorrhoids, f) supporting internal and external tissues to inhibit damage such as anal sphincter damage and lacerations, and g) delivering post-delivery therapeutic treatments, such cooling treatments, for example.

In one embodiment, the labor assistance system 100 (and/or the labor assistance system 950) is formed of biocompatible material suitable for contact with human tissue. Moreover, in one embodiment, the system is provided sterile in a package for single use application on a patient, although reusable devices according to the present teachings are also disclosed in the present description. In the single use type of embodiment, the system is cost effectively manufactured such that it is discarded after use. For example, the system 100 is formed by of a substantially rigid polycarbonate material. In one aspect, the system 100 is injection molded to substantially its final form (e.g., V-shaped form with the grip 106). In some embodiments is contemplated that grip 106 may be riveted, snapped or otherwise fixedly attached to the contact surface 104 and compression elements. Still further, in a different embodiment, the grip 106 is passed through a channel or other opening associated with the compression elements to removably join the grip 106 to the perianal support member 102.

It is contemplated that in other embodiments, the perianal support member 102 and the grip 106 are formed by compression molding, transfer molding, reactive injection molding, extrusion, blow molding, casting, heat-forming, machining, deforming a sheet, bonding, joining or combinations thereof. In other embodiments, suitable materials for the perianal support member 102 and the grip 106 include polymers, metals, ceramics or combinations thereof. The materials can be or include alone or in combination: hard solids, soft solids, tacky solids, viscous fluid, porous material, woven fabric, braided constructions, or non-woven mesh. Examples of polymers include polyethylene, polyester, Nylon, Teflon, polypropylene, polycarbonate, acrylic, PVC, styrene, PEEK, etc. Examples of ceramics include alumina, zirconia, carbon, carbon fibers, graphites, etc. Examples of suitable metals include titanium, stainless steel, cobalt-chrome, etc.

It is contemplated that in some embodiments, the perianal support member 102 and grip 106 can be sterilized by known techniques such as ethylene oxide gas, gas plasma, electron-beam radiation or gamma radiation. Such materials are available from various suppliers such as 3M. In a similar manner, the securing members or anchor pads may be formed of hook and loop fastening systems available from 3M. Adhesive fixation systems may be adhesive a Rayon woven tape on a liner (1538L from 3M). The tape may include liners to prevent premature tape adhesion. In one embodiment, for example, the liners include a cut between the midline end of the anchor pad and the lateral end. During initial placement, the system is pushed against the anus with a firsthand. The opposite hand spreads the buttocks away from the device while the first hand pushes the perianal support member to get further compressive penetration in the gluteal cleft. The hands are switched and the steps are repeated on the opposite buttocks. After positioning the system, the liners adjacent the anchor pads are sequentially removed and adhered to the medial portion of the buttocks for provisional positioning of the device. Once the device is provisionally positioned, the first lateral liner is removed and with pressure applied to the device, the lateral tape segment is adhered to the patient in a final supporting position to supply compressive force to the device. This step is repeated on the opposite side for final fixation.

The present invention also contemplates a kit that includes one or more of the components described above provided in a package. In one embodiment, the kit includes at least a sterilized labor assistance system. In another aspect, the kit includes a push evaluation system (including securing members and anchor pads) as described above. In still another aspect, the kit includes a childbirth assisting system as described above. In yet another aspect, the kit includes removable grip. In some embodiments, the push evaluation system may be preassembled with the labor assistance system as shown in FIG. 15 or may be provided unassembled. In the unassembled kit, a health care provider can remove the perianal support member, grip, and push evaluation system from the packaging and assemble the labor assistance system with or without connection to the childbirth assisting system. In still a further embodiment, the kit includes a treating compound to apply to the patient. In one such embodiment, the treating compound is provided in a separate package. In an alternative embodiment, the treating compound is applied to or incorporated into the labor assistance system on the contact surface of the perianal support member.

In addition to perianal support during labor, devices and methods disclosed herein provide support to the pelvic floor during an intrapartum period, for example during stage II labor. The pelvic floor, sometimes referred to as the pelvic diaphragm, includes the inferior border of the pelvic cavity defined between the lower opening of the pelvic girdle. The pelvic floor has two openings: the anterior urogenital opening through which the urethra and vagina pass and the posterior rectal opening through which the anal canal passes. The pelvic floor, the sacrum, and the coccyx cooperate to facilitate birth by resisting the downward descent of the presenting part of the baby, and thereby helps the baby to rotate forward to navigate through the pelvic girdle and exit the vaginal opening.

According to embodiments of the present disclosure, an intrapartum pelvic floor support device provides support to one or more muscles of the pelvic floor to assist in preventing birth-related traumas to the pelvic floor, such as pelvic floor incompetence or dysfunction (over-stretching of pelvic floor muscles, ligaments and tendons), organ prolapse resulting from the over stretching, and incontinence secondary to pressure and stretching exerted on the bladder and bladder neck. In one aspect, the intrapartum pelvic floor support device or anococcygeal support device is provided to apply pressure to the skin extending from the perianal region to the coccyx that overlies the pelvic floor to thereby push against and support the internal pelvic floor tissues. Support of the anococcygeal region may increase or lengthen the scaffolding provided by the anatomical pelvic tissues (including, for example, the pelvic floor musculature, the sacrum, and the coccyx) by lengthening or increasing the area of counter-pressure applied to the presenting part of the baby as it descends in the direction of the posterior rectal hiatus, thereby encouraging the baby to turn in the direction of the anterior urogenital hiatus (i.e., the vaginal opening). Support of the posterior pelvic floor by the devices disclosed herein may also assist in reducing injury to the mother from pelvic floor distension that can result from force applied by the baby during labor.

Figure 25:
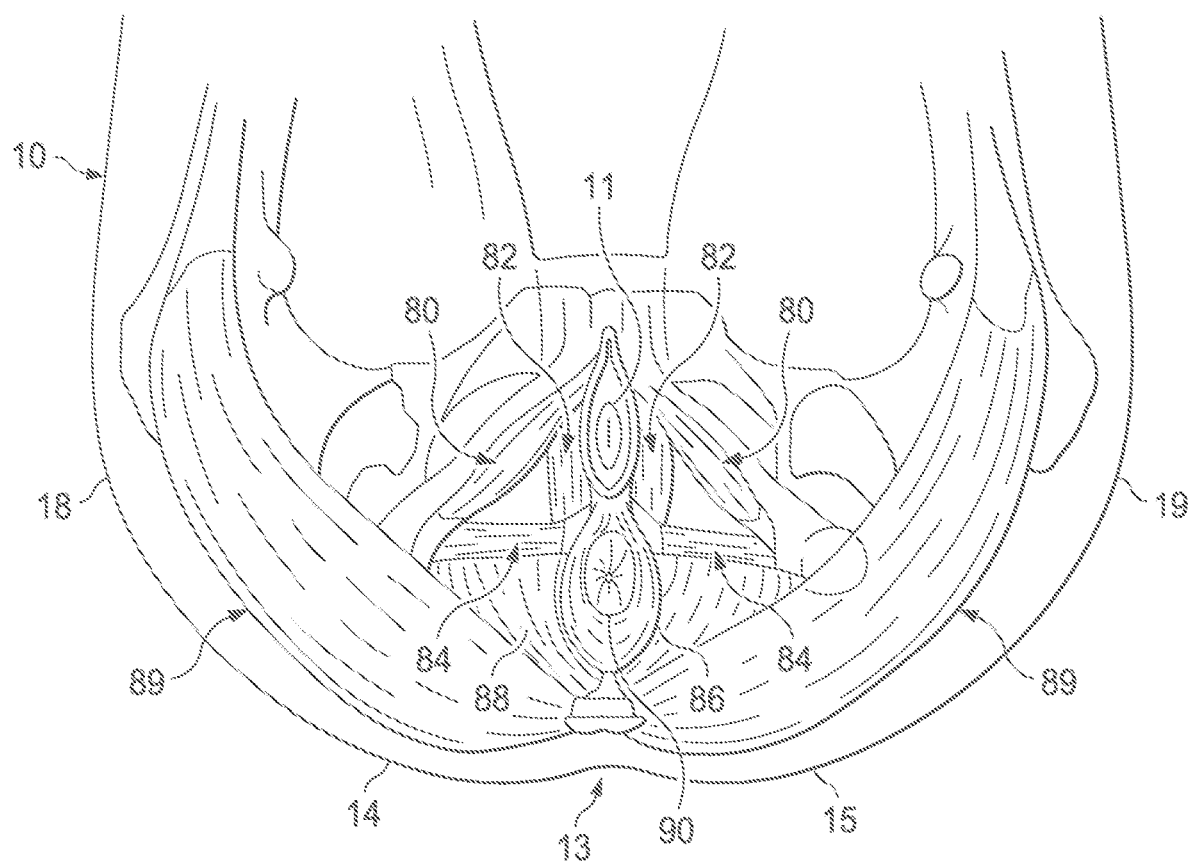
FIG. 25 illustrates is a partial cross sectional bottom view and stylized depiction of a patient anatomy.

FIG. 25 illustrates a partial cross sectional bottom view and stylized depiction of a patient 10's anatomy. In FIG. 25, the patient 10 is shown in partial cross section to illustrate a portion of various muscles of the pelvic floor. Muscles of the pelvic floor include the bulbocavernosus muscles 80, the ischiocavernosus muscles 82 near the vaginal opening 11, the transverse perineal muscles 84, the external anal sphincter muscle 86 near the anal orifice 90, and the levator ani muscle 88. As illustrated in FIG. 25, the muscles of the pelvic floor are deeper within the patient 10 than the skin tissues or, in other words, the skin above the pelvic floor is superficial (or superior with respect to the outside of the body) to the muscles of the pelvic floor listed above. In addition, the muscles of the pelvic floor are superficial (or superior with respect to the outside of the body) to the pelvic bones. Also illustrated in FIG. 25 are the gluteus maximus muscles 89.

Figure 26A:
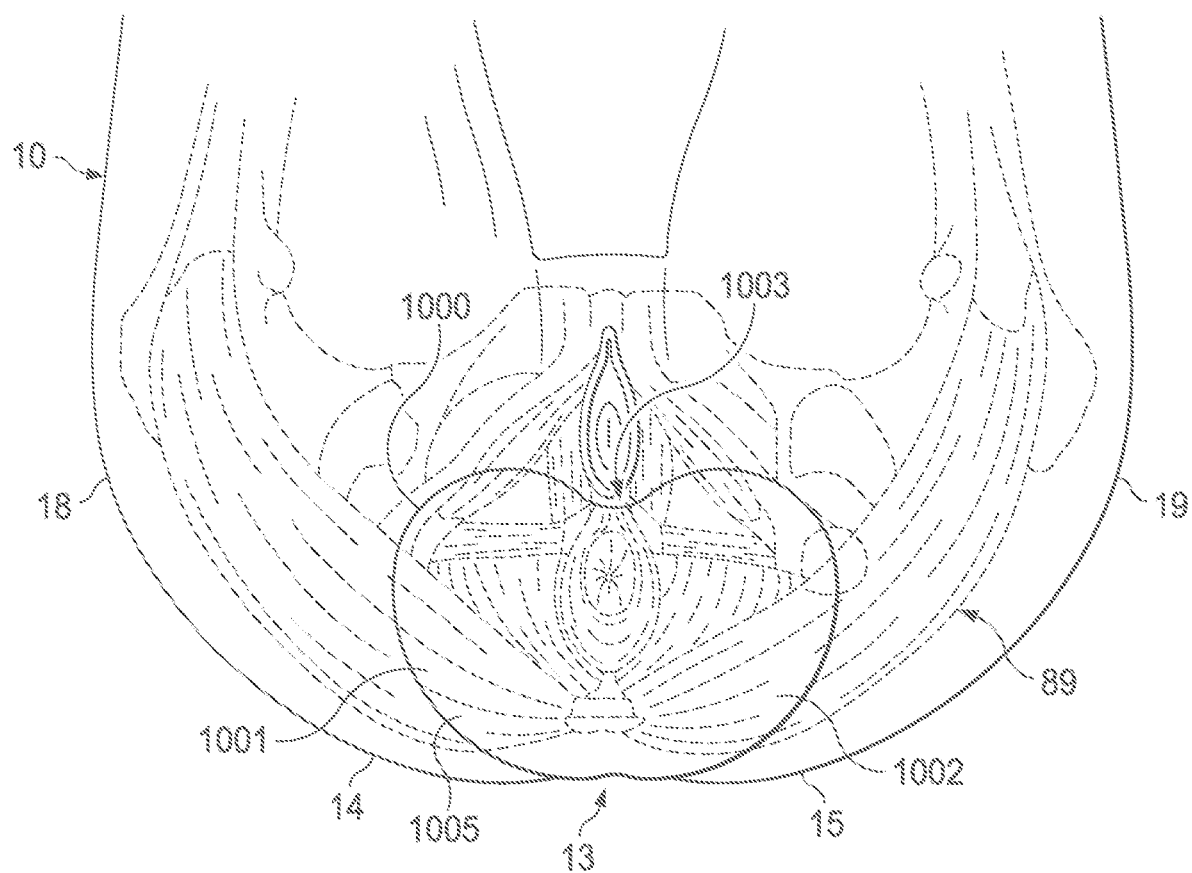
FIG. 26A illustrates a bottom view of an exemplary intrapartum anococcygeal support device positioned on a patient according to one embodiment of the present disclosure with stylized depiction of a patient anatomy.

FIGS. 26A-31A illustrate an intrapartum pelvic floor support device or anococcygeal support device 1000 positioned on a patient 10 according to various embodiments of the present disclosure. FIG. 26A illustrates a bottom view of the exemplary intrapartum anococcygeal support device patient shown in FIG. 26A according to one embodiment of the present disclosure. FIG. 26B illustrates a top view of the exemplary intrapartum anococcygeal support device patient shown in FIG. 22A according to one embodiment of the present disclosure. FIG. 26C illustrates a perspective view of the exemplary intrapartum anococcygeal support device patient shown in FIG. 22A according to one embodiment of the present disclosure. FIG. 26D illustrates a side view of the exemplary intrapartum anococcygeal support device patient shown in FIG. 22A according to one embodiment of the present disclosure. In some instances, the anococcygeal support device 1000 provides a physical or tactile sensation against the patient's skin that acts as a focal point against which the patient can direct her pushing effort during labor. In some instances, the anococcygeal support device 1000 may, for example by covering the anal orifice 70, increase the patient's willingness to push. In some instances, the anococcygeal support device 1000 supports the pelvic floor tissues and acts in concert with the pelvic floor tissues to turn the baby in the correct direction toward the vaginal orifice 11.

As illustrated in FIG. 26A, the anococcygeal support device 1000 may be positioned over one or more muscles of the pelvic floor, for example at least a portion of bulbocaervnosus muscles 80, at least a portion of the ischiocavernosus muscles 82, at least a portion of the transverse perineal muscles 84, at least a portion of the external anal sphincter muscle 86, and at least a portion of the levator ani muscles 88 during labor. As illustrated, the anococcygeal support device 1000 extends over substantially all of the levator ani muscles 88, the transverse perineal muscles 84, and the external anal sphincter 86.

In the embodiment shown in FIGS. 26A-26D, the anococcygeal support device 1000 includes first and second compression elements 1001 and 1002 that extend laterally away from a central compression element 1003. As shown best in FIGS. 26B and 26C, the central compression element 1003 extends longitudinally along the center of the anococcygeal support device 1000 from an anterior portion to a posterior portion. In some embodiments, the anococcygeal support device 1000 is relatively flexible to conform to the contours of the patient's anatomy while retaining the rigidity necessary to apply force to the anococcygeal and/or perianal region.

In one embodiment, as shown best in FIG. 26C, the anococcygeal support device 1000 may be contoured in multiple directions to at least partially anatomically conform to the patient 10. For example, the central compression element 1003 may be formed to fit in the gluteal cleft 13. The first compression element 1001 has an inner surface 1004 and an outer surface 1005. The inner surface 1004 of the anococcygeal support device 1000 is the surface that faces and comes into contact with skin of the buttocks 14 of the patient 10 (and, in embodiments, has an adhesive 1006 to adhere to the skin, as shown in FIG. 26C). The inner surface 1004 is partially concave so that it may receive the buttock 14 in a manner that is anatomically conforming, as illustrated in FIG. 27. In the pictured embodiment, the anococcygeal support device 1000 includes ribs 1003a that extend from the inner surface 1004 toward the central compression element 1003. The spines 1003a may be shaped as any of a variety of structures that are configured to provide structural support to the central compression element 1003. The ribs 1003a convey a force from the inner surface 1004 to the central compression element 1003. The adhesive coating 1006 As best shown in FIG. 26C, the outer surface 1005 is the surface that faces away from the patient 10 and is convex so that the outer surface 1005 follows the profile established by the concavity of the inner surface. In similar manner, the second compression element 1002 has inner and outer surfaces that conform to a curvature of the buttock 15 toward its crown, such as is illustrated in FIG. 27. In some embodiments, as shown in FIG. 26C, at least a portion of the inner surface 1004 includes an adhesive coating 1006 that can fix the compression element 1001 to another object. In one embodiment, the adhesive coating 1006 is adapted for releasably adhering to a patient's skin. In the pictured embodiment, the adhesive coating 1006 is covered by a removable tape 1007 that acts to preserve the tackiness of the adhesive coating 1006 prior to the user removing the tape 1007 and affixing the anococcygeal support device 1000 to another object, including, for example, the skin of the patient. In some embodiments, the adhesive coating 1006 overlies a pad-like structure that may be similar to the anchor pads described above with relation to FIGS. 2B and 2C, for example, The ribs 1003a convey a force from portion of the inners surface adjacent the adhesive coating 1006 to the central compression element 1003.

FIG. 27 illustrates a perspective view of the intrapartum anococcygeal support device 1000 positioned on the patient 10. The side view in FIG. 27 looks from the posterior of the patient 10 towards the anterior of the patient 10 that is not visible in FIG. 27. As can be seen in FIG. 27, the first and second compression elements 1001, 1002 of the intrapartum anococcygeal support device 1000 include concave inner surfaces (e.g., inner surface 1004) that follow the contour of the buttocks 14, 15. This results in the central compression element 1003 extending into the gluteal cleft 13.

Figure 28:
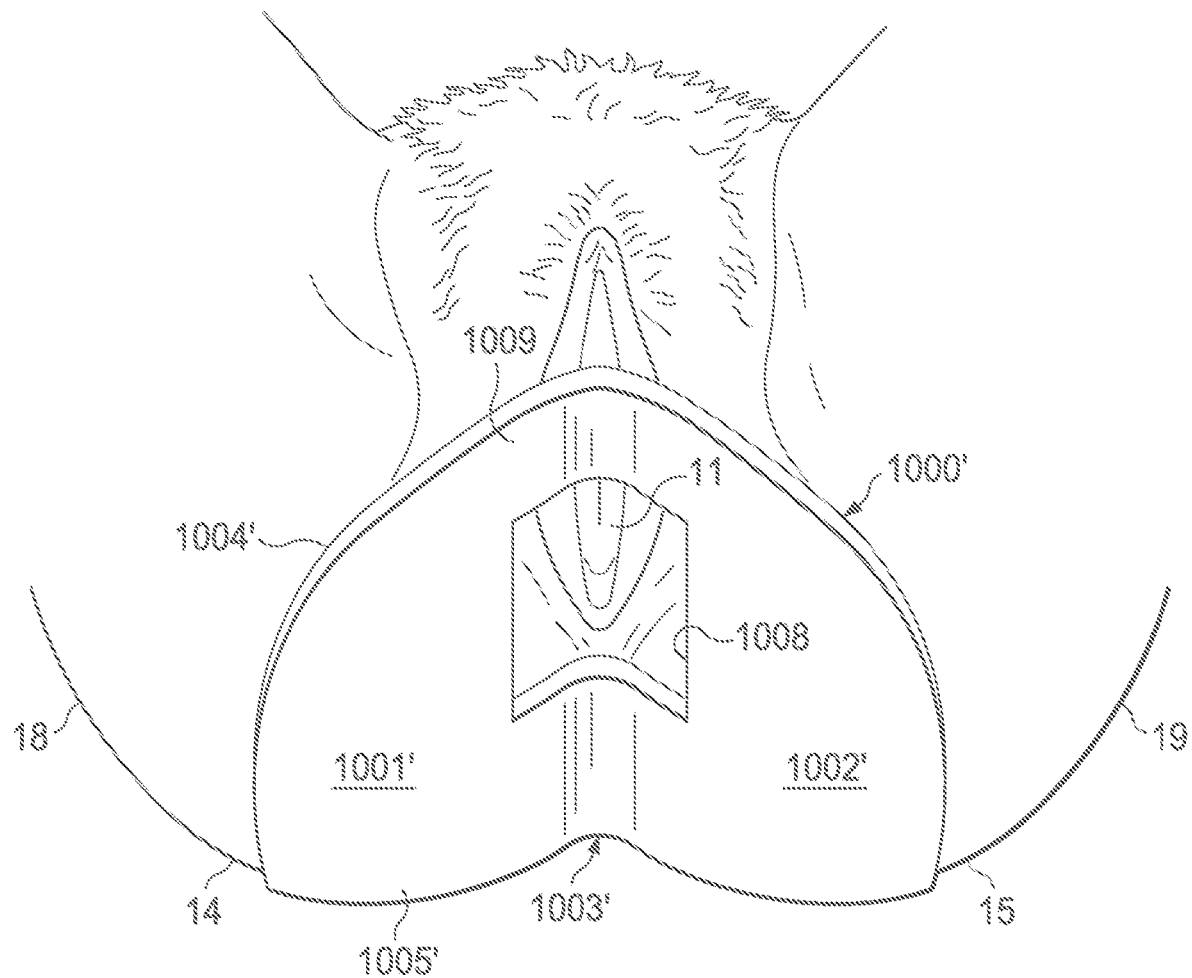
FIG. 28 illustrates a perspective view of an exemplary intrapartum anococcygeal support device positioned on a patient according to one embodiment of the present disclosure.

In addition to the contour, the relative rigidity of the intrapartum anococcygeal support device 1000 may vary along different portions of the device. For example, the intrapartum anococcygeal support device 1000 may have increased rigidity in the area of the central compression element 1003, e.g. focused at an area at and/or near the anal sphincter 86 with flexibility increasing closer to the perineum of the patient 10 and as the first and second compression elements 1001, 1002 extend laterally away from the central compression element 1003. In one example, such as shown in FIG. 28, the variation in rigidity is accomplished by thinning the material as it extends from the central compression element 1003 such that the center material is thicker than the lateral material found at the edges of the first and second compression elements 1001, 1002. Further, the configuration of the central compression element 1003 may be designed so as to provide different levels of pressure to the tissue it comes in contact with. In one example, the central compression element 1003 may have a ridge that fits within the gluteal cleft 13 and approximately uniformly comes into contact with the pelvic floor tissue extending from the intrapartum anococcygeal support device 1000's anterior portion to its posterior portion. The ridge may have a uniform height to apply uniform pressure along the cleft, or alternatively may have an increase or decrease in height in one or more areas to provide more or less pressure, respectively, at those points. In an alternative embodiment, the central compression element 1003 may have two parallel ridges and a small valley therebetween that runs along the length from the anterior to posterior portions of the patient 10, for example similar to that illustrated in FIG. 34B.

There are multiple ways in which the intrapartum anococcygeal support device 1000 may be held in place against the patient 10. According to an embodiment, a pair of extending securing members 2010 and 2020 may be attached to top surfaces of the first and second compression elements 1001, 1002 and configured to assist in holding the intrapartum anococcygeal support device 1000 in pressurized engagement with the tissue superficial to the pelvic floor (e.g., the patient 10's skin over the muscles of the pelvic floor) such as in the areas shown in FIGS. 26A-31A.

The securing members may be the first half of a releasable fastening system with adhesive pads 2012 and 2022 attached to the patient, such as a hook and loop system or a releasable adhesive system, similar to the manner described above with relation to FIGS. 2B, 2C, 9B, 15, 22C, 23, and 26B-26D. A securing member 2020 may be attached to the first compression element 1001 at a periphery of the first compression element 1001 and be joined to pad 2022. In a similar manner, the second securing member 2010 may be attached to the second compression element 1002 at a periphery of the second compression element 1002 and be joined to pad 2012. In some embodiment, the securing members may be elongated, flexible strips of a material. The securing members may extend outwardly and laterally away from the central compression element 1003.

The securing members may be part of a releasable fastening system as described above with respect to other embodiments. In an example, the securing members may be attached to respective anchor pads, for example adhered to skin of patient 10 superficial or superior to the gluteus maximus muscles 89. Each anchor pad may have a generally square shape that is shorter and wider than the securing members. The anchor pads may take any form that is suitable for fixing to a patient or inanimate object. The anchor pads may include a first adhesive surface adapted for joining to the patient's skin or some inanimate object. The opposing surface of each anchor pad may include the second half of the releasable fastening system. Instead of using the hook and loop fastener arrangement discussed above, at least a portion of surfaces of the securing members may have an adhesive coating adapted for joining to a fixed object. The securing members may be fixed to an inner surface of the first and second compression elements. At least a portion of a surface of the securing members may include an adhesive coating that can fix the securing member to another object.

In one embodiment, the adhesive coating is adapted for releasably adhering to a patient's skin. In another embodiment, the adhesive is adapted for joining to an inanimate object (e.g., a table or an instrument) or to itself. In this manner, the securing member can fix the position of the intrapartum anococcygeal support device 1000 relative to the operating table or other fixture near the patient 10. In some embodiments, the securing members are formed of flexible tape. Further, while they have been described separately, in one embodiment, the securing members are formed by a continuous piece of material joined at or near the central compression element 1003.

In an alternative embodiment, the securing members may be attached to one or more raised surfaces at the top surfaces of the first and second compression elements 1001, 1002. The raised surfaces may be, for example, raised pegs that elevate the areas to which the securing members are attached. With the areas raised, the securing members may clear the crowns of the buttocks 14, 15 to reach the locations of the anchor pads without interference from the crowns of the buttocks 14, 15.

With the intrapartum anococcygeal support device 1000 secured, it is capable of applying support and pressure to one or more tissues of the pelvic floor during the intrapartum period. As illustrated, the intrapartum anococcygeal support device 1000 may provide this support and/or pressure without interfering with the birthing canal or vaginal opening 11. The contoured inner surfaces of the compression elements 1003, 1001, and 1002 contact the skin overlying the above-identified tissues. In this manner, the intrapartum anococcygeal support device 1000 may non-invasively reduce and/or inhibit pelvic floor trauma. The intrapartum anococcygeal support device 1000 is non-invasive because it is applied to the exterior of the patient 10 and is not implanted into the patient 10. Moreover, the illustrated embodiments are not inserted into any cavity, such as the anal orifice 90 or the vaginal opening 11.

Figure 29:
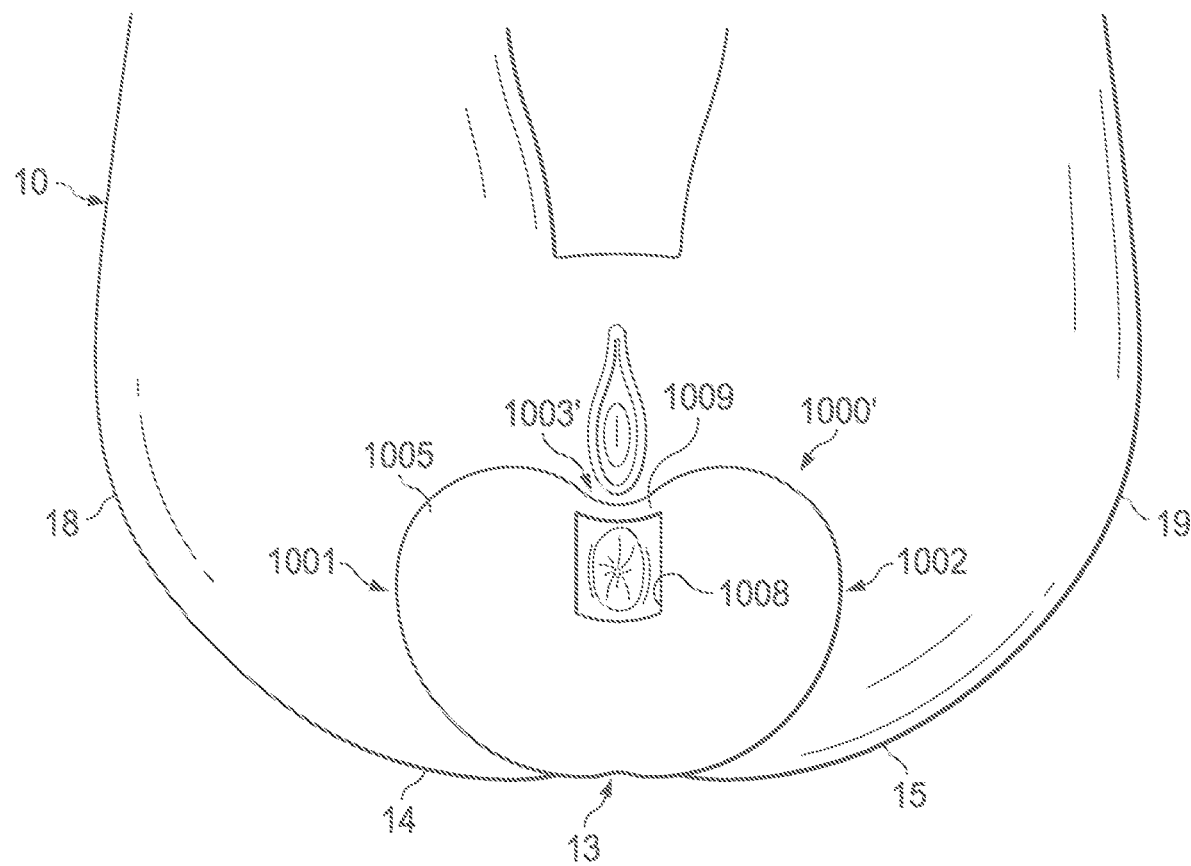
FIG. 29 illustrates a bottom view of the intrapartum anococcygeal support device shown in FIG. 28 positioned on a patient according to one embodiment of the present disclosure.

FIG. 28 illustrates a perspective view of an exemplary intrapartum anococcygeal support device 1000' looking from the anterior portion of the patient 10 towards the posterior portion of the patient 10. FIG. 29 illustrates a bottom view of the intrapartum anococcygeal support device 1000' positioned on the patient 10. For simplicity of discussion, only those aspects of FIGS. 28 and 29 that vary from the discussion above with respect to FIGS. 26A-27 will be addressed. The support device 1000' is substantially similar to the support device 1000 described above with the exception of the differences described below. The central compression element 1003' has an interior surface 1004'. The interior surface 1004' of the central compression element 1003' is partially convex and partially concave (as are the inner surfaces of the first and second compression elements 1001', 1002' to varying degrees) so as to follow the anatomical curvature along the patient 10's midline axis in the sagittal plane as the device 1000' extends from the base of the vaginal opening 11 toward the anal orifice 90 (not shown in FIG. 27), curving upward beyond the anal orifice 90 in the posterior direction, e.g. curving upward toward the patient 10's coccyx (not shown in FIG. 27).

FIGS. 28 and 29 illustrate the intrapartum pelvic floor support device 1000 according to an alternative embodiment. The intrapartum anococcygeal support device 1000' in FIG. 28 further includes a gap 1008 that extends along a portion of the central compression element 1003. As shown, in the pictured embodiment, the gap 1008 is rectangular in shape. Above the gap 1008, an anterior portion 1009 of the intrapartum anococcygeal support device 1000' extends between or bridges between the first and second compression elements 1001', 1002'. The gap 1008 may allow for defecation or other desired access to the perianal region during the intrapartum period. As such, although depicted as rectangular in shape in the embodiment shown in FIG. 28, the gap 1008 may alternatively be of any shape that is sufficient to expose the perianal region while still otherwise generally maintaining pelvic floor support as discussed above.

Figure 31A:
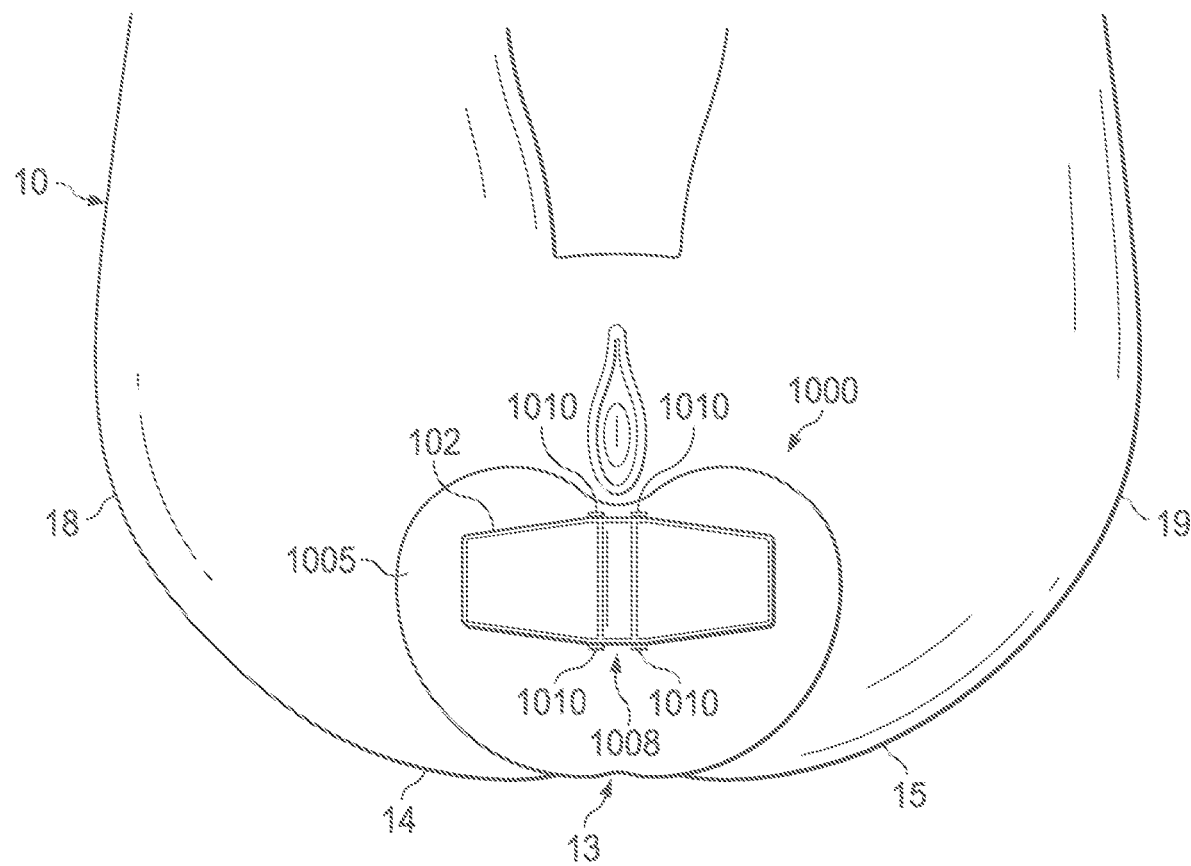
FIG. 31A illustrates an exemplary intrapartum anococcygeal support device and an exemplary perianal support member positioned on a patient according to an embodiment of the present disclosure.

According to embodiments of the present disclosure, the intrapartum anococcygeal support device 1000 may be used in cooperation with other devices, such as the perianal support member 102. The gap 1008 may be sized and shaped specifically so that it may receive the perianal support member 102, for example as illustrated in FIG. 31A. As shown, an external pressure surface or contact surface 104 of the perianal support member 102 fits within the gap 1008, for example with sufficient precision that there is only a small distance between the inside walls of the gap 1008 and the surfaces of the perianal support member 102 so as to avoid pinching of patient tissue. Edges of the inside walls of the gap 1008 may have a radius shape to further avoid pinching. The perianal support member 102 may utilize its own securing members according to one or more of the examples described above. Alternatively, the intrapartum anococcygeal support device 1000 may not include any securing members and instead rely upon the perianal support member 102 utilizing its own securing members to thereby keep the intrapartum anococcygeal support device 1000 in place as well.

Figure 30:
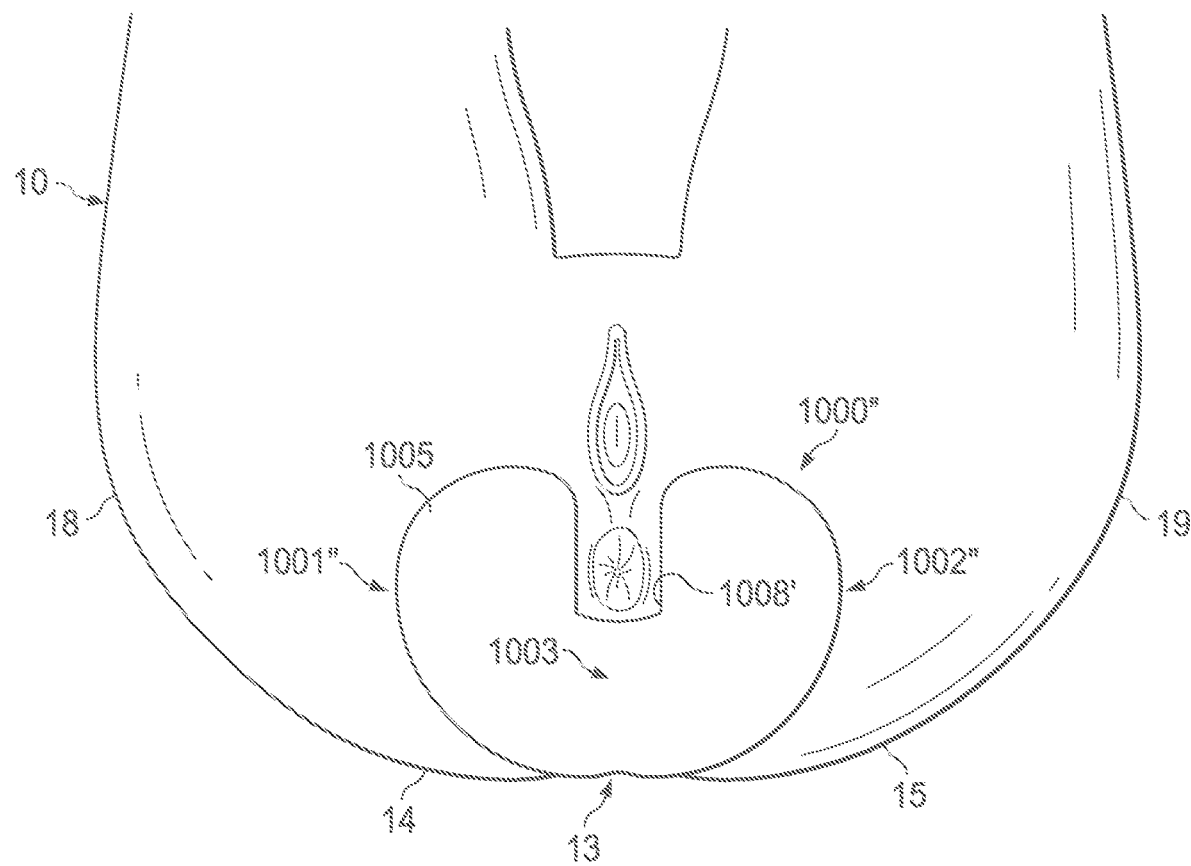
FIG. 30 illustrates a bottom view of an exemplary intrapartum anococcygeal support device positioned on a patient according to one embodiment of the present disclosure.

FIG. 30 illustrates the intrapartum anococcygeal support device 1000 according to an alternative embodiment to that discussed above with respect to FIGS. 28 and 29. In the pictured embodiment, the intrapartum anococcygeal support device 1000" is substantially similar to the anococcygeal support member 1000' described above, except for the following differences. In FIG. 30, instead of a gap 1008, the intrapartum anococcygeal support device 1000" includes a recess 1008'. The recess 1008' interrupts the first and second compression elements 1001", 1002" from connecting each other in an anterior portion of the intrapartum anococcygeal support device 1000 (e.g., near the vaginal opening 11).

In some embodiments, the intrapartum anococcygeal support device 1000 of FIG. 26A may be used alone, without cooperation with a perianal support member 102. In alternative embodiments, the recess 1008 of the intrapartum anococcygeal support device 1000' may be sized and shaped so that it may receive the perianal support member 102, for example so that a posterior end of the perianal support member 102 is adjacent to and in contact with a posterior end of the recess 1008. In an embodiment, the posterior end of the recess 1008' may include one or more locking mechanisms according to one or more of the examples given below with respect to FIG. 28 that couple the intrapartum anococcygeal support device 1000' and the perianal support member 102 together while applied to the patient 10.

In some embodiments, the perianal support member 102 may be held in place with respect to the intrapartum anococcygeal support device 1000 by reliance on one or more securing members alone. Alternatively, as shown in FIG. 31A, the intrapartum anococcygeal support device 1000 may include one or more locking mechanisms 1010 that are designed to lock the perianal support member 102 into place when applied into the gap 1008.

Figure 31B:
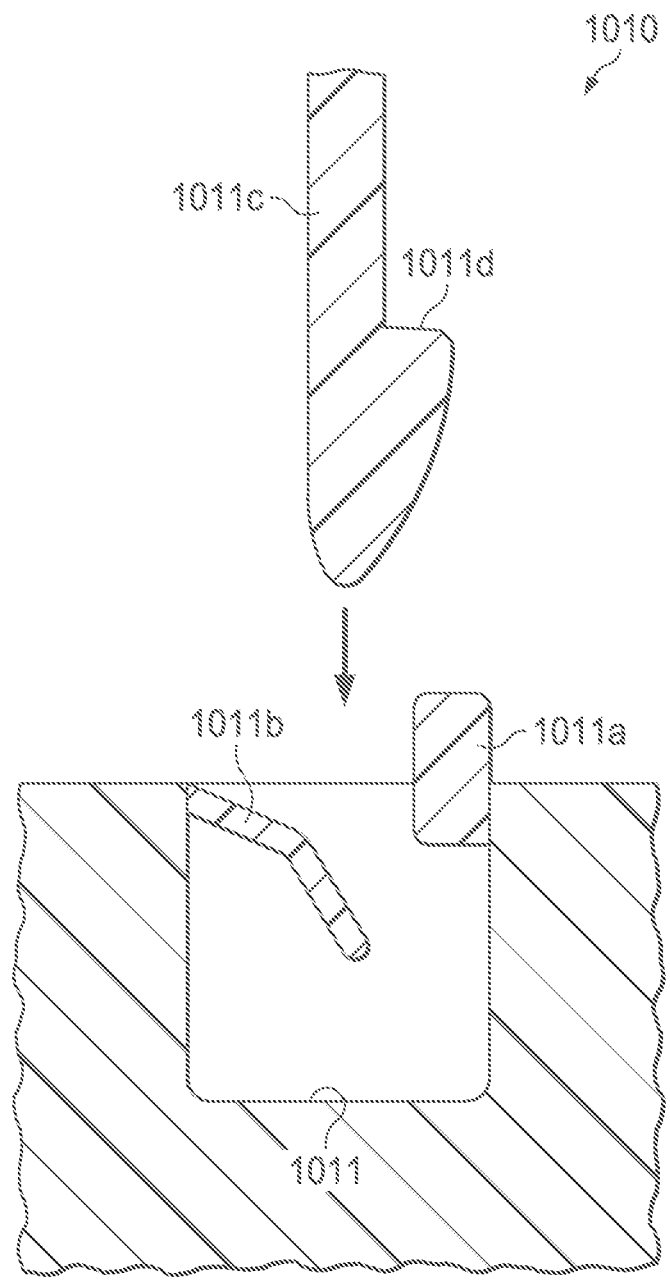
FIG. 31B illustrates an exemplary locking mechanism for an intrapartum anococcygeal support device and a perianal support member according to an embodiment of the present disclosure

FIG. 31B illustrates the exemplary locking mechanism 1010 shown in FIG. 31A in closer detail according to one embodiment of the present disclosure. In FIG. 31B, a female member 1011 may include a blocking member 1011a and a tab 1011b. In an embodiment, the female member 1011 may be integrated or attached with a surface of the intrapartum anococcygeal support device 1000 near the gap 1008. A male member 1011c attached to the perianal support member 102 may include a finger 1011d that, when inserted into the female member 1011, will be caught at the blocking member 1011a to operatively couple the perianal support member 102 and the intrapartum anococcygeal support device 1000 together. As will be recognized, in other embodiments, the female locking member 1011 may alternatively be included with the perianal support member 102 and the male member 1005 with the intrapartum anococcygeal support device 1000. Exemplary locking mechanisms such as that illustrated in FIG. 31B are further discussed in U.S. Pat. Nos. 4,946,404 and 5,577,779, both of which are incorporated by reference herein in their entireties.

In another alternative embodiment, the intrapartum anococcygeal support device 1000 may include a first part of a ratchet locking mechanism and the perianal support member 102 may include a second part of the ratchet locking mechanism. For example, the intrapartum anococcygeal support device 1000 may include a finger that engages teeth in one direction, and the perianal support member 102 a corresponding gear or rack that has teeth to engage the finger. The finger may be spring loaded so that the position of the perianal support member 102 may be shifted to increase or decrease pressure applied by the perianal support member 102 as compared to the intrapartum anococcygeal support device 1000.

Figure 32A:
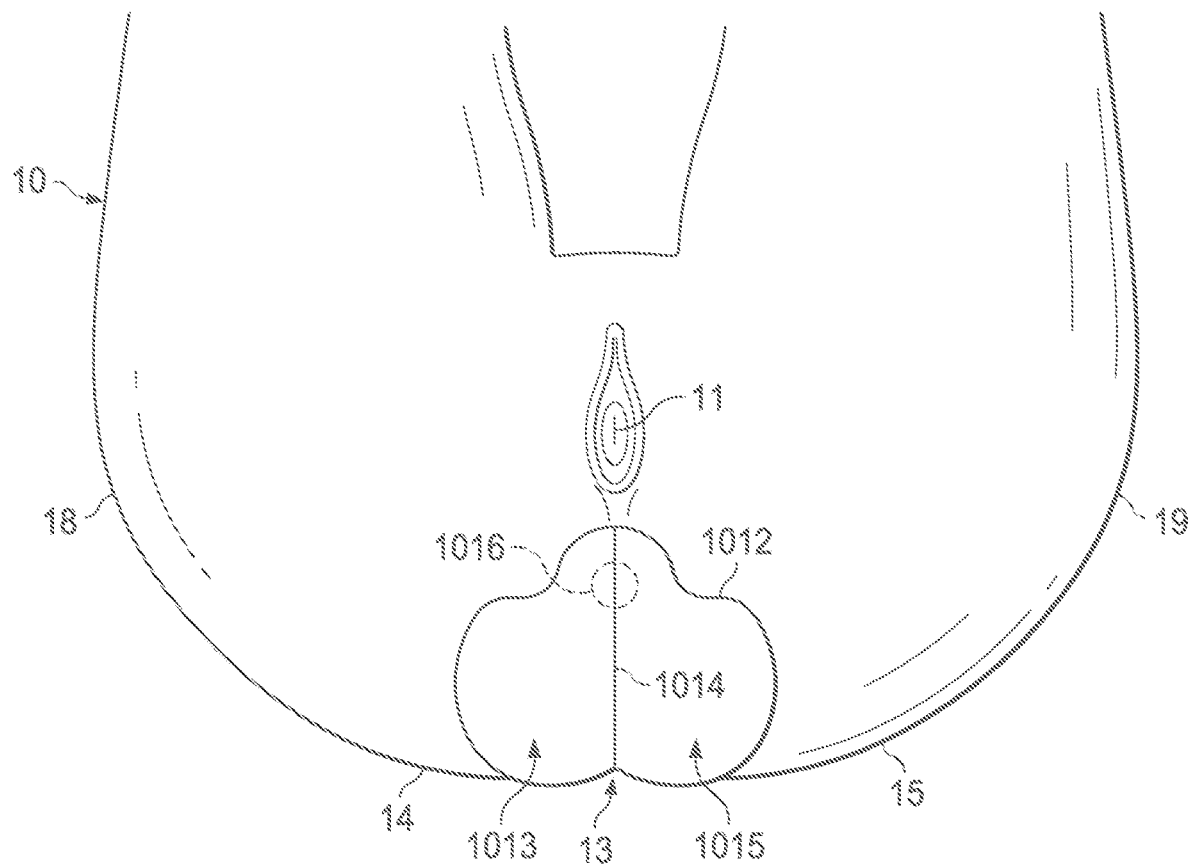
FIG. 32A illustrates an intrapartum pelvic floor support device positioned on a patient according to an embodiment of the present disclosure.

FIG. 32A illustrates an intrapartum pelvic floor or anococcygeal support device 1012 positioned on a patient 10 according to an embodiment of the present disclosure. The intrapartum pelvic floor support device 1012 includes first and second compression elements 1013, 1015 that extend laterally from a midline 1014. The first and second compression elements 1013, 1015 have smaller lateral extensions from the midline 1014 at the anterior portion of the intrapartum pelvic floor support device 1012 than at the posterior portion of the device 1012, which becomes larger towards the posterior of the patient 10. As a result, the intrapartum pelvic floor support device 1012 may engage the tissue superficial or superior to the levator ani muscles 88 of the pelvic floor. This may be beneficial because the levator ani muscles 88 often endure trauma during vaginal childbirth, and the counterpressure applied by the intrapartum pelvic floor support device 1012 during delivery may help to minimize such trauma by, for example, resisting tissue distention and tearing.

Figure 32B:
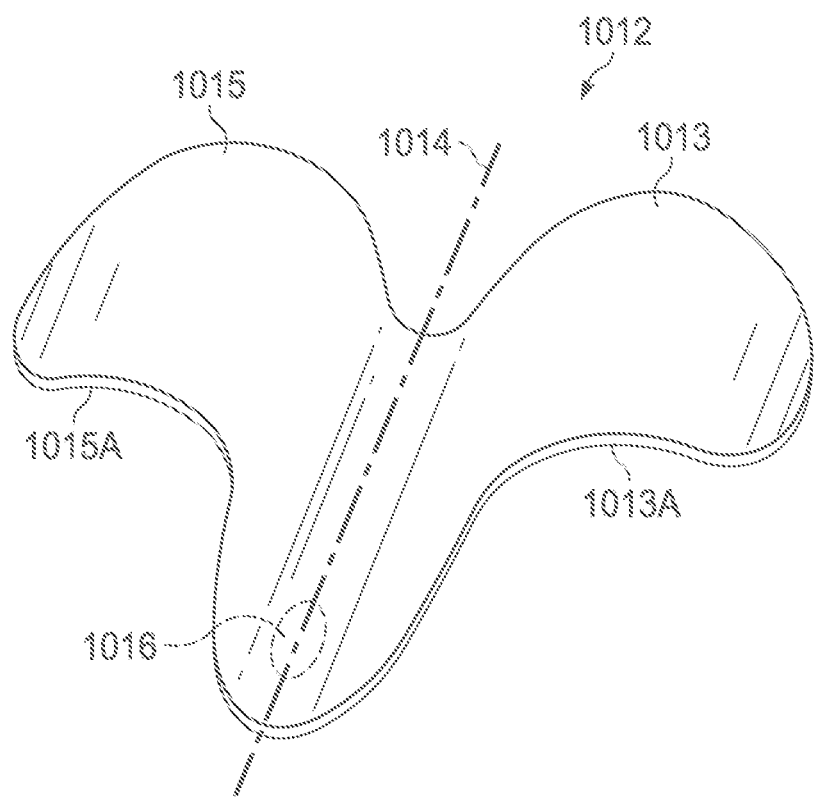
FIG. 32B illustrates a partial perspective top view of an intrapartum pelvic floor support device according to an embodiment of the present disclosure.

In some embodiments, the intrapartum pelvic floor support device 1012 is contoured in lateral and posterior directions from the midline 1014. For example, FIG. 32B illustrates a partial perspective view of the intrapartum pelvic floor support device 1012. As illustrated in FIG. 32B, the first compression element 1013 has a concave inner surface 1013A as the first compression element 1013 extends laterally away from the gluteal cleft 13 that enables a contour of buttock 15 to fit within it. The second compression element 1015 has a concave inner surface 1015A as the second compression element 1015 extends laterally away from the gluteal cleft 13 that enables a contour of buttock 14 to fit within it.

Figure 32C:
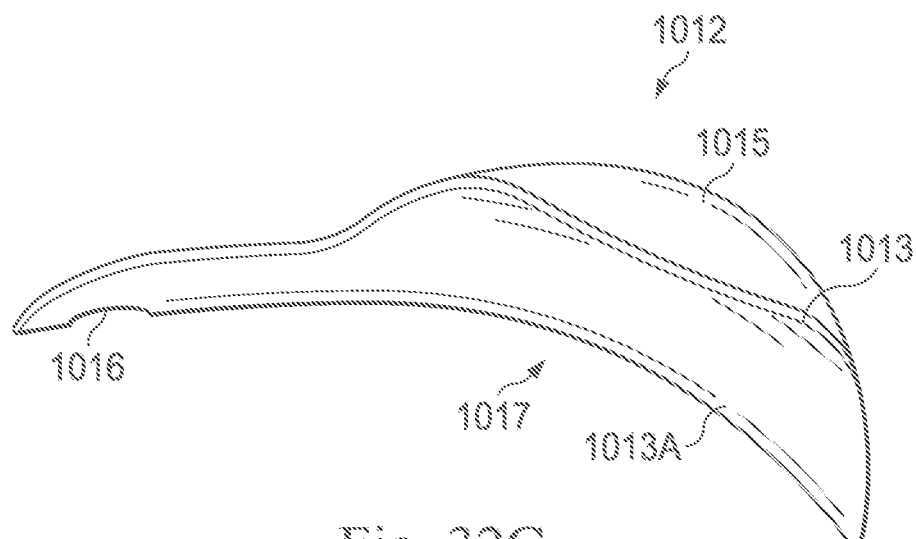
FIG. 32C illustrates a side view of an intrapartum pelvic floor support device according to an embodiment of the present disclosure.

As further illustrated in FIG. 32C, which illustrates a side view of the intrapartum pelvic floor support device 1012, the intrapartum pelvic floor support device 1012 may curve in the posterior direction upward toward the coccyx. This is illustrated by the (concave) curved surface 1017 in FIG. 32C. As illustrated in FIG. 32C, the narrower side (the left side in the pictured embodiment) of the intrapartum pelvic floor support device 1012 is located near the vaginal opening 11 while the wider side (the right side in the pictured embodiment) is located near the coccyx of the patient 10.

In an embodiment, the midline 1014 may be a ridge that fits within the gluteal cleft 13 and approximately uniformly comes into contact with the pelvic floor tissue extending from the intrapartum pelvic floor support device 1012's anterior portion to its posterior portion. This ridge may have a uniform height configured to apply uniform pressure along the cleft. In an alternative embodiment, the midline 1014 may have a void or recess 1016 at or near the anal orifice 90, as shown in FIGS. 32A-32C, in order to prevent or reduce the pressure applied to the perianal tissue at or near the anal orifice 90. As a result, less pressure may be applied to the tissues at the anal orifice 90 than other contact areas of the pelvic floor. In another alternative embodiment, the midline 1014 may be convex at or near the anal orifice 90 in order to provide increased pressure to tissues at or near the anal orifice 90. As a result, greater pressure may be applied to the tissue at the anal orifice 90 than other contact areas of the pelvic floor. In another alternative embodiment, the midline 1014 may have two parallel ridges and a small valley therebetween that runs along the length from the anterior to posterior portions of the patient 10, for example similar to that illustrated in FIG. 34B as discussed in more detail below.

In some embodiments, the intrapartum pelvic floor support device 1012 may be held in place against the patient 10 according to one or more of the embodiments discussed above with respect to the device of FIG. 26A.

Figure 33:
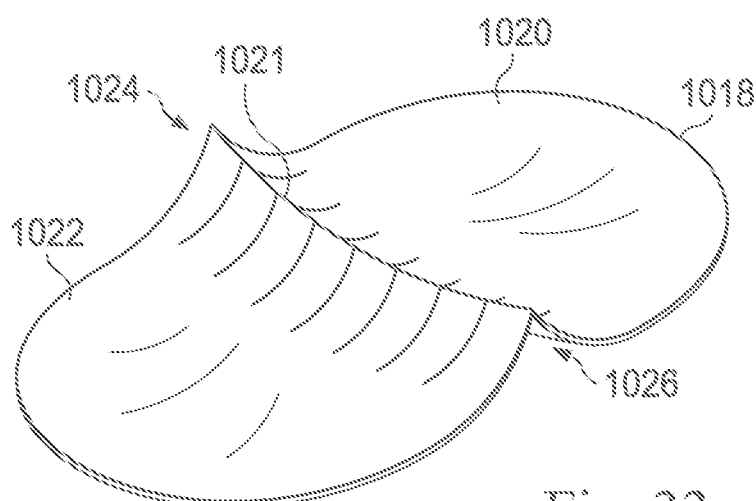
FIG. 33 illustrates an intrapartum pelvic floor support device according to an embodiment of the present disclosure.

FIG. 33 illustrates an intrapartum pelvic floor or anococcygeal support device 1018 according to an embodiment of the present disclosure. The intrapartum pelvic floor support device 1018 includes first and second compression elements 1020 and 1022, as well as a midline 1021. The first compression elements 1020, 1022 may each have a concave inner surface to allow a buttock's contour to fit within it at least partially. As illustrated in FIG. 33, a posterior portion 1024 of the intrapartum pelvic floor support device 1018 is curved upward to follow the contour of the gluteal cleft 13 of a patient 10, and represents the portion of the intrapartum pelvic floor support device 1018 which would be placed at the posterior of the patient 10 toward the coccyx. This curvature may be similar in principle to that discussed above with respect to FIG. 32C and the curved surface 1017. The anterior portion 1026 follows the contour of the gluteal cleft 13 and extends toward the vaginal opening 11. The intrapartum pelvic floor support device 1018 provides pelvic floor support by medially compressing tissue that it comes in contact with.

The intrapartum pelvic floor support device 1018 may be held in place against a patient 10 according to one or more of the embodiments discussed above with respect to the device of FIG. 26A. The intrapartum pelvic floor support device 1018 may be preformed, for example by an injection molding process, according to a pre-defined contour. The pre-defined contour may represent a composite profile of different body types, for example. Alternatively, the intrapartum pelvic floor support device 1018 may have one of multiple pre-defined contours, each of which providing a different contour resulting in more or less pressure at particular areas of the intrapartum pelvic floor support device 1018 than the other contours.

Figure 34A:
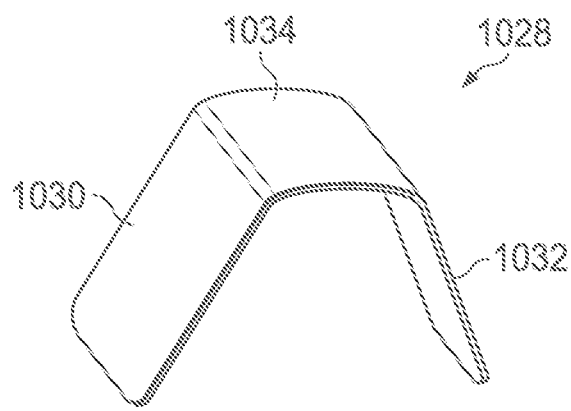
FIG. 34A illustrates an intrapartum pelvic floor support device according to an embodiment of the present disclosure.

FIG. 34A illustrates an intrapartum pelvic floor support device 1028 according to an embodiment of the present disclosure. The intrapartum pelvic floor support device 1028 includes first and second compression elements 1030, 1032 and central compression element 1034. The intrapartum pelvic floor support device 1028 has a shape analogous to the perianal support member 102, but differs in that the intrapartum pelvic floor support device 1028 has a different width to height ratio. For example, the central compression element 1034 is significantly wider (e.g., defined along the frontal plane, transverse to the sagittal plane) than the perianal support member 102's contact surface 104. In an embodiment, the central compression element 1034 has a width sufficiently wide to laterally engage tissue superficial to at least a portion of the transverse perineal muscles 84 of a patient 10 when applied.

The central compression element 1034 may be contoured to follow the curve of the gluteal cleft 13 of a patient 10, for example curving upward toward the coccyx at a posterior end of the intrapartum pelvic floor support device 1028 (e.g., an end of the device that is situated at a proximal end of a patient 10). In an embodiment, the intrapartum pelvic floor support device 1028 may also include a flare at an anterior portion (e.g., an end of the device that is situated at an anterior end of a patient 10). This flare may be v-shaped so as to extend towards opposite sides of a vaginal opening 11 of a patient 10. By flaring towards opposite sides of the vaginal opening 11, the intrapartum pelvic floor support device 1028 may additionally provide pelvic floor support to at least a portion of the ischiocavernosus muscles 82.

The intrapartum pelvic floor support device 1028 may be held in place against the patient 10 according to one or more of the embodiments discussed above with respect to the device of FIG. 26A, as well as discussed above with respect to FIGS. 1-3.

FIG. 34B illustrates an alternative embodiment of the intrapartum pelvic floor support device 1028. As illustrated in FIG. 34B, instead of a relatively flat surface as in FIG. 34A, the central compression element 1034 has a concave inner surface, described elsewhere as a small valley, resulting in two ridges that may engage tissue superficial or superior to lateral muscles of the pelvic floor, such as the levator ani muscles 88, the transverse perineal muscles 84, and the ischiocavernosus muscles 82 to name a few examples.

FIG. 34C illustrates an alternative embodiment of the intrapartum pelvic floor support device 1028. In FIG. 34C, the lateral width of the central compression element 1034 varies along the length of the intrapartum pelvic floor support device 1028, resembling a dumbbell shape as an example. For example, the anterior portion of the intrapartum pelvic floor support device 1028 that is placed near the vaginal opening 11 (the portion of the device in FIG. 34C facing the top of the page) may have a first width that is relatively large in order to support the pelvic floor muscles in that region. As the central compression element 1034 continues down along midline axis of the patient 10, a middle portion of the intrapartum pelvic floor support device 1028 may have a second width that is relatively small in order to support the pelvic floor muscles in the region while allowing for the anatomical contours of the region at and posterior to the anal orifice 90, which cause the gluteal cleft 13 to be narrower in that region. The posterior portion of the intrapartum pelvic floor support device 1028, which is placed posterior to the anal orifice 90, may resume a width that is larger than the second width. In an embodiment, the posterior portion may have the first width as well, or alternatively may have a smaller or larger width than the first width while still remaining greater than the second width.

FIG. 34D illustrates an alternative embodiment of the intrapartum pelvic floor support device 1028. In FIG. 34D, the lateral width of the central compression element 1034 varies along the length of the intrapartum pelvic floor support device 1028, resembling a V-shape as an example. For example, the anterior portion of the intrapartum pelvic floor support device 1028 that is placed near the vaginal opening 11 (the portion of the device in FIG. 34D facing the top of the page) may have a first width that is relatively large in order to support the pelvic floor muscles in that region. As the central compression element 1034 continues down along midline axis of the patient 10, the width of the central compression element 1034 gradually decreases towards a common point at the posterior portion of the device. As a result, a width of the anterior portion of the central compression element 1034 is greater than a width of the posterior portion of the central compression element 1034.

Figure 35:
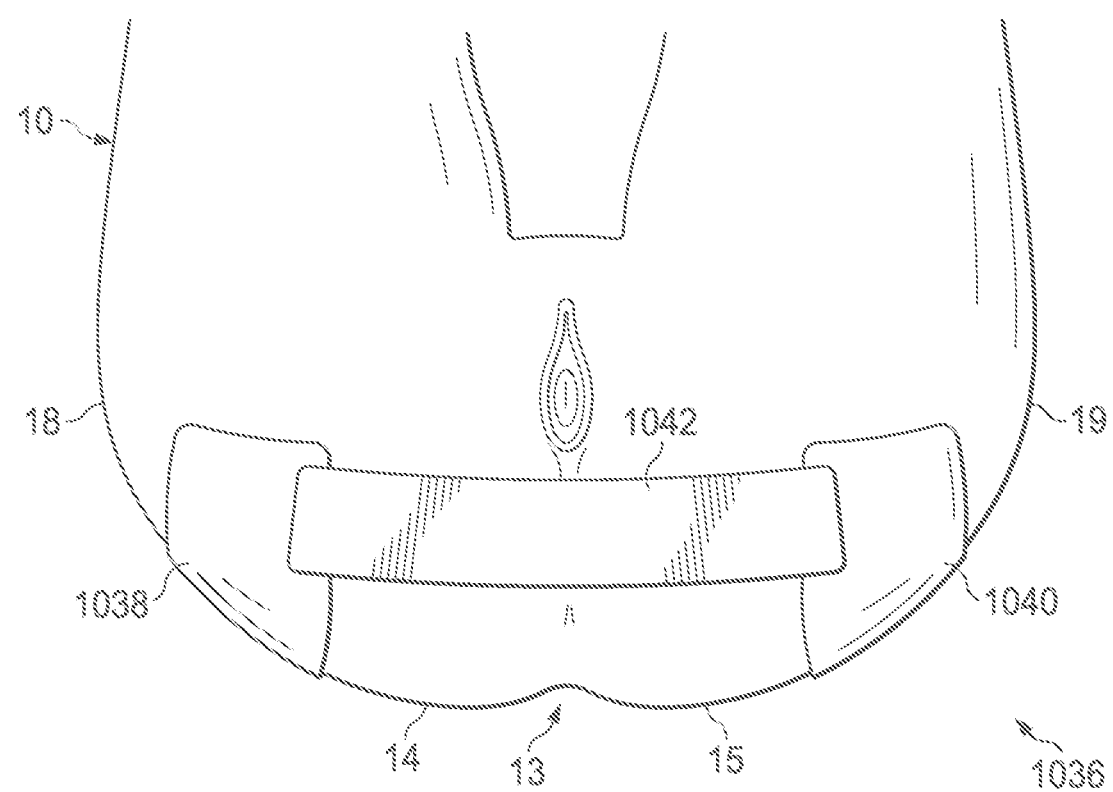
FIG. 35 illustrates an intrapartum pelvic floor support device positioned on a patient according to an embodiment of the present disclosure.

FIG. 35 illustrates an intrapartum pelvic floor support device 1036 positioned on a patient 10 according to an embodiment of the present disclosure. The intrapartum pelvic floor support device 1036 includes anchor pads 1038, 1040 on lateral sides of buttocks 14, 15 respectively, for example near the crowns of the buttocks 14, 15 on skin superficial or superior to the gluteus maximus muscles 89. The anchor pads 1038, 1040 may be attached to the skin of the patient 10 by way of an adhesive, as discussed with respect to other embodiments above. For example, the adhesive may be a skin-friendly, rubber based adhesive.

The intrapartum pelvic floor support device 1036 also includes a tissue retention strap 1042 that is releasably connected laterally to each anchor pad 1038, 1040. The tissue retention strap 1042 may be constructed of a flexible material. Further, the tissue retention strap 1042 may be formed of inner and outer portions, where the outer portion is formed of a polyurethane material and the inner portion is formed of a nylon material. The tissue retention strap 1042 may have sufficient elasticity that it stretches before the anchor pads 1038, 1040 begin detaching from the patient 10's skin at the buttocks 14, 15. As shown, the tissue retention strap 1042 extends laterally from buttock 14 to buttock 15. In an embodiment, the tissue retention strap 1042 extends laterally between the buttocks 14, 15 over the anal orifice 90, while still allowing access to the vaginal opening 11. The length of the tissue retention strap 1042 is sufficient to extend from the anchor pad 1038 to the anchor pad 1040, while a width of the tissue retention strap 1042 is less than the length. In an alternative embodiment, the tissue retention strap 1042, anchor pad 1038, and anchor pad 1040 may be integrally formed together, for example from the same material. The intrapartum pelvic floor support device 1036 may have a shape as illustrated in FIG. 35, or alternatively may have a dumbbell shape such as illustrated in FIG. 34C with the narrow portion extending over the pelvic floor region and the wide portions serving as the anchor pads. In this alternative embodiment, the intrapartum pelvic floor support device 1036 may be applied to patient 10 by adhering one anchor region (e.g., corresponding to where anchor pad 1038 was) to a lateral side of a buttock, e.g. buttock 14, pulling the strap portion of the intrapartum pelvic floor support device 1036 toward the other buttock's lateral side to a desired tautness while also pressing the tissue of the buttock 15 toward the buttock 14, and adhering the second anchor region to a lateral side of the second buttock 15.

In place, the tissue retention strap 1042 is connected to each of the anchor pads 1038, 1040 with sufficient tension that it pulls the buttocks 14, 15 toward each other. The tissue retention strap 1042 may be connected to the anchor pads 1040, 1042 with adhesive, hook and loop system, or other type of fastener. The pulling of the buttocks 14, 15 toward each other results in compression of the pelvic floor muscles and prevention of movement therefrom, providing pelvic floor support.

Figure 36:
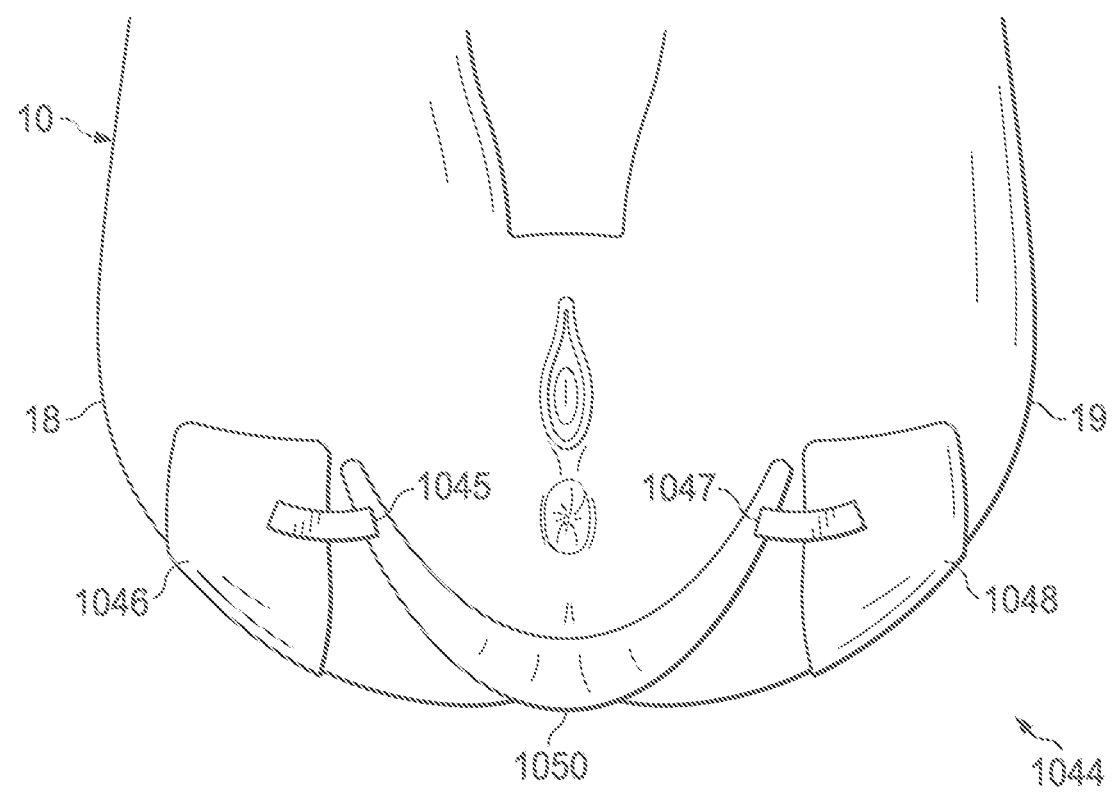
FIG. 36 illustrates an intrapartum pelvic floor support device positioned on a patient according to an embodiment of the present disclosure.

FIG. 36 illustrates an intrapartum pelvic floor support device 1044 positioned on a patient 10 according to an embodiment of the present disclosure. In an embodiment, the intrapartum pelvic floor support device 1044 is a variant of the intrapartum pelvic floor support device 1036 discussed above with respect to FIG. 35 and operates to similar results. The intrapartum pelvic floor support device 1044 includes anchor pads 1046, 1048 and curved component 1050. The curved component 1050 is connected to the anchor pad 1046 by way of tissue retention strap 1045 and to the anchor pad 1048 by way of tissue retention strap 1047. The curved component 1050 has an arcuate shape that curves away from the vaginal opening 11 (e.g., a boomerang shape with ends pointing up toward the anterior of the patient 10 and a central portion extending down toward the posterior of the patient 10). The arcuate shape of the curved component 1050 provides greater access to the pelvic area of the patient 10 during childbirth. Although illustrated as extending posterior to the anal orifice 90, the curved component 1050 may be located across different regions over the pelvic floor area that leaves the central portion posterior to the vaginal opening 11, for example such that the central portion extends over the anal orifice 90.

In an embodiment, the curved component 1050 is composed of a relatively solid component, such as a type of plastic or metal. The tissue retention straps 1045, 1047 may be composed of one or more materials as discussed above with respect to the tissue retention strap 1042 of FIG. 35 above. The intrapartum pelvic floor support device 1044 provides pelvic floor support by pulling the buttocks 14, 15 together to compress tissues of the pelvic floor. For example, proximal ends of the tissue retention straps 1045, 1047 (e.g., proximal to the midline of the patient 10) may be releasably or permanently connected to lateral ends of the curved component 1050 as illustrated in FIG. 36. The distal ends of the tissue retention straps 1045, 1047 may be pulled to a desired tightness and releasably connected to the respective anchor pads 1046, 1048. The amount of pressure applied to tissues of the pelvic floor may be varied based upon the level of tightness achieved by placement of one or both of the tissue retention straps 1045, 1047.

In an alternative embodiment not shown in FIG. 36, the curved component 1050 and tissue retention straps 1045, 1047 may be replaced by a single tissue retention strap that has a laterally pre-contoured shape that also results in an arcuate shape to provide increased access to the pelvic area. In such an embodiment, the single tissue retention strap may be composed of a material with sufficient firmness to retain its arcuate shape in the anterior-posterior direction under stress while still retaining sufficient flexibility in the lateral direction to prevent tearing or breaking of the strap. This may be accomplished, for example, by a plastic mesh with sufficient flexibility in the lateral direction and firmness in the anterior-posterior direction. In another alternative embodiment, the curved component 1050, tissue retention straps 1045, 1047, anchor pad 1046, and anchor pad 1048 may be integrally formed together, for example from the same material. In this alternative embodiment, the intrapartum pelvic floor support device 1044 may be applied to patient 10 by adhering one anchor region (e.g., corresponding to where anchor pad 1046 was) to a lateral side of a buttock, e.g. buttock 14, pulling the strap portion of the intrapartum pelvic floor support device 1044 toward the other buttock's lateral side to a desired tautness while also pressing the tissue of the buttock 15 toward the buttock 14, and adhering the second anchor region to a lateral side of the second buttock 15.

Figure 37A:
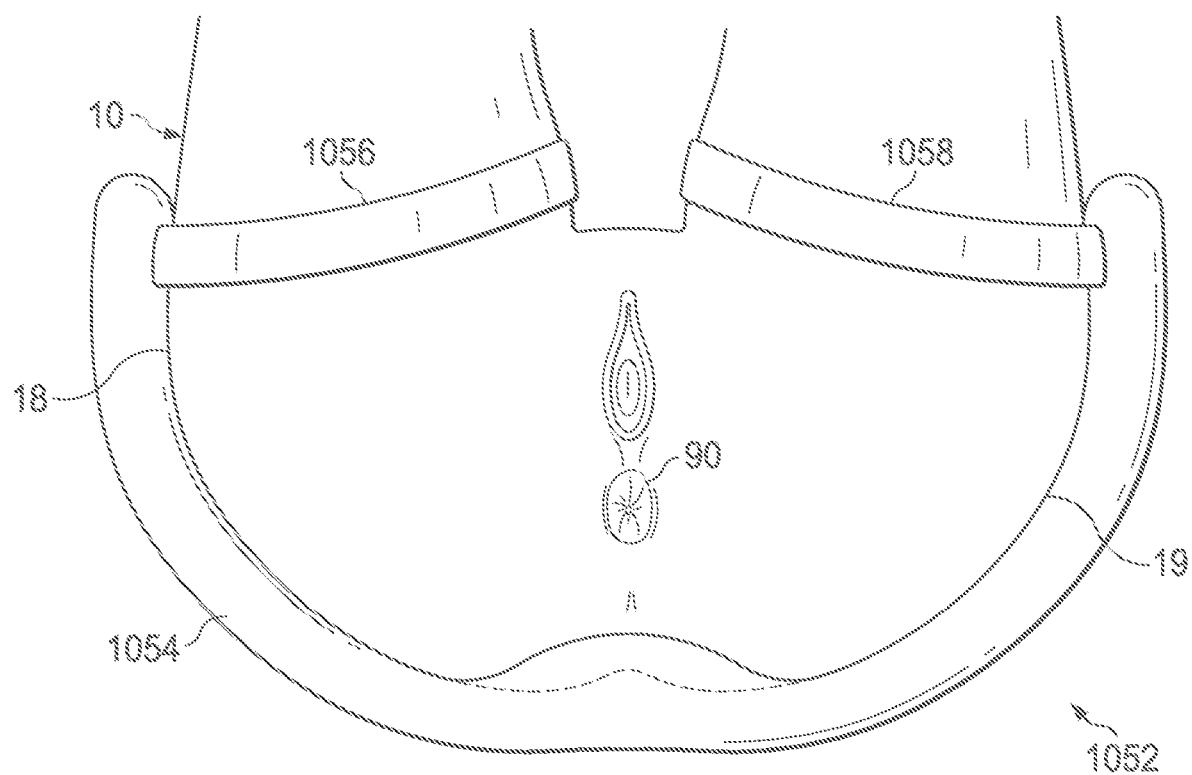
FIG. 37A illustrates a bottom view of an intrapartum pelvic floor support device positioned on a patient according to an embodiment of the present disclosure.

FIG. 37A illustrates an intrapartum pelvic floor or anococcygeal support device 1052 positioned on a patient 10 according to an embodiment of the present disclosure. The intrapartum pelvic floor support device 1052 includes a contoured support 1054 and straps 1056, 1058. In an embodiment, the contoured support 1054 is an inflatable contoured support, for example using some form of fluid such as air or liquid as the inflation medium. Where the contoured support 1054 is inflatable, it may be partially inflatable (e.g., a portion of the contoured support 1054 comes pre-inflated or is composed of a more solid material around which the rest of the contoured support 1054 is inflated) or substantially fully inflatable (e.g., the contoured support 1054 has substantially no fluid within it prior to first use). The contoured support 1054 may be contoured to the general shape of the buttocks 14, 15 as well as the gluteal cleft 13 therebetween at a posterior area of the patient 10.

In the pictured embodiment, the contoured support 1054 is held in place against the patient 10 by way of the straps 1056, 1058, which are placed laterally to the crowns of the buttocks 14, 15. The contoured support 1054 may be connected to the straps 1056, 1058 with an adhesive or hook and loop system, as described with respect to other embodiments above. Alternatively, the straps 1056, 1058 may be releasably inserted through slots in the contoured support 1054. As another alternative, the straps 1054, 1056 may be permanently connected to the contoured support 1054, e.g., formed with the contoured support 1054. As will be recognized, where adhesives are used, the straps 1056, 1058 may alternatively be anchor pads as described in other previous embodiments. Each of straps 1056, 1058 may be releasably connectable. For example, each strap 1056, 1058 may have a hook and loop system that enables the circumferential size of the straps to be larger or smaller while closed to accommodate varying leg sizes. In an alternative embodiment, the straps 1056, 1058 may use a buckle to be adaptively sized to the particular size of a given patient 10. In another alternative embodiment, the straps 1056, 1058 may use a ratchet-type system with a spring-loaded finger on a receiving end of the straps and corresponding teeth on an inserting end of the straps so that the straps may adaptively sized to the given size of a given patient 10. The straps 1056, 1058 may be attached to the patient 10 at the thighs of the patient 10, for example close to the pelvic region as illustrated in FIG. 37A.

After application to a patient 10, the intrapartum pelvic floor support device 1052 may be inflated as much as desired to provide pelvic floor support. The intrapartum pelvic floor support device 1052 provides pelvic floor and/or anococcygeal support by cradling the buttocks 14, 15 and laterally compressing the tissue between the buttocks, including the pelvic floor muscles, together. The compression may prevent one or more pelvic floor muscles from trauma such as may result from overstretching, tissue distension, or other strain during childbirth. After the initial placement and inflation on the patient 10, the contoured support 1054 may be further inflated or deflated to increase or decrease, respectively, the amount of compression on one or more tissues associated with the pelvic floor.

Figure 37B:
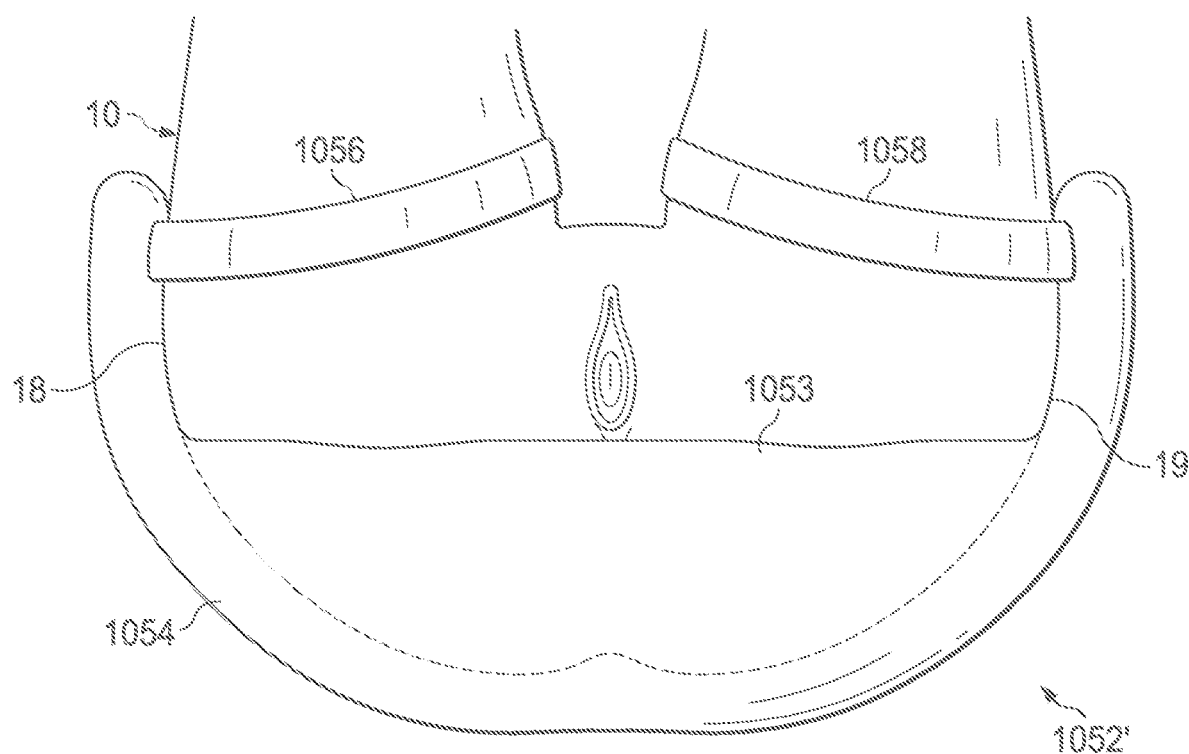
FIG. 37B illustrates a bottom view of an intrapartum pelvic floor support device positioned on a patient according to an embodiment of the present disclosure.
Figure 37C:
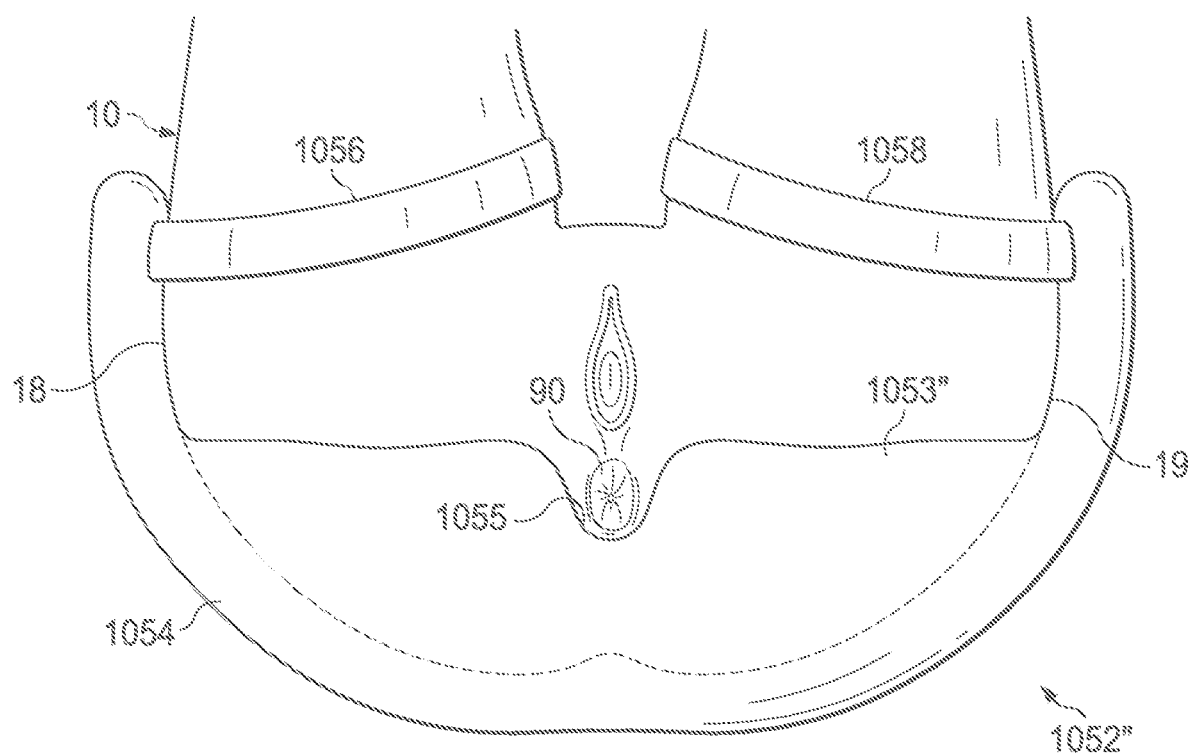
FIG. 37C illustrates a bottom view of an intrapartum pelvic floor support device positioned on a patient according to an embodiment of the present disclosure.

FIGS. 37B and 37C illustrate alternative embodiments of the intrapartum pelvic floor support device 1052. As illustrated in FIG. 37B, instead of the contoured support 1054 extending across only a posterior portion or outer buttock region of the patient 10, the contoured support 1054' of the intrapartum pelvic floor support device 1052' also includes a support structure 1053 that extends from the lateral flanks 18, 19 inward toward the gluteal cleft 13, covering the anal orifice 90 and tissues superior to the pelvic floor (e.g., the skin overlying the pelvic floor). The support structure 1053 may also be inflatable according to one or more of the embodiments discussed above with respect to FIG. 37A. The inner surface of the support structure 1053 may be concave to approximately follow the contour of the buttocks 14, 15, and the gluteal cleft 13. The material of the support structure 1053 may be pre-formed with the concave structure. In addition or in the alternative, the inner material may also be more flexible than the outer material of the contoured support 1054 such that, when inflated, the material of the inner surface of the support structure 1053 may adapt in shape to accommodate the contours of the buttocks 14, 15, and the gluteal cleft.

Figure 37D:
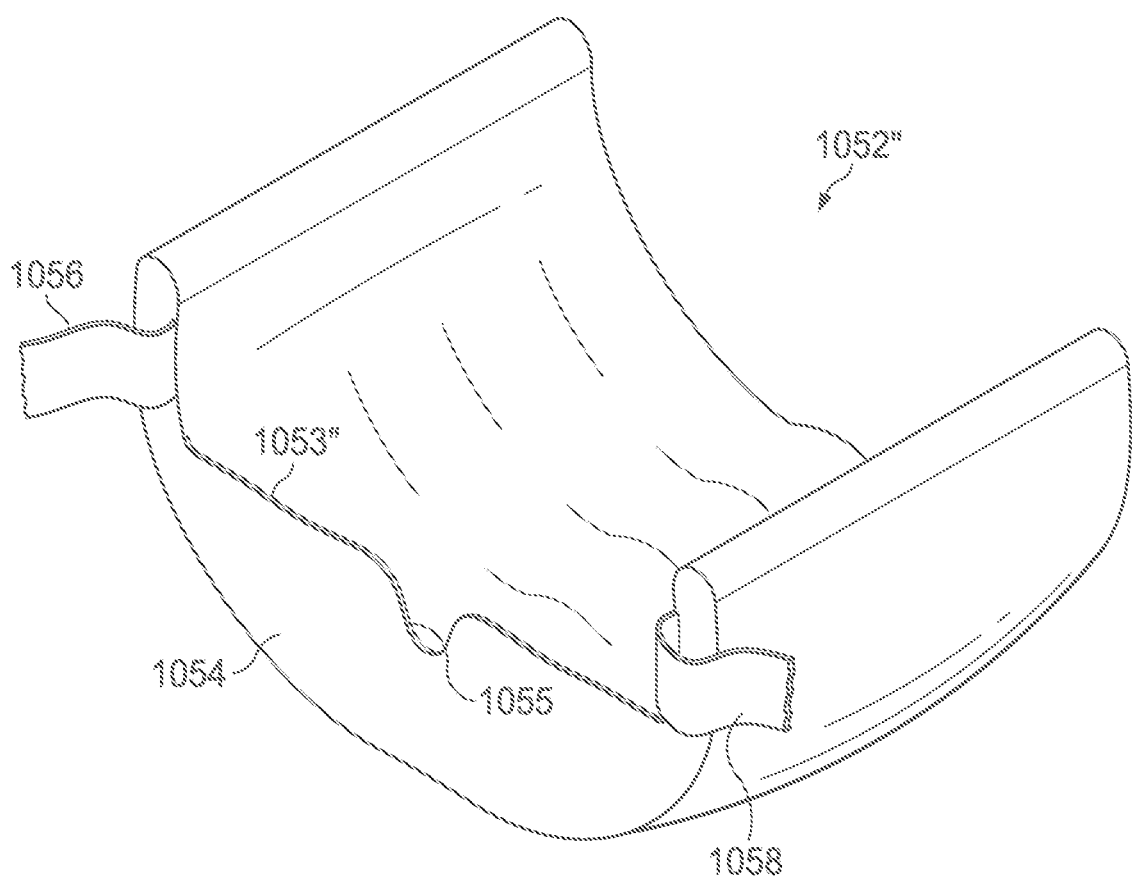
FIG. 37D illustrates a perspective view of an intrapartum pelvic floor support device shown in FIG. 37C according to an embodiment of the present disclosure.
Figure 37E:
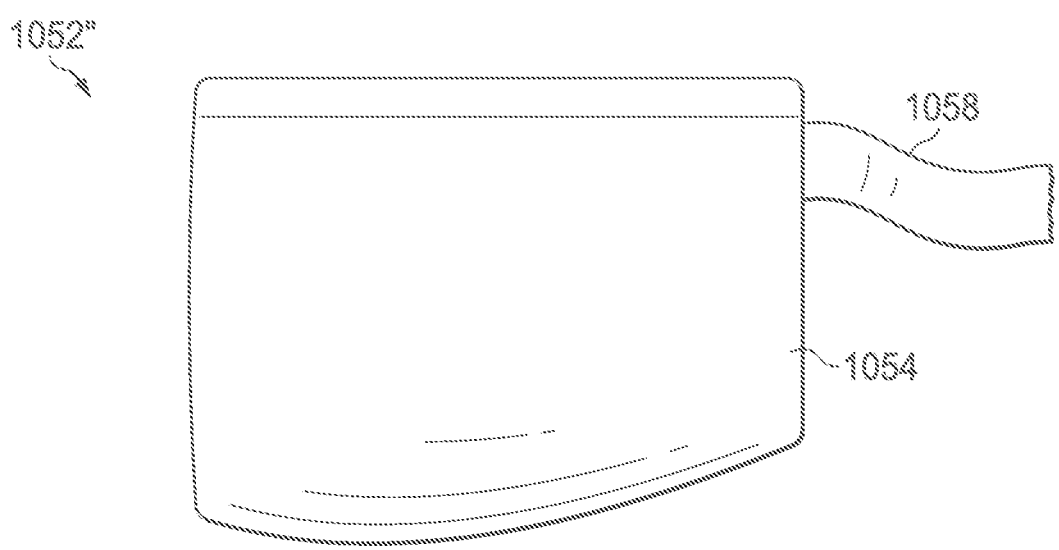
FIG. 37E illustrates a side view of an intrapartum pelvic floor support device shown in FIG. 37C according to an embodiment of the present disclosure.

FIGS. 37C-37E illustrate another alternative embodiment to that of FIGS. 37A and 37B. FIG. 37C illustrates a bottom view of an intrapartum pelvic floor support device 1053", FIG. 37D illustrates a perspective view of an intrapartum pelvic floor support device 1053", and FIG. 37E illustrates a side view of an intrapartum pelvic floor support device 1053". As illustrated in 37C, the intrapartum pelvic floor support device 1052" includes a support structure 1053". Unlike the support structure 1053 depicted in FIG. 37B, however, the support structure 1053" includes a recess 1055 that exposes the anal orifice 90.

Figure 38:
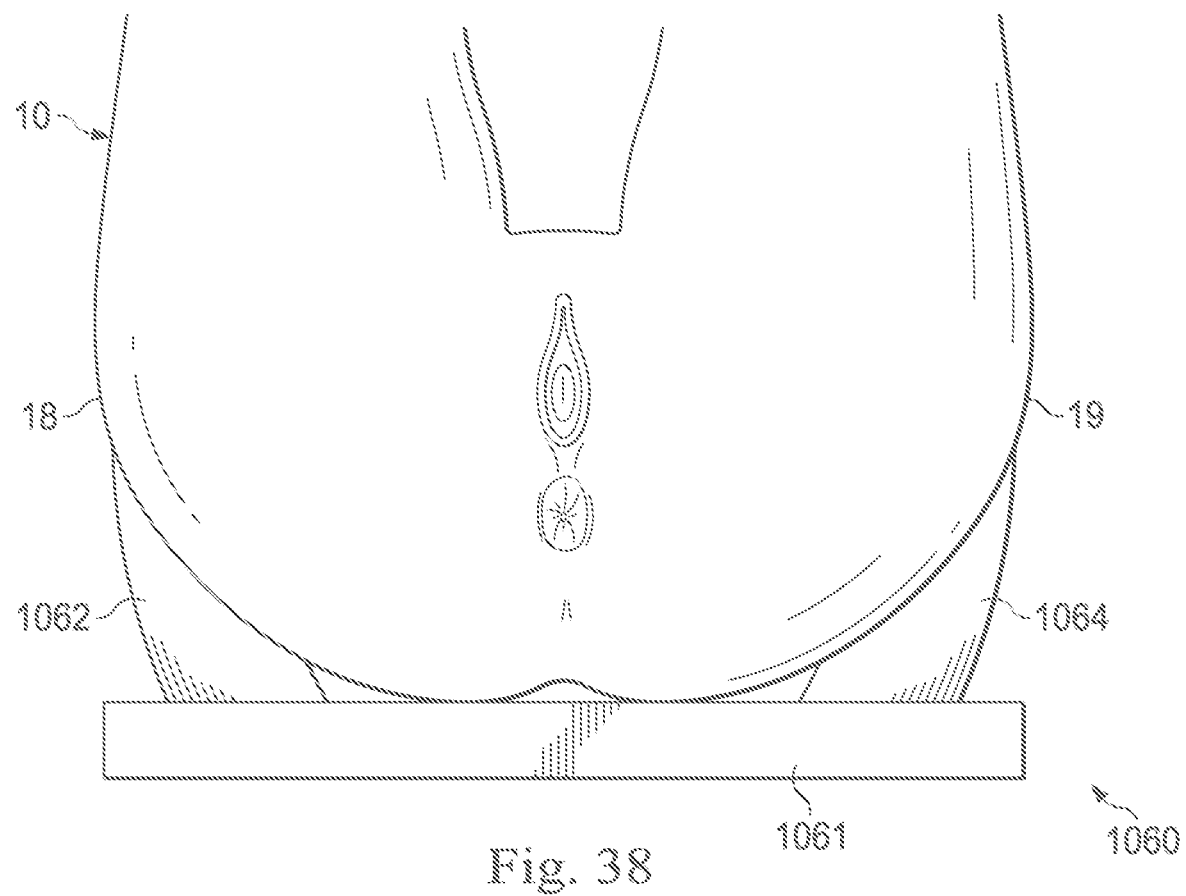
FIG. 38 illustrates an intrapartum pelvic floor support device positioned on a patient according to an embodiment of the present disclosure.

FIG. 38 illustrates an intrapartum pelvic floor support device 1060 positioned on a patient 10 according to an embodiment of the present disclosure. The intrapartum pelvic floor support device 1060 includes a support base 1061 and lateral supports 1062, 1064. In an embodiment, the lateral supports 1062, 1064 are physically joined to the support base 1061, for example by way of one or more connectors or adhesive. In another embodiment, the lateral supports 1062, 1064 are formed with the support base 1061 together, for example by injection molding. The intrapartum pelvic floor support device 1060 may be placed at a posterior region of the patient 10, as shown in FIG. 38, for example near the coccyx.

The support base 1061 may be composed of a polymer, a metal, or other firm material capable of providing an opposing lateral force to that exerted on the lateral supports 1062, 1064 when applied during the intrapartum period. The intrapartum pelvic floor support device 1060 may be attached to a patient bed for additional lateral support. Alternatively, the intrapartum pelvic floor support device 1060 may be incorporated into a platform that the patient 10 lies on, such as on a bed or some other underlying support. In another alternative embodiment, the intrapartum pelvic floor support device 1060 may be made to resemble a pillow that the patient 10 lies on.

The lateral supports 1062, 1064 may be releasably connected to the support base 1061 in order to enable repositioning of the intrapartum pelvic floor support device 1060 to provide more or less support to the patient 10's pelvic floor as desired. As one example, the lateral supports 1062, 1064 may be attached to a track that is placed within a groove in the surface of the support base 1061 that faces/contacts the patient 10. The lateral supports 1062, 1064 may be able to slide along this track in a reciprocal fashion, e.g. applying sliding pressure to the lateral support 1062 to move it laterally towards the gluteal cleft 13 of the patient 10 causes a corresponding lateral move of the lateral support 1064 close to the gluteal cleft 13, and vice versa. In this embodiment, once the lateral supports 1062, 1064 have been moved to a desired position, they may be locked by any suitable locking mechanism as will be recognized by those skilled in the relevant art(s). As another example, the support base 1061 may include a plurality of holes or pegs spaced along its upper surface. Each of the lateral supports 1062, 1064 may have corresponding pegs or holes, respectively, to releasably join with the support base 1061 at different lengths from one another.

The support base 1061 operates together with the lateral supports 1062, 1064 in order to provide pressure laterally to the buttocks 14, 15, for example at locations extending from near the crowns of the buttocks 14, 15 toward the flanks 18, 19. In an embodiment, the lateral supports 1062, 1064 may extend from the crowns of the patient 10's hips where the reference numbers 18 and 19 point to near the crowns of the buttocks 14, 15. The lateral supports 1062, 1064 may alternatively extend from near the crowns of the buttocks 14, 15 toward a location midway between the patient 10's crowns of the hips. This applies lateral pressure to compress the buttocks 14, 15 together, resulting in pressure being applied to one or more tissues of the pelvic floor, thereby supporting the pelvic floor during the intrapartum period.

Figure 39:
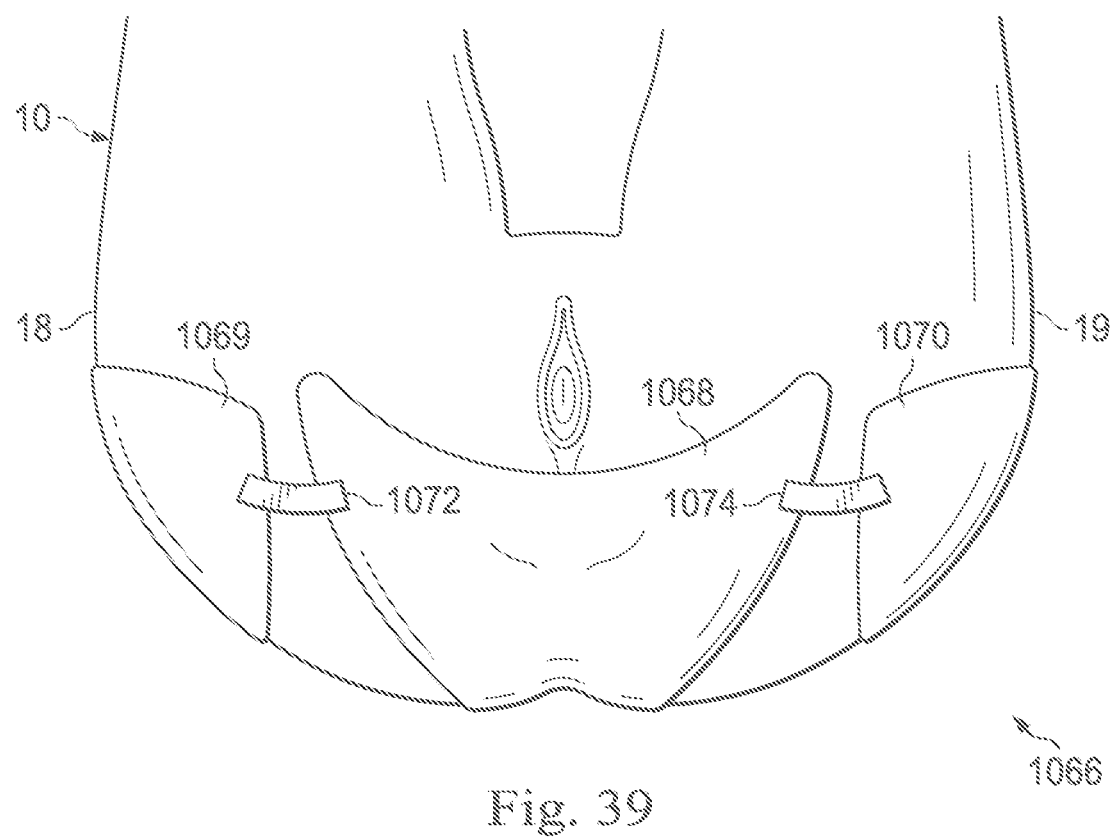
FIG. 39 illustrates an intrapartum pelvic floor support device positioned on a patient according to an embodiment of the present disclosure.

FIG. 39 illustrates an intrapartum pelvic floor support device 1066 positioned on a patient 10 according to an embodiment of the present disclosure. The intrapartum pelvic floor support device 1066 includes a support device 1068, anchor pads 1069, 1070, and retention straps 1072, 1074. The support device 1068 may be connected to the anchor pads 1069, 1070 via the retention straps 1072, 1074 respectively. The anchor pads 1069, 1070 may be attached to the skin of the patient 10 laterally near the crowns of the buttocks 14, 15 by way of an adhesive, such as discussed with respect to other embodiments above. For example, the adhesive may be a skin-friendly, rubber based adhesive. The retention straps 1072, 1074 may connect with one or both of the support device 1068 and the anchor pads 1069, 1070 with an adhesive or hook and loop system, as described with respect to other embodiments above to name just a few examples. Where the retention straps 1072, 1074 connect with just one of either the anchor pads or the support device, the retention straps may be formed with the other. For example, in an embodiment the retention straps 1072, 1074 may be formed as part of the anchor pads 1069, 1070 as regions not adhered to the skin of the patient 10. In such an embodiment, the retention straps 1072, 1074 are releasably connected with the support device 1068 while being an integral part of the anchor pads 1069, 1070. In another alternative embodiment, the support device 1068, retention straps 1072, 1074, anchor pad 1069, and anchor pad 1070 may be integrally formed together, for example from the same material. In this alternative embodiment, the intrapartum pelvic floor support device 1066 may be applied to patient 10 by adhering one anchor region (e.g., corresponding to where anchor pad 1069 was) to a lateral side of a buttock, e.g. buttock 14, pulling the support device 1068 of the intrapartum pelvic floor support device 1066 toward the other buttock's lateral side to a desired tautness while also pressing the tissue of the buttock 15 toward the buttock 14, and adhering the second anchor region to a lateral side of the second buttock 15.

The support device 1068 may be contoured to the anatomy of the patient 10. For example, the central portion of the support device 1068 may contour to the gluteal cleft 13 of the patient 10 and include concave inner surfaces extending out laterally in order to receive the buttocks 14, 15 and generally fit their contour. The support device 1068 may extend out in the anterior direction as well, with side edges of the support device 1068 extending beyond the beginning of the vaginal opening 11 while the central portion of the support device 1068 extends in the anterior direction to stop before the vaginal opening 11, thereby covering at least a portion of the perineum as illustrated in FIG. 39. In an embodiment, the support device 1068 may have varying levels of rigidity throughout the device. For example, the central portion of the support device 1068 may be rigid and become less rigid as the support device 1068 extends out laterally from the central portion. This may result in the lateral components of the support device 1068 being more complaint to contour to the shape of the patient 10's buttocks 14, 15 when applied to the patient 10. For example, the support device 1068 may have increased rigidity at the central portion, e.g. focused at an area at and/or near the anal sphincter 86 with increased flexibility closer to the perineum of the patient 10 and as the support device 1068 extends laterally away from the central portion.

Further, the configuration of the central portion may be designed so as to provide different levels of pressure to the tissue it comes in contact with. In one example, the central portion of the support device 1068 may have a ridge that fits within the gluteal cleft 13 and approximately uniformly comes into contact with the pelvic floor tissue extending from the support device 1068's anterior portion to its posterior portion. The ridge may have a uniform height to apply uniform pressure along the cleft, or alternatively may have an increase or decrease in height in one or more areas to provide more or less pressure, respectively, at those points. In an alternative embodiment, the central portion may have two parallel ridges and a small valley therebetween that runs along the length from the anterior to posterior portions of the patient 10, such as discussed above with respect to FIG. 34B.

In an alternative embodiment, the lateral components of the support device 1068, and/or the placement/size of the anchor pads 1069, 1070 are large enough that lateral edges of the support device 1068 may releasably attach directly to the anchor pads 1069, 1070. In this embodiment, there is little need for the retention straps 1072, 1074 and may be omitted. The lateral edges may releasably attach using a hook and loop system or adhesive, to name some examples.

In place, the support device 1068 may cover several muscles of the pelvic floor, for example at least a portion of the bulbocaervnosus muscles 80, at least a portion of the ischiocavernosus muscles 82, the transverse perineal muscles 84, the external anal sphincter muscle 86, and the levator ani muscle 88, thereby providing pelvic floor support. As illustrated, the intrapartum pelvic floor support device 1066 may provide this support and/or pressure without interfering with the birthing canal or vaginal opening 11. In this manner, the intrapartum pelvic floor support device 1066 may non-invasively reduce and/or inhibit pelvic floor trauma.

Figure 40:
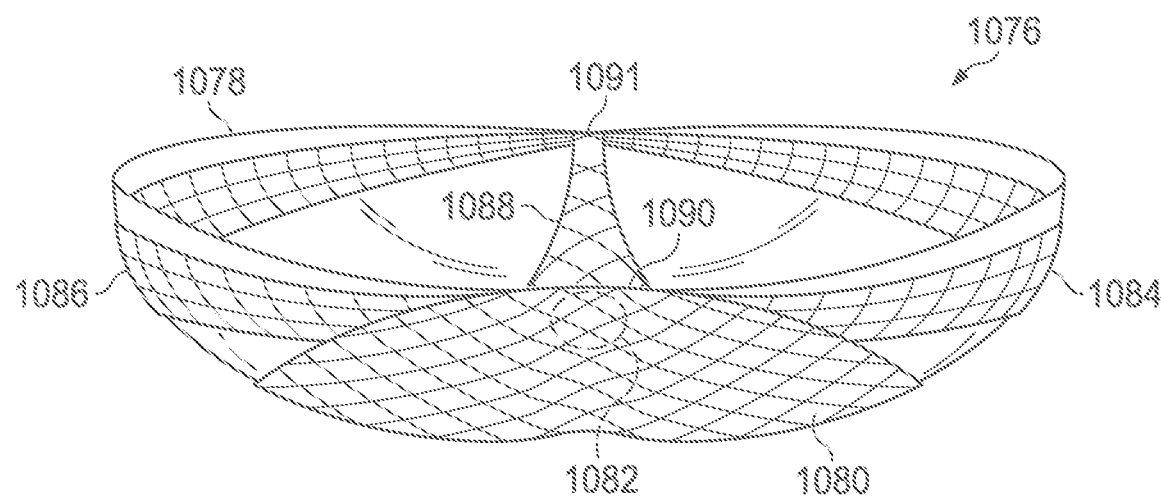
FIG. 40 illustrates an intrapartum pelvic floor support device according to an embodiment of the present disclosure.
Figure 41:
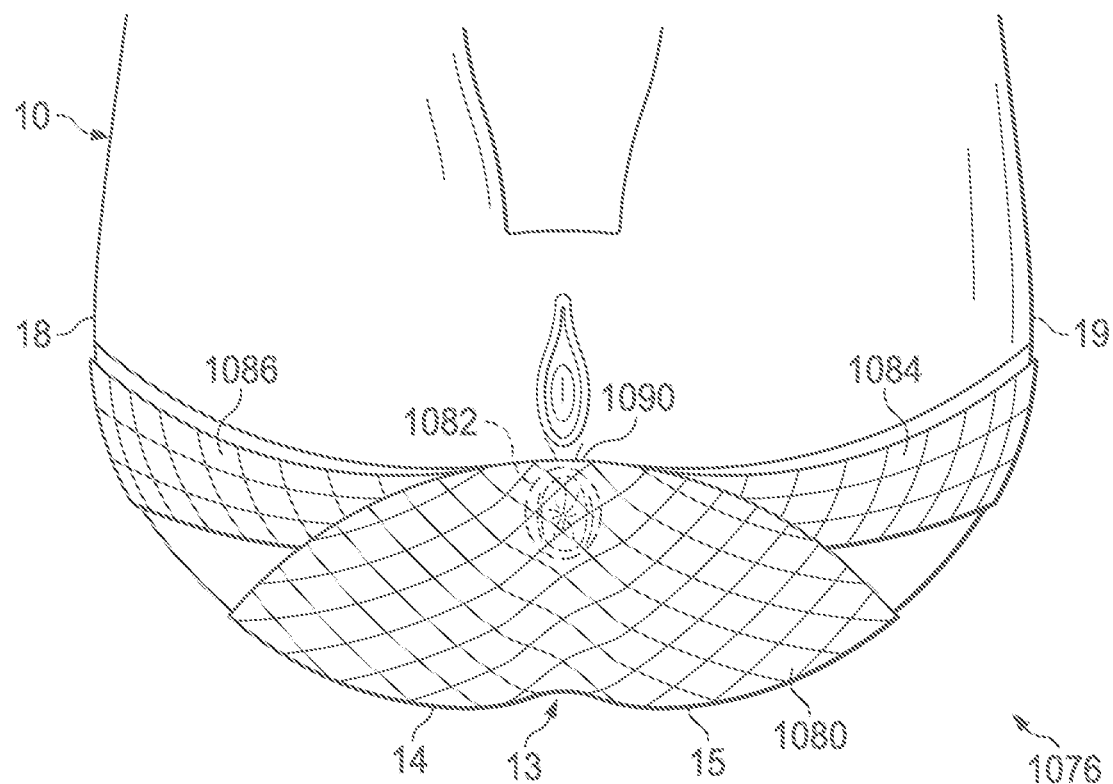
FIG. 41 illustrates an intrapartum pelvic floor support device positioned on a patient according to an embodiment of the present disclosure.

FIGS. 40 and 41 illustrate an intrapartum pelvic floor support device 1076 according to an embodiment of the present disclosure. The intrapartum pelvic floor support device 1076 includes thin sheet 1078, anterior mesh 1080, optional hole 1082, lateral support meshes 1084 and 1086, and central support mesh 1088. The thin sheet 1078 may be a thin film of plastic that is flexible enough to conform to the anatomy of the patient 10. In an embodiment, the thin sheet 1078 may be composed of a medical grade plastic. The thin sheet 1078 may have adhesive throughout its top side in order to adhere to the skin of the patient 10. The thin sheet 1078 may extend from an anterior portion 1090 that reaches the perineum area adjacent to the vaginal opening 11 in a posterior direction to the posterior portion 1091 that may curve around the coccyx and extend upward the back of the patient 10, for example near or at the S3 or S4 vertebrae. Further, the thin film 1078 extends between lateral support meshes 1086 and 1084.

The intrapartum pelvic floor support device 1076's anterior mesh 1080 is sized and shaped so as to cover and support the pelvic floor of the patient 10. As shown in FIGS. 40 and 41, the anterior mesh 1080 covers the tissues of the perineum and extends in the posterior direction over the anus and onward, curving upward with the curve of the gluteal cleft 13. The anterior mesh 1080 may include, for example, an interwoven network of fibers or rods that are flexible in one direction but more rigid in another. The anterior mesh 1080 is connected to the lateral support meshes 1084, 1086 as well as the central support mesh 1088. The anterior mesh 1080 transfers the load applied to it from the tissues of the pelvic floor to the lateral support meshes 1084, 1086 and the central support mesh 1088. In an embodiment, the anterior mesh 1080, lateral support meshes 1084, 1086 and central support mesh 1088 are thicker than the thin sheet 1078 in order to provide support to the pelvic floor. In an embodiment, the stiffness of the anterior mesh 1080 may be three to four times stiffer than that of the lateral support meshes 1084, 1086 and the central support mesh 1088. As shown in FIGS. 40-41, the anterior support mesh 1080 may have an optional hole 1082 that lies generally over the region of the anal orifice 90. The optional hole 1082 may be, for example, a section of the anterior support mesh 1080 that has a circular perforation. As a result, if desired the perforated area of the anterior mesh 1080 may be removed before or after the intrapartum pelvic floor support device 1076 has been applied to the patient 10.

Adhesive may have been applied previously to the entirety of the side of the intrapartum pelvic floor support device 1076 that is attached to the patient 10. Alternatively, adhesive may be applied to the intrapartum pelvic floor support device 1076 or to the patient 10 immediately prior to the intrapartum pelvic floor support device 1076 being temporarily attached to the patient 10. Where the intrapartum pelvic floor support device 1076 has adhesive previously applied, the intrapartum pelvic floor support device 1076 may include three separate sheets of backing on the side that has the adhesive. In order to apply the intrapartum pelvic floor support device 1076 to the patient 10, a person may first remove the backing (or apply adhesive in alternative embodiments) and then either have the patient 10 sit on the intrapartum pelvic floor support device 1076 on the exposed adhesive side, or apply to the patient 10 while the patient 10 is in a sitting/squatting/reclined position. This may include manually assisting the portion of the device including the anterior support mesh 1080 and/or the central support mesh 1088 to adequately match the contour of the patient 10, such as entering the gluteal cleft 13 and following the contour of the buttocks 14, 15. The intrapartum pelvic floor support device 1076 is positioned on the patient 10 so that the anterior mesh 1080 of the anterior portion 1090 is located near the vaginal opening 11 and extending from there in posterior and lateral directions.

In an alternative embodiment, instead of the thin sheet 1078 and the meshes 1080, 1084, 1086, and 1088, the intrapartum pelvic floor support device 1076 may be composed of a single device, such as one that has been injection molded. In this embodiment, the intrapartum pelvic floor support device 1076 may include ribbing with a variety of different strengths throughout the surface of the device. For example, there may be ribbing throughout but the ribbing where the anterior support mesh 1080 would otherwise be is thicker and/or otherwise stronger than other regions where the FIGS. 40, 41 do not show any mesh. In another alternative embodiment, the thin sheet 1078 is not included. In this embodiment, the adhesive would be applied to the sides of the meshes 1080, 1084, 1086, and 1088 that face and attach to the patient 10.

In an embodiment, the intrapartum pelvic floor support device 1076 may also include one or more sensors designed to detect stretching of the intrapartum pelvic floor support device 1076. This stretching may be correlated to a condition of one or more muscles of the pelvic floor. Further, the different rods or fibers of the meshes 1080, 1084, 1086, and 1088 may be color fibers that change colors based on the level of stretching they undergo. This color change may be correlated to an amount of stretching the underlying muscles have undergone, a level of stress the muscles of the pelvic floor may have experienced, or feedback to indicate whether more or less strain should be applied during childbirth without causing pelvic floor trauma.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure. Furthermore, although elements of the described embodiments may be described or claimed in the singular, the plural is contemplated unless limitation to the singular is explicitly stated. Additionally, all or a portion of any aspect and/or embodiment may be utilized with all or a portion of any other aspect and/or embodiment.

What is claimed is:

1. A non-invasive intrapartum pelvic floor support device for use on a patient, comprising:
   a central support element sized and configured to fit within a gluteal cleft of the patient, the central support element comprising a contact surface configured and dimensioned to extend across an anal orifice of the patient in a sagittal plane of the patient from an anterior portion posterior to a vaginal opening of the patient to a posterior portion posterior to the anal orifice of the patient;
   a first flexibly deformable compression element extending from the central support element in a first lateral direction to a first distal end, the first flexibly deformable compression element comprising a first surface configured to face and flexibly conform to a curvature of a first buttock to a location toward its crown within the gluteal cleft of the patient when applied to the patient;
   and a second flexibly deformable compression element extending from the central support element in a second lateral direction to a second distal end, the second flexibly deformable compression element comprising a second surface configured to face and flexibly conform to a curvature of a second buttock to a location toward its crown within the gluteal cleft of the patient when applied to the patient, wherein the first and second flexibly deformable compression elements are integrally formed as a one piece device with the central support element; and
   a first fastening member on the first surface of the first flexibly deformable compression element disposed only between the first distal end and the contact surface, and a second fastening member on the second surface of the second flexibly deformable compression element disposed only between the second distal end and the contact surface.

2. The non-invasive intrapartum pelvic floor support device of claim 1, wherein the non-invasive intrapartum pelvic floor support device has a rigidity, the rigidity being sufficient for the contact surface to apply force to tissue superficial to a pelvic floor of the patient.

3. The non-invasive intrapartum pelvic floor support device of claim 2, wherein the rigidity varies from the central support element laterally outwardly along the first and second flexibly deformable compression elements.

4. The non-invasive intrapartum pelvic floor support device of claim 1, wherein the first fastening member includes a first releasable fastening system, and wherein the second fastening member includes a second releasable fastening system.

5. The non-invasive intrapartum pelvic floor support device of claim 4, wherein the first releasable fastening system comprises a first adhesive, and wherein the second releasable fastening system comprises a second adhesive.

6. The non-invasive intrapartum pelvic floor support device of claim 1, wherein the first fastening member is fixed on the first flexibly deformable compression element, and wherein the second fastening member is fixed on the second flexibly deformable compression element.

7. The non-invasive intrapartum pelvic floor support device of claim 1, wherein the non-invasive intrapartum pelvic floor support device is sterile.

8. The non-invasive intrapartum pelvic floor support device of claim 1, wherein the contact surface comprises a gauze pad.

9. The non-invasive intrapartum pelvic floor support device of claim 8, wherein the gauze pad comprises a material that is configured to frictionally engage perianal tissue of the patient to inhibit movement between the contact surface and the patient.

10. A non-invasive intrapartum pelvic floor support device for use on a patient, comprising:
   a central support element sized and configured to fit within a gluteal cleft of the patient, the central support element comprising a contact surface configured and dimensioned to extend across an anal orifice of the patient in a sagittal plane of the patient from an anterior portion posterior to a vaginal opening of the patient to a posterior portion posterior to the anal orifice of the patient;
   a first flexibly deformable compression element extending from the central support element in a first lateral direction to a first distal end, the first flexibly deformable compression element comprising a first surface configured to face and flexibly follow at least a part of a first buttock within the gluteal cleft of the patient when applied to the patient;
   and a second flexibly deformable compression element extending from the central support element in a second lateral direction to a second distal end, the second flexibly deformable compression element comprising a second surface configured to face and flexibly follow at least a part of a second buttock within the gluteal cleft of the patient when applied to the patient; and
   a first fastening member on the first surface of the first flexibly deformable compression element disposed only between the first distal end and the contact surface, and a second fastening member on the second surface of the second flexibly deformable compression element disposed only between the second distal end and the contact surface,
   wherein the non-invasive intrapartum pelvic floor support device has a rigidity, the rigidity being sufficient for the contact surface to apply force to tissue superficial to a pelvic floor of the patient. wherein the rigidity varies from the central support element laterally outwardly along the first and second flexibly deformable compression elements. and
   wherein the variation in rigidity is gradual and is effected by the first and second flexibly deformable compression elements thinning laterally outwardly from the central support element respectively toward the first distal end and the second distal end.

11. A non-invasive intrapartum pelvic floor support device for use on a patient, comprising:
   a central support element comprising a contact surface configured and dimensioned to extend across an anal orifice of the patient in a sagittal plane of the patient from an anterior portion posterior to a vaginal opening of the patient to a posterior portion posterior to the anal orifice of the patient, said central support element including a ridge sized and configured to fit within a gluteal cleft of the patient, said ridge having a height that decreases in both directions laterally away from the sagittal plane;
   a first flexibly deformable compression element extending from the central support element in a first lateral direction to a first distal end, the first flexibly deformable compression element comprising a first surface configured to face and flexibly follow at least a part of a first buttock within the gluteal cleft of the patient when applied to the patient;
   and a second flexibly deformable compression element extending from the central support element in a second lateral direction to a second distal end, the second flexibly deformable compression element comprising a second surface configured to face and flexibly follow at least a part of a second buttock within the gluteal cleft of the patient when applied to the patient, wherein the first and second flexibly deformable compression elements are integrally formed as a one piece device with the central support element; and
   a first fastening member on the first surface of the first flexibly deformable compression element disposed only between the first distal end and the contact surface, and a second fastening member on the second surface of the second flexibly deformable compression element disposed only between the second distal end and the contact surface.

* * * * *